(12) United States Patent
Ellermann et al.

(10) Patent No.: US 11,897,867 B2
(45) Date of Patent: Feb. 13, 2024

(54) 6-PHENYL-4,5-DIHYDROPYRIDAZIN-3(2H)-ONE DERIVATIVES AS PDE3A AND PDE3B INHIBITORS FOR TREATING CANCER

(71) Applicants: Bayer Aktiengesellschaft, Leverkusen (DE); Bayer Pharma Aktiengesellschaft, Berlin (DE); The Broad Institute, Inc., Cambridge, MA (US)

(72) Inventors: Manuel Ellermann, Berlin (DE); Timothy Lewis, Cambridge, MA (US)

(73) Assignees: Bayer Aktiengesellschaft, Leverkusen (DE); Bayer Pharma Aktiengesellschaft, Berlin (DE); The Broad Institute, Inc., Cambridge, MA (US)

( * ) Notice: Subject to any disclaimer, the term of this patent is extended or adjusted under 35 U.S.C. 154(b) by 357 days.

(21) Appl. No.: 16/635,513

(22) PCT Filed: Aug. 2, 2018

(86) PCT No.: PCT/EP2018/071016
§ 371 (c)(1),
(2) Date: Jan. 30, 2020

(87) PCT Pub. No.: WO2019/025554
PCT Pub. Date: Feb. 7, 2019

(65) Prior Publication Data
US 2020/0247783 A1 Aug. 6, 2020

Related U.S. Application Data

(60) Provisional application No. 62/541,631, filed on Aug. 4, 2017.

(51) Int. Cl.
| | | |
|---|---|---|
| C07D 403/10 | (2006.01) | |
| C07D 237/04 | (2006.01) | |
| C07D 401/10 | (2006.01) | |
| C07D 405/10 | (2006.01) | |
| C07D 413/10 | (2006.01) | |
| A61P 35/04 | (2006.01) | |
| A61P 35/00 | (2006.01) | |

(52) U.S. Cl.
CPC ............ *C07D 403/10* (2013.01); *A61P 35/04* (2018.01); *C07D 237/04* (2013.01); *C07D 401/10* (2013.01); *C07D 405/10* (2013.01); *C07D 413/10* (2013.01)

(58) Field of Classification Search
CPC ........ A61P 35/00; A61P 35/04; C07D 405/10; C07D 413/10; C07D 403/10; C07D 401/10; C07D 237/04
See application file for complete search history.

(56) References Cited

U.S. PATENT DOCUMENTS

| | | |
|---|---|---|
| 4,052,395 A | 10/1977 | Jojima et al. |
| 4,158,094 A | 6/1979 | Niznik |
| 4,334,030 A | 6/1982 | Kochanowski |
| 4,423,045 A | 12/1983 | Brown et al. |
| 4,493,835 A | 1/1985 | Hargreaves et al. |
| 4,495,185 A | 1/1985 | Brown et al. |
| 4,503,054 A | 3/1985 | Brown et al. |
| 4,584,298 A | 4/1986 | Brown et al. |
| 4,616,015 A | 10/1986 | Teraji et al. |
| 4,624,951 A | 11/1986 | Goschke |
| 4,629,789 A | 12/1986 | Gainer et al. |
| 4,694,005 A | 9/1987 | Brown et al. |
| 4,906,628 A | 3/1990 | Coates |
| 4,933,336 A | 6/1990 | Martin et al. |
| 5,552,409 A | 9/1996 | Michelotti et al. |
| 8,501,731 B2 * | 8/2013 | Hu ................... C07D 401/10 514/217.05 |
| 9,212,146 B2 * | 12/2015 | Hu ................... A61K 31/501 |
| 9,549,932 B2 | 1/2017 | Wortmann et al. |
| 10,287,353 B2 | 5/2019 | Bissonnette et al. |

(Continued)

FOREIGN PATENT DOCUMENTS

| | | |
|---|---|---|
| DE | 19929787 A1 | 1/2001 |
| EP | 0052442 A1 | 5/1982 |

(Continued)

OTHER PUBLICATIONS

WO2009114993—Abstract, casreact abstract of WO 2009114993, 2009.*
Maurice et al., "Advances in targeting cyclic nucleotide phosphodiesterases," Nature Reviews Drug Discovery, 2014, vol. 13, Iss. 4, pp. 290-314.
Movsesian et al., "Phosphodiesterase Inhibition in Heart Failure," Phosphodiesterases as Drug Targets, Handbook of Experimental Pharmacology, 2011, vol. 204, pp. 237-249.

(Continued)

*Primary Examiner* — Sun Jae Yoo
(74) *Attorney, Agent, or Firm* — Melissa Hunter-Ensor; Scott Goncher; Greenberg Traurig, LLP

(57) ABSTRACT

The present invention provides 6-phenyl-4,5-dihydropyridazin-3(2H)-one derivatives of formula (I): The present invention provides 6-phenyl-4,5-dihydropyridazin-3(2H)-one derivatives of formula (I):

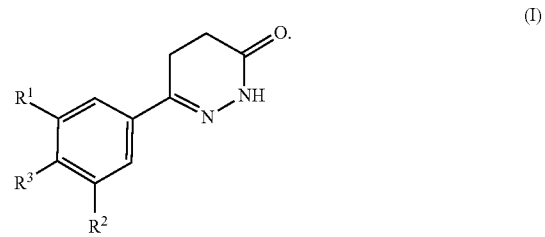

(I)

3 Claims, No Drawings

(56) References Cited

U.S. PATENT DOCUMENTS

| | | |
|---|---|---|
| 10,385,131 B2 | 8/2019 | Bissonnette et al. |
| 10,729,680 B2 | 8/2020 | Lücking et al. |
| 11,427,553 B2 | 8/2022 | Ellermann et al. |
| 2016/0287604 A1 | 10/2016 | Wortmann et al. |
| 2020/0369633 A1 | 11/2020 | Ellermann et al. |
| 2021/0353630 A1 | 11/2021 | Gradl et al. |
| 2021/0371935 A1 | 12/2021 | Wu et al. |
| 2022/0396554 A1 | 12/2022 | Ellermann et al. |
| 2023/0017200 A1 | 1/2023 | Ellermann et al. |

FOREIGN PATENT DOCUMENTS

| | | |
|---|---|---|
| EP | 0059688 A1 | 9/1982 |
| EP | 0080296 A1 | 6/1983 |
| EP | 0086301 A1 | 8/1983 |
| EP | 0122494 A2 | 10/1984 |
| EP | 0122627 A2 | 10/1984 |
| EP | 0123254 A1 | 10/1984 |
| EP | 0175363 A2 | 3/1986 |
| EP | 0220044 A2 | 4/1987 |
| EP | 0478195 A1 | 4/1992 |
| EP | 2253625 A1 | 11/2010 |
| EP | 2281822 A1 | 2/2011 |
| JP | H05148250 A | 6/1993 |
| JP | H07291968 A | 11/1995 |
| TW | 201613920 A | 4/2016 |
| WO | 199401412 A1 | 1/1994 |
| WO | 2002072103 A1 | 9/2002 |
| WO | 2008108602 A1 | 9/2008 |
| WO | 2009114993 A1 | 9/2009 |
| WO | 2010121022 A1 | 10/2010 |
| WO | 2011138427 A2 | 11/2011 |
| WO | 2012161812 A1 | 11/2012 |
| WO | 2014164704 A2 | 10/2014 |
| WO | 2016020320 A1 | 2/2016 |
| WO | 2017027854 A1 | 2/2017 |
| WO | 2017134231 A1 | 8/2017 |
| WO | 2020157194 A1 | 8/2020 |

OTHER PUBLICATIONS

Goeschke et al., "6-(4-Morpholino-phenyl)-4,5-dihydro-2H-pyridazine-3-ones: potent platelet aggregation inhibitors and antithrombotics," European Journal of Medicinal Chemistry, Oct. 1991; vol. 26, No. 7, pp. 715-721.

Steck et al., "Pyridazines. VI. Some 6-Substituted 3(2H)pyridazinones," Journal of Heterocyclic Chemistry, Oct. 1974; vol. 11, No. 5, pp. 755-761.

International Search Report and Written Opinion in corresponding PCT Patent Application No. PCT/EP2018/071016, dated Nov. 14, 2018 (15 pages).

Forest et al., "A novel class of cardiotonic agents: synthesis and biological evaluation of 5-substituted 3,6-dihydrothiadiazin-2-ones with cyclic AMP phosphodiesterase inhibiting and myofibrillar calcium sensitizing properties," Journal of Medicinal Chemistry, 1992, vol. 35, No. 1, pp. 163-172.

Hurd et al., "On Acylhydrazones and 1,2,3-Thiadiazoles," Journal of the American Chemical Society, 1955, vol. 77, No. 20, pp. 5359-5364.

James, Christopher W., "Anagrelide-Induced Cardiomyopathy," Pharmacotherapy, 2012, vol. 20, No. 10, pp. 1224-1227.

Packer et al., "Effect of Oral Milrinone on Mortality in Severe Chronic Heart Failure," The New England Journal of Medicine, Nov. 21, 1991, vol. 325, pp. 1468-1475.

Page Il et al., "Drugs That May Cause or Exacerbate Heart Failure," Circulation, 2016, vol. 134, No. 6, pp. e32-e69.

Rosenblum et al., "Synthesis of Dihydrooxadiazinones and Study of Geometrical Isomerism in α-Ketol Carbethoxyhydrazones," Journal of the American Chemical Society, 1963, vol. 85, No. 23, pp. 3874-3878.

Rosenblum et al., "The Chemistry of 1,3,4-Oxadiazin-2-ones. Preparation and Thermal Stability," Journal of the American Chemical Society, 1965, 87, No. 24, pp. 5716-5719.

Rosenblum et al., "Thermal Decomposition of 2,3-Dihydro-5,6-Diphenyl-1,3,-4,6-Oxadiazin-2-one," The Society of Chemical Industry, Dec. 15, 1956, pp. 1480-1481.

Savai et al., "Targeting cancer with phosphodiesterase inhibitors," Expert Opinion on Investigational Drugs, 2010, vol. 19, No. 1, pp. 117-131.

Matthews et al., "Dominant-Negative Activator Protein 1 (TAM67) Targets Cyclooxygenase-2 and Osteopontin under Conditions in which it Specifically Inhibits Tumorigenesis," Cancer Research, Mar. 15, 2007, vol. 67, No. 6, pp. 2430-2438.

King, Frank D., "Bioisosteres, Conformational Restriction, and Pro-drugs—Case History: An Example of a Conformational Restriction Approach," Medical Chemistry: Principles and Practice, 1994, Chapter 14, pp. 206-208.

\* cited by examiner

6-PHENYL-4,5-DIHYDROPYRIDAZIN-3(2H)-ONE DERIVATIVES AS PDE3A AND PDE3B INHIBITORS FOR TREATING CANCER

This application is the U.S. national phase application, pursuant to 35 U.S.C. § 371, of PCT International Application Serial No.: PCT/EP2018/071016, filed Aug. 2, 2018, which claims the benefit of and priority to U.S. Provisional Application No. 62/541,631, filed Aug. 4, 2017, the entire contents of which are incorporated herein by reference.

The present invention provides dihydropyridazinone compounds of general formula (I) as described and defined herein, methods of preparing said compounds, pharmaceutical compositions and the use of said compounds for the treatment or prophylaxis of diseases, in particular of hyperproliferative diseases.

BACKGROUND

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by predictive chemogenomics to identify the cell features associated with drug response. In the 1990s, Weinstein and colleagues demonstrated that the cytotoxic profile of a compound can be used to identify cellular characteristics, such as gene-expression profiles and DNA copy number, which correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small molecule sensitivity can be linked to expression patterns or somatic alterations, as in the case of trastuzumab-sensitive HER2-amplified breast cancer or erlotinib-sensitive EGFR-mutant lung cancer.

Phenotypic screening identified some compounds known in the literature to be PDE3 inhibitors to be useful for the treatment of certain cancers. Co-expression of PDE3A and/or PDE3B and Schlafen 12 (SLFN12) polynucleotides or polypeptides are typically required for cells to be sensitive. PDE3A/B inhibitors which cause drug sensitivity have been found to stabilze the formation of a complex between PDE3A or PDE3B and SLFN12. PDE3A/B inhibitors which do not cause cell sensitivity typically do not stabilize PDE3A- or PDE3B-SLFN12 complex.

Several PDE-3 inhibitors such as milrinone, cilostazol, and levosimendan have been approved for clinical treatment of cardiovascular indications or thrombocythemia (anagrelide), but not for cancer indication. The most recent quality review of PDE inhibitors (Nature Reviews Drug Discovery 13, 290-314, (2014)) barely mentions cancer. From WO 2014/164704, WO2017/027854, and WO2017/134231 some PDE3 inhibitors are known.

Especially the cardiac mode of action mediated unwanted effects of PDE-3 inhibitors (Movsesian & Kukreja, S. H. Francis et al. (eds.), Phosphodiesterases as Drug Targets, Handbook of Experimental Pharmacology 204, 2011; p 237ff) may limit their therapeutic use when PDE3-inhibiting agents are used on a short- or/and long term basis, e.g. in cancer patients and a suitable therapeutic window is needed.

However, the state of the art does not describe dihydropyridazinone compounds of general formula (I) of the present invention as described and defined herein. Moreover the art is teaching away from pyridazinone compounds lacking the methyl group of the pyridazinone ring which always is present in the prepublished compounds.

SUMMARY

It has now been found, and this constitutes the basis of the present invention, that the compounds of the present invention have surprising and advantageous properties.

In particular, the compounds of the present invention have surprisingly been found to effectively inhibit tumor cell proliferation with IC50 values of <100 nM in e.g. HeLa cells while IC50 values for enzymatic PDE3 inhibition are often >2.5 times higher than $IC_{50}$ values for tumor cell proliferation, which is deemed to be associated with PDE3A-SLFN12 complex induction and/or improved pharmacokinetic parameters in vitro or in vivo and/or improved PhysChem properties and/or improved safety pharmacological properties and may therefore be used for the treatment or prophylaxis of hyperproliferative diseases, such as cancer diseases, for example.

The present invention provides compounds of general formula (I) which modulate PDE3A- and/or PDE3B-SLFN12 complex, methods for their preparation, pharmaceutical composition and the use thereof and methods of treatment or prophylaxis of diseases, in particular of hyperproliferative diseases more particularly of cancer diseases. These and other features of the present teachings are set forth herein.

In accordance with a first aspect, the present invention provides compounds of general formula (I):

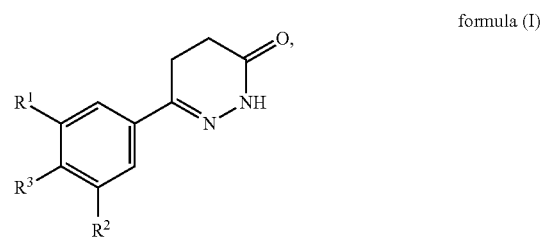

formula (I)

where
$R^1$ is selected from a hydrogen atom, a halogen atom, a cyano group, a $C_1$-$C_3$-alkyl group, a $C_1$-$C_3$-haloalkyl group, a $C_1$-$C_3$-haloalkoxy group;
$R^2$ is selected from a hydrogen atom and a halogen atom;
$R^3$ is selected from,
 a $C_1$-$C_6$-alkoxy group,
 a $C_2$-$C_6$-alkenyl group,
 a $C_3$-$C_6$-cycloalkyl group,
 a $C_5$-$C_6$-cycloalkenyl group,
 a 3-7-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^4$R$^5$ group, and a NR$^6$R$^7$ group, with the proviso that R$^3$ can not be imidazol-1-yl if R$^1$ and R$^2$ both are hydrogen atoms and R$^3$ can not be morpholin-4-yl, if R$^1$ is trifluoromethyl and R$^2$ is a hydrogen atom;

R$^4$/R$^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered-heterocycloalkyl group;

R$^6$/R$^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-NR$^8$—$C_1$-$C_5$-alkyl group, a —$C_1$-$C_5$-hydroxyalkylen-($C_1$-$C_3$-haloalkyl) group, a $C_3$-$C_6$-cycloalkyl group, and a 3- to 5-membered-heterocycloalkyl group, or R$^6$ and R$^7$ together form a 3-, 4-, 5-, 6- or 7-membered ring optionally containing one or two additional heteroatoms selected from the group consisting of —O—, —S— and —NR$^8$—, and which is optionally substituted one, two, or three times with a substituent selected from a halogen atom, a hydroxy group, and a $C_1$-$C_3$-alkyl group and if R$^6$ and R$^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;

R$^8$ is a hydrogen atom or a $C_1$-$C_3$-alkyl group;

or a stereoisomer, a tautomer, an N-oxide, a hydrate, a solvate, or a salt thereof, or a mixture of same.

The compounds are suitable for the treatment of a patient having a cancer that is sensitive to treatment with a phosphodiesterase 3A/B (PDE3A/B)-SLFN12 complex modulator by detecting co-expression of PDE3A and/or PDE3B and Schlafen 12 (SLFN12) and/or SLFN12L mRNA, polynucleotides or polypeptides and/or a lack of decrease in expression of CREB3L1 mRNA, polynucleotides or polypeptides in a cancer cell derived from such patients.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Structures drawn include all permissible rotations about bonds.

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, in particular 1, or 2.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkyl)-O—($C_1$-$C_4$-alkyl)-, a hyphen at the beginning or at the end of such a composite substituent indicates the point of attachment of said composite substituent to the rest of the molecule. Should the composite substituent be substituted said substitutent may be bound at any suitable carbon atom of the composite substitutent.

Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "alkylene" derives from the term "alkyl" as being a bivalent constituent named by addition of "ene" to the term "alkyl" e.g. "methyl" becomes "methylene" meaning a "—$CH_2$—" constituent whereby the open bonds of branched constituents are located at the respective ends of the longest chain.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_6$-hydroxyalkyl" means a linear or branched, saturated, monovalent hydrocarbon group in which the term "$C_1$-$C_6$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

The term "$C_2$-$C_6$-alkenyl" means a linear or branched, monovalent hydrocarbon group, which contains one or two double bonds, and which has 2, 3, 4, 5 or 6 carbon atoms, particularly 2 or 4 carbon atoms ("$C_2$-$C_4$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. Particularly, said group is vinyl or allyl, propenyl-, isopropenyl-, butenyl-, or isobutenyl group.

The term "$C_3$-$C_8$-cycloalkyl" means a saturated, monovalent, mono- or bicyclic hydrocarbon ring which contains 3, 4, 5, or 6 carbon atoms ("$C_3$-$C_6$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl.

The term "$C_4$-$C_8$-cycloalkenyl" means a monovalent, mono- or bicyclic hydrocarbon ring which contains 5, or 6, carbon atoms and one double bond. Particularly, said ring contains 5 or 6 carbon atoms ("$C_5$-$C_6$-cycloalkenyl"). Said $C_5$-$C_6$-cycloalkenyl group is for example, a monocyclic hydrocarbon ring, e.g. cyclopentenyl, cyclohexenyl or cyclohexadienyl.

The terms "3- to 7-membered heterocycloalkyl" and "3- to 6-membered heterocycloalkyl" mean a monocyclic, saturated heterocycle with 3, 4, 5, 6 or 7 or, respectively, 3, 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 3- or 4-membered ring, such as azacyclopropyl, oxacyclopropyl, azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example and said heterocycloalkyl group may be a fused or bridged heterocycloalkyl group.

Particularly, the term "4- to 6-membered heterocycloalkyl" means a 4- to 6-membered heterocycloalkyl as defined supra containing one ring nitrogen atom, an oxygen atom or a sulfur atom and if the ring contains one nitrogen atom said ring optionally contains one further ring heteroatoms from the series: N, O, S. More particularly, "5- or 6-membered heterocycloalkyl" means a monocyclic, saturated heterocycle with 5 or 6 ring atoms in total, containing one ring nitrogen atom and optionally one further ring heteroatom from the series: N, O, S. Said heterocycloalkyl group is being attached to the rest of the molecule via any carbon atom or where applicable via any nitrogen atom.

The term "5- to 6-membered heterocycloalkyl which is partially unsaturated" or a "heterocycloalkenyl" means a monocyclic, unsaturated, non-aromatic heterocycle with 5 or 6, ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom. The term "partially unsaturated heterocycloalkane", as used herein, refers to a compound consisting of a partially unsaturated heterocycloalkyl group as defined herein, and a hydrogen atom to which said partially unsaturated heterocycloalkyl group is bonded with its one valency.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "fused heterocycloalkyl" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.1.0]hexyl, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl.

The term "bridged heterocycloalkyl" means a bicyclic, saturated heterocycle with 7, 8, 9 or 10 atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[3.1.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl, whereby the position of the heteroatom is intended to be included at any suitable position as well as its connective atom to the rest of the molecule.

The term "aryl" refers to an aromatic monocyclic, bicyclic (2 fused rings), tricyclic (3 fused rings), or polycyclic (two or more fused rings) hydrocarbon ring system having 6 to 20 (e.g. 6 to 10 ring carbon atoms). Nonlimiting examples of aryl groups include phenyl, or napthyl (e.g., 1-napthyl, 2-napthyl, etc.), particularly phenyl. The aryl group may optionally be substituted one, two, three or four times.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency) to the rest of the molecule.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl, especially pyridinyl, pyrimidinyl, furanyl and pyrazolyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a 2H-pyrrol-1-yl group, which is optionally substituted with one or two substituents and each substituent is independently selected from a hydrogen atom, a cyano group and a methyl group,
  a 1H-pyrazol-4-yl group, which is optionally substituted with a methyl group,
  a 1H-pyrazol-5-yl group, which is optionally substituted with a methyl group,
  a furan-3-yl group,
  a 1,2-thiazol-4-yl group which is optionally substituted with a methyl group,
  a 1,3-thiazol-5-yl group which is optionally substituted with a methyl groups,
  a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group,
  a pyrimidin-5-yl group, which is optionally substituted with a methyl group or an amino group,
  a 1H-indol-6-yl group, a 1H-indol-4-yl group,
  a 1H-indazol-6-yl group,
  a 1H-benzimidazol-6-yl group,
  more particularly the heteroaryl group is al H-pyrazol-4-yl group, which is optionally substituted with a methyl group, a furan-3-yl group, a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group,
  a pyrimidin-5-yl group, which is optionally substituted with a methyl group, an amino group, a 1H-indol-6-yl group and a 1H-indol-4-yl group, Particularly, the heteroaryl group is a 2H-pyrrol-1-yl group, which is optionally substituted with one or two substituents and each substituent is independently selected from a hydrogen atom, a cyano group and a methyl group,
  a 1H-pyrazol-4-yl group, which is optionally substituted with a methyl group, a fluorine atom or a difluoromethyl group
  a 1H-pyrazol-5-yl group, which is optionally substituted with a methyl group a fluorine atom or a difluoromethyl group,
  a furan-3-yl group,
  a 1,2-thiazol-4-yl group which is optionally substituted with a methyl group, a 1,3-thiazol-5-yl group which is optionally substituted with a methyl group, a furanyl group, a pyridin-2-yl a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group, a pyrimidin-5-yl group, which is optionally substituted with a methyl group or an amino group, a 1H-indol-6-yl group, a 1H-indol-4-yl group which are optionally substituted with a fluorine atom, a chlorine atom, a methyl group, a difluoromethyl group, a trifluoromethyl group, a methoxy group or a amino group, a 1H-indazol-6-yl group, a 1H-benzimidazol-6-yl group, more particularly the heteroaryl group is al H-pyrazol-4-yl group, which is optionally substituted with a methyl group, a furan-3-yl group, a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group, a pyrimidin-5-yl group, which is optionally substituted with a methyl group, an amino group, a 1H-indol-6-yl group and a 1H-indol-4-yl group.

The term "$C_1$-$C_6$", as used in the present text, e.g. in the context of the definition of "$C_1$-$C_6$-alkyl", "$C_1$-$C_6$-haloalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_5$, $C_8$-$C_{10}$, $C_8$-$C_9$ and $C_9$-$C_{10}$.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In particular embodiments, the analyte is a PDE3A or SLFN12 polypeptide.

By "disease" is meant any condition or disease that damages or interferes with the normal function of a cell, tissue, or organ. Examples of diseases include hyperproliferatiotive disorder, cancer types such as e.g., adenocarcinoma, breast cancer, cervical cancer, liver cancer, lung cancer and melanoma.

By "effective amount" is meant the amount of a compound described herein required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

In still other embodiments, the PDE3A- or PDE3B-SLFN12 complex modulator is a compound of formula (I).

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

Unless specifically stated or obvious from context, as used herein, the term "or" is understood to be inclusive. Unless specifically stated or obvious from context, as used herein, the terms "a", "an", and "the" are understood to be singular or plural.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The term "prodrugs" or "prodrug" designates compounds which themselves can be biologically active or inactive, but are converted (for example metabolically or hydrolytically) into compounds according to the invention during their residence time in the body. Derivatives of the compound 6 and the salts thereof which are converted into compound 6 or a salt thereof in a biological system (bioprecursors or pro-drugs) are covered by the invention. Said biological system may be, for example, a mammalian organism, particularly a human subject. The bioprecursor is, for example, converted into a compound of formula (I) or a salt thereof by metabolic processes.

Unless specifically stated or obvious from context, as used herein, if a range is provided, the upper and lower limit are always meant to be included. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reference" is meant a standard or control condition.

The recitation of a listing of chemical groups in any definition of a variable herein includes definitions of that variable as any single group or combination of listed groups.

The recitation of an embodiment for a variable or aspect herein includes that embodiment as any single embodiment or in combination with any other embodiments or portions thereof.

DETAILED DESCRIPTION

As a first aspect the invention provides compounds of formula (I)

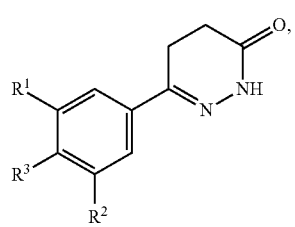

formula (I)

where
R$^1$ is selected from a hydrogen atom, a halogen atom, a cyano group, a C$_1$-C$_3$-alkyl group, a C$_1$-C$_3$-haloalkyl group, a C$_1$-C$_3$-haloalkoxy group;
R$^2$ is selected from a hydrogen atom and a halogen atom;
R$^3$ is selected from,
  a C$_1$-C$_6$-alkoxy group,
  a C$_2$-C$_6$-alkenyl group,
  a C$_3$-C$_6$-cycloalkyl group,
  a C$_5$-C$_6$-cycloalkenyl group,
  a 3- to 7-membered heterocycloalkyl group, which is optionally substituted with one, two or three substituents and each substituent is independently selected from a halogen atom, a C$_1$-C$_3$-alkyl group, a hydroxy group, NR$^4$R$^5$ group, a C$_1$-C$_3$-haloalkyl group and a C$_1$-C$_3$-haloalkoxy group,
  a 5- to 7-membered heterocycloalkyl group which is partially unsaturated and optionally substituted with one, two or three substituents and each substituent is independently selected from an oxo group (=O), a C$_1$-C$_3$-alkyl group and a halogen atom,
  an aryl group which is optionally substituted with one, two, three or four substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, a —C(O)NR$^4$R$^5$ group and a NR$^4$R$^5$ group,
  a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, a hydroxy group, and a NR$^4$R$^5$ group,
  and a NR$^6$R$^7$ group,
  with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
R$^4$/R$^5$ is independently selected from a hydrogen atom, a C$_1$-C$_6$-alkyl group, a —C$_1$-C$_5$-alkylen-O—C$_1$-C$_5$-alkyl group, a —C$_1$-C$_5$-alkylen-S—C$_1$-C$_5$-alkyl group, C$_3$-C$_6$-cycloalkyl group, and a 3- to 5-membered heterocycloalkyl group;
R$^6$/R$^7$ is independently selected from a hydrogen atom, a C$_1$-C$_6$-alkyl group, a —C$_1$-C$_5$-alkylen-O—C$_1$-C$_5$-alkyl group, a —C$_1$-C$_5$-alkylen-S—C$_1$-C$_5$-alkyl group, a —C$_1$-C$_5$-alkylen-NR$^8$—C$_1$-C$_5$-alkyl group, a —C$_1$-C$_5$-hydroxyalkylen-(C$_1$-C$_3$-haloalkyl) group, a C$_3$-C$_6$-cycloalkyl group, and a 3- to 5-membered heterocycloalkyl group,
or R$^6$ and R$^7$ together form a 3-, 4-, 5-, 6- or 7-membered ring optionally containing one or two additional heteroatoms selected from the group consisting of —O—, —S— and —NR$^8$—,
and which is optionally substituted one, two, or three times with a substituent selected from a halogen atom, a hydroxy group, and a C$_1$-C$_3$-alkyl group
and if R$^6$ and R$^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
R$^8$ is a hydrogen atom or a C$_1$-C$_3$-alkyl group;
or a stereoisomer, a tautomer, an N-oxide, a hydrate, a solvate or a salt thereof, or a mixture of same.

As an embodiment of the first aspect the invention provides compounds of formula (I), where $R^1$ is selected from a hydrogen atom, a halogen atom, and a cyano group, a $C_1$-$C_3$-alkyl group, a $C_1$-$C_3$-haloalkyl group, a $C_1$-$C_3$-haloalkoxy group;

$R^2$ is selected from a hydrogen atom and a halogen atom, $R^3$ is selected from a halogen atom, a $C_1$-$C_6$-alkoxy group, a $C_2$-$C_6$-alkenyl group, a $C_3$-$C_6$-cycloalkyl group, a $C_5$-$C_6$-cycloalkenyl group, a 3- to 7-membered heterocycloalkyl group, which is optionally substituted with one, two, or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;

a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;

and a $NR^6R^7$ group, with the proviso that $R^3$ can not be imidazol-1-yl if $R^1$ and $R^2$ are a hydrogen atoms:

$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;

$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a $C_3$-$C_6$-cycloalkyl group, and a 3- to 5-membered heterocycloalkyl group, or $R^6$ and $R^7$ together form a 3-, 4-, 5-, 6- or 7-membered ring optionally containing one or two additional heteroatoms selected from the group consisting of —O—, —S— and —$NR^8$—, and which is optionally substituted one, two or three times with a substituent selected from a halogen atom, a hydroxy group and a $C_1$-$C_3$-alkyl group;

and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group, or a stereoisomer, a tautomer, an N-oxide, a hydrate, a solvate, or a salt thereof, or a mixture of same.

As an embodiment of the first aspect the invention provides compounds of formula (I), where $R^1$ is selected from a hydrogen atom, a halogen atom, and a cyano group, a $C_1$-$C_3$-alkyl group, a $C_1$-$C_3$-haloalkyl group, a $C_1$-$C_3$-haloalkoxy group;

$R^2$ is selected from a hydrogen atom and a halogen atom, $R^3$ is selected from, a $C_1$-$C_6$-alkoxy group, a $C_2$-$C_6$-alkenyl group, a $C_3$-$C_6$-cycloalkyl group, a $C_5$-$C_6$-cycloalkenyl group, a 3- to 7-membered heterocycloalkyl group, which is optionally substituted with one, two, or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;

a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;

and a $NR^6R^7$ group, with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom, $R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;

$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a $C_3$-$C_6$-cycloalkyl group, and a 3- to 5-membered heterocycloalkyl group, or $R^6$ and $R^7$ together form a 3-, 4-, 5-, 6- or 7-membered ring optionally containing one or two additional heteroatoms selected from the group consisting of —O—, —S— and —$NR^8$—, and which is optionally substituted one, two or three times with a substituent selected from a halogen atom, a hydroxy group and a $C_1$-$C_3$-alkyl group;

and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group, or a stereoisomer, a tautomer, an N-oxide, a hydrate, a solvate, or a salt thereof, or a mixture of same.

The invention is further based at least in part on the discovery that the compounds of formula (I) are PDE3A- or PDE3B-SLFN12 complex modulators.

Accordingly, in a further embodiment the invention further provides methods of selecting a subject as having a cancer that responds to a PDE3A- or PDE3B-SLFN12 complex modulator, especially a compound of formula (I), where the selection method involves detecting co-expression of PDE3A and/or PDE3B and Schlafen 12 (SLFN12) polypeptides or polynucleotides, in a cancer cell derived from such subjects.

In a further embodiment, the invention provides methods of determining that the expression of CREB3L1 or SLFN12 polynucleotide or polypeptide is reduced or is undetectable in a cancer cell that has acquired resistance to a PDE3A- and/or PDE3B-SLFN12 complex modulator in order to prevent ineffective treatment with a compound of formula (I).

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide.

Accordingly, the invention provides methods comprising the steps of
 identifying subjects that have a malignancy that is likely to respond to PDE3A- and/or PDE3B-SLFN12 complex modulator treatment, especially a treatment with a compound of formula (I), based on the level of PDE3A/PDE3B and SLFN12 expression in a subject biological sample comprising a cancer cell
 administering an effective amount of a compound of formula (I).

In particular embodiments, the invention provides methods comprising the steps of
 identifying subjects that have a malignancy that is resistant to PDE3A- and/or PDE3B-SLFN12 complex modulator treatment, especially to the treatment of a compound of formula (I), based on a loss or reduction in the level of CREB3L1 or SLFN12 expression relative to a reference and
 subsequently excluding them from an envisaged treatment schedule with a compound of formula (I).

Compound Forms and Salts

It is possible for the compounds of formula (I) to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

The term "pharmaceutically acceptable salt(s)" of the compounds of formula (I) include those derived from pharmaceutically acceptable inorganic and organic acids and bases. For example, see S. M. Berge, et al. "Pharmaceutical Salts," J. Pharm. Sci. 1977, 66, 1-19.

As used herein, the term "pharmaceutically acceptable salt" refers to a salt formed by the addition of a pharmaceutically acceptable acid or base to a compound disclosed herein.

As used herein, the phrase "pharmaceutically acceptable" refers to a substance that is acceptable for use in pharmaceutical applications from a toxicological perspective and does not adversely interact with the active ingredient.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts.

Further, another suitably pharmaceutically acceptable salt of a compound of formula (I), which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dim ethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

In certain embodiments salts are derived from appropriate bases include alkali metal (e.g., sodium), alkaline earth metal (e.g., magnesium), ammonium and N-(alkyl)₄ salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF₃COOH", "x Na+", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention. particularly deuterium-containing compounds of formula (I).

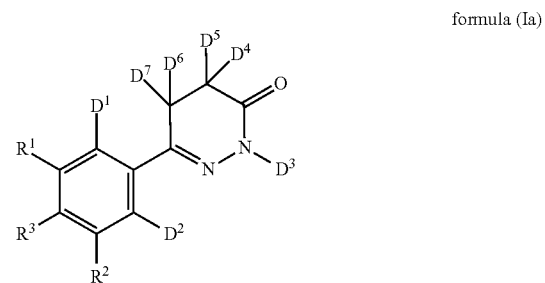

formula (Ia)

Formula shows the positions $D^1$, $D^2$, $D^3$, $D^4$, $D^5$, $D^6$, and $D^7$ in which anyone of the hydrogen atoms may be exchanged by a deuterium atom. Additionally in residues $R^1$-$R^4$ if these residues contain a heteroatom-H or carbon-H bond accessible for a chemical reaction such an exchange may be possible. Hydrogen atoms can be replaced by deuterium atoms using methods known to those with ordinary skill in the art to obtain a heteroatom-D or carbon-D bond. Anyone of $R^1$, $R^2$, or $R^4$ themselves can also be deuterium instead of hydrogen.

Thus one aspect of the invention are those compounds wherein independently anyone of $R^1$, $R^2$, or $R^4$ is deuterium and/or anyone of the hydrogen atoms as shown in formula (I) are replaced by a deuterium atom and or anyone of $R^1$, $R^2$, $R^3$, or $R^4$ bears a deuterium atom at a chemically accessible position or any combination of positions being deuterated at the same time.

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the diseases specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a direct route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome P$_{450}$.

In some aspects, the compounds of formula (I) may be isomers. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention The symbol ⚌ denotes a bond that can be a single or a double bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The compounds of the present invention optionally contain one or more asymmetric centres, depending upon the location and nature of the various substituents desired, which are e.g. carbon atoms having four different substituents. It is possible that one or more asymmetric carbon atoms are present in the (R) or (S) configuration, which can result in racemic mixtures in the case of a single asymmetric centre, and in diastereomeric mixtures in the case of multiple asymmetric centres. The term "(±)" is used to designate a racemic mixture where appropriate. In certain instances, it is possible that asymmetry also be present due to restricted rotation about a given bond, for example, the central bond adjoining two substituted aromatic rings of the specified compounds. When a compound is an enantiomer, the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Preferred compounds are those which produce the more desirable biological activity. These separated, pure or partially purified isomers or racemic mixtures of the compounds of this invention are also included within the scope of the present invention. The purification and the separation of such materials can be accomplished by standard techniques known in the art including chiral high pressure liquid chromatography (HPLC), the formation and crystallization of chiral salts, or prepared by asymmetric syntheses.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Preferred is the stereoisomer which shows the desired effect. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

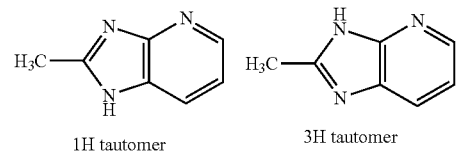

1H tautomer      3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

Thus the present invention includes prodrugs of the compounds of formula (I).

In yet another embodiment the present invention includes stereoisomers, tautomers, an N-oxides, hydrates, solvates, or a salts, or a mixture of same of a compounds of formula (I).

In another embodiment the present invention includes stereoisomers, tautomers, hydrates, solvates, or a salts, or a mixture of same of a compounds of formula (I).

In a further embodiment the present invention includes stereoisomers, tautomers, solvates, or a salts, or a mixture of same of a compounds of formula (I).

In yet a further embodiment the present invention includes stereoisomers, tautomers, solvates, or a salts, or a mixture of same of a compounds of formula (I).

In yet another embodiment the present invention includes stereoisomers, tautomers, or a salts, or a mixture of same of a compounds of formula (I).

Further Aspects and Embodiments

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_2$-$C_3$-haloalkyl group, a $C_1$-$C_3$-haloalkoxy group;
$R^2$ is selected from a hydrogen atom and a halogen atom;
$R^3$ is selected from,
 a $C_1$-$C_6$-alkoxy group,
 a $C_2$-$C_6$-alkenyl group,
 a $C_3$-$C_6$-cycloalkyl group,
 a $C_5$-$C_6$-cycloalkenyl group,
 a 3- to 7-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group,
 a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom,
 an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
 a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^4$R$^5$ group,
 and a NR$^6$R$^7$ group,
 with the proviso that R$^3$ can not be imidazol-1-yl if R$^1$ and R$^2$ are a hydrogen atoms;
$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-NR$^8$—$C_1$-$C_5$-alkyl group, a —$C_1$-$C_5$-hydroxyalkylen-($C_1$-$C_3$-haloalkyl) group, a $C_3$-$C_6$-cycloalkyl group, and a 3- to 5-membered heterocycloalkyl group,
or R$^6$ and R$^7$ together form a 3-, 4-, 5-, 6- or 7-membered ring optionally containing one or two additional heteroatoms selected from the group consisting of —O—, —S— and —NR$^8$—,
 and which is optionally substituted one, two, or three times with a substituent selected from a halogen atom, a hydroxy group, and a $C_1$-$C_3$-alkyl group
 and if R$^6$ and R$^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_1$-$C_3$-haloalkyl group, a $C_1$-$C_3$-haloalkoxy group;
$R^2$ is selected from a hydrogen atom and a halogen atom;
$R^3$ is selected from,
 a $C_1$-$C_6$-alkoxy group,
 a $C_2$-$C_6$-alkenyl group,
 a $C_4$-$C_6$-cycloalkyl group,
 a $C_5$-$C_6$-cycloalkenyl group,
 a 4- to 6-membered heterocycloalkyl group, which is optionally substituted with one, two or three substituents and each substituent is independently selected from a halogen atom, a $C_1$-$C_3$-alkyl group, a hydroxy group, NR$^4$R$^5$ group, a $C_1$-$C_3$-haloalkyl group and a $C_1$-$C_3$-haloalkoxy group,
 a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom,
 an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
 a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^4$R$^5$ group,
 and a NR$^6$R$^7$ group,
 with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6/R^7$ is independently selected from a hydrogen atom, a $C_2$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-

$C_5$-alkylen-$NR^8$—$C_1$-$C_5$-alkyl group, a —$C_1$-$C_5$-hydroxyalkylen-($C_1$-$C_3$-haloalkyl) group, a $C_4$-$C_6$-cycloalkyl group, and a 3- to 5-membered heterocycloalkyl group, or $R^6$ and $R^7$ together form a 3-, 4-, 5-, 6- or 7-membered ring optionally containing one or two additional heteroatoms selected from the group consisting of —O—, —S— and —$NR^8$—, and which is optionally substituted one, two, or three times with a substituent selected from a halogen atom, a hydroxy group, and a $C_1$-$C_3$-alkyl group and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;

or a stereoisomer, a tautomer, an N-oxide, a hydrate, a solvate, or a salt thereof, or a mixture of same.

In accordance with an embodiment of the first aspect, the present invention provides compounds of general formula (I):

$R^1$ is selected from a hydrogen atom, a halogen atom, a cyano group, a $C_1$-$C_3$-alkyl group, a $C_2$-$C_3$-haloalkyl group, a $C_1$-$C_3$-haloalkoxy group;

$R^2$ is selected from a hydrogen atom and a halogen atom;

$R^3$ is selected from,
- a $C_1$-$C_6$-alkoxy group,
- a $C_2$-$C_6$-alkenyl group,
- a $C_4$-$C_6$-cycloalkyl group,
- a $C_5$-$C_6$-cycloalkenyl group,
- a 4- to 6-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group,
- a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom,
- an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group,
- and a $NR^6R^7$ group, with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;

$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;

$R^6/R^7$ is independently selected from a hydrogen atom, a $C_2$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a —$C_1$-$C_5$-hydroxyalkylen-($C_1$-$C_3$-haloalkyl) group, a $C_4$-$C_6$-cycloalkyl group, and a 3- to 5-membered heterocycloalkyl group, or $R^6$ and $R^7$ together form a 3-, 4-, 5-, 6- or 7-membered ring optionally containing one or two additional heteroatoms selected from the group consisting of —O—, —S— and —$NR^8$—,
and which is optionally substituted one, two, or three times with a substituent selected from a halogen atom, a hydroxy group, and a $C_1$-$C_3$-alkyl group
and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_2$-$C_3$-haloalkyl group, a $C_1$-$C_3$-haloalkoxy group;
$R^2$ is selected from a hydrogen atom and a halogen atom;
$R^3$ is selected from,
  a $C_1$-$C_6$-alkoxy group,
  a $C_2$-$C_6$-alkenyl group,
  a $C_4$-$C_6$-cycloalkyl group,
  a $C_5$-$C_6$-cycloalkenyl group,
  a 4- to 6-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group,
  a 5- to 7-membered heterocycloalkyl group which is partially unsaturated and optionally substituted with one, two or three substituents and each substituent is independently selected from an oxo group (═O), a $C_1$-$C_3$-alkyl group and a halogen atom,
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group,
  and a $NR^6R^7$ group,
with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4$/$R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6$/$R^7$ is independently selected from a hydrogen atom, a $C_2$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a —$C_1$-$C_5$-hydroxyalkylen-($C_1$-$C_3$-haloalkyl) group, a $C_4$-$C_6$-cycloalkyl group, and a 3- to 5-membered heterocycloalkyl group,
or $R^6$ and $R^7$ together form a 3-, 4-, 5-, 6- or 7-membered ring optionally containing one or two additional heteroatoms selected from the group consisting of —O—, —S— and —$NR^8$—,
and which is optionally substituted one, two, or three times with a substituent selected from a halogen atom, a hydroxy group, and a $C_1$-$C_3$-alkyl group
and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_1$-$C_3$-haloalkyl group, a $C_1$-$C_3$-haloalkoxy group;
$R^2$ is selected from a hydrogen atom and a halogen atom;
$R^3$ is selected from,
  a $C_1$-$C_6$-alkoxy group,
  a $C_2$-$C_6$-alkenyl group,
  a $C_4$-$C_6$-cycloalkyl group,
  a $C_5$-$C_6$-cycloalkenyl group,
  a 4- to 6-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group,
  a 5- to 7-membered heterocycloalkyl group which is partially unsaturated and optionally substituted with one, two or three substituents and each substituent is independently selected from an oxo group (═O), a $C_1$-$C_3$-alkyl group and a halogen atom,
  a bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group,
  and a $NR^6R^7$ group,
with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4$/$R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6$/$R^7$ is independently selected from a hydrogen atom, a $C_2$-$C_6$-alkyl group, a —$C_1$—$C$— alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a —$C_1$-$C_5$-hydroxyalkylen-($C_1$-$C_3$-haloalkyl) group, a $C_4$-$C_6$-cycloalkyl group, and a 3- to 5-membered heterocycloalkyl group,
or $R^6$ and $R^7$ together form a 3-, 4-, 5-, 6- or 7-membered ring optionally containing one or two additional heteroatoms selected from the group consisting of —O—, —S— and —$NR^8$—,
and which is optionally substituted one, two, or three times with a substituent selected from a halogen atom, a hydroxy group, and a $C_1$-$C_3$-alkyl group
and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):

$R^1$ is selected from a hydrogen atom, a halogen atom, a cyano group, a $C_1$-$C_3$-alkyl group, a $C_2$-$C_3$-haloalkyl group, a $C_1$-$C_3$-haloalkoxy group;
$R^2$ is selected from a hydrogen atom and a halogen atom;
$R^3$ is selected from,
 a $C_1$-$C_6$-alkoxy group,
 a $C_2$-$C_6$-alkenyl group,
 a $C_4$-$C_6$-cycloalkyl group,
 a $C_5$-$C_6$-cycloalkenyl group,
 a 4- to 6-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group,
 a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom,
 a bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group,
 and a $NR^6R^7$ group,
 with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6/R^7$ is independently selected from a hydrogen atom, a $C_2$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-NR$^8$—$C_1$-$C_5$-alkyl group, a —$C_1$-$C_5$-hydroxyalkylen-($C_1$-$C_3$-haloalkyl) group, a $C_4$-$C_6$-cycloalkyl group, and a 3- to 5-membered heterocycloalkyl group,
or $R^6$ and $R^7$ together form a 3-, 4-, 5-, 6- or 7-membered ring optionally containing one or two additional heteroatoms selected from the group consisting of —O—, —S— and —NR$^8$—,
 and which is optionally substituted one, two, or three times with a substituent selected from a halogen atom, a hydroxy group, and a $C_1$-$C_3$-alkyl group
 and if $R^6$ and $R^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):

$R^1$ is selected from a hydrogen atom, a halogen atom, a $C_1$-$C_3$-alkyl group, a $C_1$-$C_3$-haloalkyl group, a $C_1$-$C_3$-haloalkoxy group;
$R^2$ is selected from a hydrogen atom and a halogen atom;
$R^3$ is selected from,
 a $C_1$-$C_6$-alkoxy group,
 a $C_2$-$C_4$-alkenyl group,
 a $C_5$-$C_6$-cycloalkenyl group,
 a 3- to 6-membered heterocycloalkyl group, which is optionally substituted with one or two substituents and each substituent is independently selected from a halogen atom and a $C_1$-$C_3$-alkyl group,
 a 5- to 6-membered heterocycloalkyl group which is partially unsaturated and optionally substituted with one or two substituents and each substituent is independently selected from an oxo group (=O), a $C_1$-$C_3$-alkyl group and a halogen atom,
 an aryl group which is optionally substituted with one, two or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
 a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a NR$^4$R$^5$ group,
 and a NR$^6$R$^7$ group,
 with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group; and
$R^6/R^7$ is independently selected from hydrogen atom, and a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, a —$C_1$-$C_3$-alkylen-NR$^8$—$C_1$-$C_3$-alkyl group, a —$C_1$-$C_3$-hydroxyalkylen-($C_1$-$C_3$-haloalkyl) group, a $C_3$-$C_6$-cycloalkyl group, a 3- to 5-membered heterocycloalkyl group,
or $R^6$ and $R^7$ together form a 4-, 5-, or 6-membered ring optionally containing one or two additional heteroatoms selected from the group consisting of —O—, —S— and —NR$^8$—,
 and which is optionally substituted one, two or three times with a substituent selected from a halogen atom and a $C_1$-$C_3$-alkyl group;
 and if $R^7$ and $R^8$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
$R^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):

$R^1$ is selected from a hydrogen atom, a halogen atom, a $C_1$-$C_3$-alkyl group, a $C_2$-$C_3$-haloalkyl group, a $C_1$-$C_3$-haloalkoxy group;
$R^2$ is selected from a hydrogen atom and a halogen atom;
$R^3$ is selected from, a $C_1$-$C_6$-alkoxy group,
a $C_2$-$C_4$-alkenyl group,
a $C_5$-$C_6$-cycloalkenyl group,
a 3- to 6-membered heterocycloalkyl group, which is optionally substituted with one or two substituents and each substituent is independently selected from a halogen atom and a $C_1$-$C_3$-alkyl group,
a 5- to 6-membered heterocycloalkyl group which is partially unsaturated and optionally substituted with one or two substituents and each substituent is independently selected from an oxo group (=O), a $C_1$-$C_3$-alkyl group and a halogen atom,
an aryl group which is optionally substituted with one, two or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a NR$^4$R$^5$ group,
and a NR$^6$R$^7$ group,
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
R$^4$/R$^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group; and
R$^6$/R$^7$ is independently selected from hydrogen atom, and a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, a —$C_1$-$C_3$-alkylen-NR$^8$—$C_1$-$C_3$-alkyl group, a —$C_1$-$C_3$-hydroxyalkylen-($C_1$-$C_3$-haloalkyl) group, a $C_3$-$C_6$-cycloalkyl group, a 3- to 5-membered heterocycloalkyl group,
or R$^6$ and R$^7$ together form a 4-, 5-, or 6-membered ring optionally containing one or two additional heteroatoms selected from the group consisting of —O—, —S— and —NR$^8$—,
and which is optionally substituted one, two or three times with a substituent selected from a halogen atom and a $C_1$-$C_3$-alkyl group;
and if R$^7$ and R$^8$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
R$^8$ is a hydrogen atom or a $C_1$-$C_3$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
R$^1$ is selected from a hydrogen atom, a halogen atom, a cyano group, a $C_1$-$C_3$-alkyl group, a $C_1$-$C_3$-haloalkyl group;
R$^2$ is selected from a hydrogen atom and a halogen atom;
R$^3$ is selected from,
a $C_1$-$C_6$-alkoxy group,
a $C_2$-$C_6$-alkenyl group,
a $C_5$-$C_6$-cycloalkenyl group,
a 3- to 7-membered heterocycloalkyl group, which is optionally substituted with one or two substituents and each substituent is independently selected from a halogen atom, a $C_1$-$C_3$-alkyl group, or a hydroxy group,
a 5- to 7-membered heterocycloalkyl group which is partially unsaturated;
an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group;
a mono- or bicyclic heteroaryl group which is optionally substituted with one, or two substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group;
and a NR$^6$R$^7$ group;
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
R$^4$/R$^5$ is a hydrogen atom;
R$^6$/R$^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group,
or a stereoisomer, a tautomer, an N-oxide, a hydrate, a solvate, or a salt thereof, or a mixture of same.

In accordance with an embodiment of the first aspect, the present invention provides compounds of general formula (I):
R$^1$ is selected from a hydrogen atom, a halogen atom, a cyano group, a $C_1$-$C_3$-alkyl group, a $C_2$-$C_3$-haloalkyl group;
R$^2$ is selected from a hydrogen atom and a halogen atom;
R$^3$ is selected from,
a $C_1$-$C_6$-alkoxy group,
a $C_2$-$C_6$-alkenyl group,
a $C_5$-$C_6$-cycloalkenyl group,
a 3- to 7-membered heterocycloalkyl group, which is optionally substituted with one or two substituents and each substituent is independently selected from a halogen atom, a $C_1$-$C_3$-alkyl group, or a hydroxy group,
a 5- to 7-membered heterocycloalkyl group which is partially unsaturated;
an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group;
a mono- or bicyclic heteroaryl group which is optionally substituted with one, or two substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group;
and a NR$^6$R$^7$ group;
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
R$^4$/R$^5$ is a hydrogen atom;
R$^6$/R$^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group,
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_1$-$C_3$-haloalkyl group;
$R^2$ is selected from a hydrogen atom and a halogen atom;
$R^3$ is selected from,
  a $C_2$-$C_6$-alkenyl group,
  a $C_5$-$C_6$-cycloalkenyl group,
  a 3- to 7-membered heterocycloalkyl group, which is optionally substituted with one or two substituents and each substituent is independently selected from a halogen atom, a $C_1$-$C_3$-alkyl group, or a hydroxy group,
  a 5- to 7-membered heterocycloalkyl group which is partially unsaturated;
  an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a —C(O)NR$^4$R$^5$ group and a NR$^4$R$^5$ group;
  a mono- or bicyclic heteroaryl group which is optionally substituted with one, or two substituents and each substituent is independently selected from a halogen atom, a $C_1$-$C_3$-alkyl group;
  and a NR$^6$R$^7$ group;
  with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
$R^4$/$R^5$ is a hydrogen atom;
$R^6$/$R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_1$-$C_3$-haloalkyl group;
$R^2$ is selected from a hydrogen atom and a halogen atom;
$R^3$ is selected from,
  a $C_2$-$C_6$-alkenyl group,
  a $C_5$-$C_6$-cycloalkenyl group,
  a 3- to 7-membered heterocycloalkyl group, which is optionally substituted with one or two substituents and each substituent is independently selected from a halogen atom, a $C_1$-$C_3$-alkyl group, or a hydroxy group,
  a 5- to 7-membered heterocycloalkyl group which is partially unsaturated;
  an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a —C(O)NR$^4$R$^5$ group and a NR$^4$R$^5$ group;
  a mono- or bicyclic heteroaryl group which is optionally substituted with one, or two substituents and each substituent is independently selected from a halogen atom, a $C_1$-$C_3$-alkyl group;
  and a NR$^6$R$^7$ group;
  with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
$R^4$/$R^5$ is a hydrogen atom;
$R^6$/$R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group;
or a stereoisomer, a tautomer, an N-oxide, a hydrate, a solvate, or a salt thereof, or a mixture of same.

In accordance with an embodiment of the first aspect, the present invention provides compounds of general formula (I): $R^1$ is selected from a hydrogen atom, a halogen atom, a cyano group, a $C_1$-$C_3$-alkyl group, a $C_2$-$C_3$-haloalkyl group;
$R^2$ is selected from a hydrogen atom and a halogen atom;
$R^3$ is selected from,
  a $C_2$-$C_6$-alkenyl group,
  a $C_5$-$C_6$-cycloalkenyl group,
  a 3- to 7-membered heterocycloalkyl group, which is optionally substituted with one or two substituents and each substituent is independently selected from a halogen atom, a $C_1$-$C_3$-alkyl group, or a hydroxy group,
  a 5- to 7-membered heterocycloalkyl group which is partially unsaturated; an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a —C(O)NR$^4$R$^5$ group and a NR$^4$R$^5$ group;
  a mono- or bicyclic heteroaryl group which is optionally substituted with one, or two substituents and each substituent is independently selected from a halogen atom, a $C_1$-$C_3$-alkyl group;
  and a NR$^6$R$^7$ group;
  with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
$R^4$/$R^5$ is a hydrogen atom;
$R^6$/$R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group; or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_1$-$C_3$-haloalkyl group;
$R^2$ is selected from a hydrogen atom and a halogen atom;
$R^3$ is selected from,
  a $C_2$-$C_6$-alkenyl group,
  a $C_5$-$C_6$-cycloalkenyl group,
  a 3- to 7-membered heterocycloalkyl group, which is optionally substituted with one or two substituents and each substituent is independently selected from a halogen atom, a $C_1$-$C_3$-alkyl group, or a hydroxy group,
  a 5- to 7-membered heterocycloalkyl group which is partially unsaturated;
  an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a —C(O)NR$^4$R$^5$ group and a NR$^4$R$^5$ group;
  a mono- or bicyclic heteroaryl group which is optionally substituted with one, or two substituents and each substituent is independently selected from a halogen atom, a $C_1$-$C_3$-alkyl group;
  and a NR$^6$R$^7$ group;

with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is a hydrogen atom;
$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group; or a stereoisomer, a tautomer, an N-oxide, a hydrate, a solvate, or a salt thereof, or a mixture of same.

In accordance with an embodiment of the first aspect, the present invention provides compounds of general formula (I): $R^1$ is selected from a hydrogen atom, a halogen atom, a cyano group, a $C_1$-$C_3$-alkyl group, a $C_1$-$C_3$-haloalkyl group;
$R^2$ is selected from a hydrogen atom and a halogen atom;
$R^3$ is selected from,
- a $C_2$-$C_6$-alkenyl group,
- a $C_5$-$C_6$-cycloalkenyl group,
- a 3- to 7-membered heterocycloalkyl group, which is optionally substituted with one or two substituents and each substituent is independently selected from a halogen atom, a $C_1$-$C_3$-alkyl group, or a hydroxy group,
- a 5- to 7-membered heterocycloalkyl group which is partially unsaturated;
- an aryl group which is optionally substituted with one, or two substituents and each substituent is independently selected from a halogen atom, a hydroxy group, a cyano group, a $C_1$-$C_3$-alkyl group, a $C_1$-$C_3$-alkoxy group, a —C(O)NR$^4$R$^5$ group and a NR$^4$R$^5$ group;
- a monocyclic heteroaryl group which is optionally substituted with one or two substituents and each substituent is independently selected from a halogen atom, a $C_1$-$C_3$-alkyl group and a NR$^6$R$^7$ group;
with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is a hydrogen atom;
$R^6/R^7$ is independently selected from a hydrogen atom or a —$C_1$-$C_5$-alkylen-O—$C_1$-$C_5$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a hydrogen atom, a halogen atom, a cyano group, a $C_1$-$C_3$-alkyl group, a $C_2$-$C_3$-haloalkyl group;
$R^2$ is selected from a hydrogen atom and a halogen atom;
$R^3$ is selected from,
- a $C_2$-$C_6$-alkenyl group,
- a $C_5$-$C_6$-cycloalkenyl group,
- a 3- to 7-membered heterocycloalkyl group, which is optionally substituted with one or two substituents and each substituent is independently selected from a halogen atom, a $C_1$-$C_3$-alkyl group, or a hydroxy group,
- a 5- to 7-membered heterocycloalkyl group which is partially unsaturated; an aryl group which is optionally substituted with one, or two substituents and each substituent is independently selected from a halogen atom, a hydroxy group, a cyano group, a $C_1$-$C_3$-alkyl group, a $C_1$-$C_3$-alkoxy group, a —C(O)NR$^4$R$^5$ group and a NR$^4$R$^5$ group;
- a monocyclic heteroaryl group which is optionally substituted with one or two substituents and each substituent is independently selected from a halogen atom, a $C_1$-$C_3$-alkyl group and a NR$^6$R$^7$ group;

with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is a hydrogen atom;
$R^6/R^7$ is independently selected from a hydrogen atom or a —$C_1$-$C_5$-alkylen-O—$C_1$-$C_5$-alkyl group;
or a stereoisomer, a tautomer, an N-oxide, a hydrate, a solvate, or a salt thereof, or a mixture of same.

In accordance with an embodiment of the first aspect, the present invention provides compounds of general formula (I): $R^1$ is selected from a halogen atom, a $C_1$-$C_3$-alkyl group and a $C_1$-$C_3$-haloalkyl group;
$R^2$ is selected from a hydrogen atom and a halogen atom;
$R^3$ is selected from,
- a $C_1$-$C_3$-alkoxy group,
- a $C_2$-$C_4$-alkenyl group
- a $C_5$-$C_6$-cycloalkenyl group,
- a 3- to 6-membered heterocycloalkyl group, which is optionally substituted with one or two substituents and each substituent is independently selected from a halogen atom, a hydroxy group and a $C_1$-$C_3$-alkyl group,
- a 5- to 6-membered heterocycloalkyl group which is partially unsaturated,
- an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
- a mono- or bicyclic heteroaryl group which is optionally substituted with one, two or three substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group,
- and a NR$^6$R$^7$ group,
with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is independently selected from a hydrogen atom and a $C_1$-$C_3$-alkyl group; and
$R^6/R^7$ is independently selected from a hydrogen atom, a $C_1$-$C_6$-alkyl group, a —$C_1$-$C_5$-alkylen-O—$C_1$-$C_5$-alkyl group, and a —$C_1$-$C_5$-hydroxyalkylen-$C_1$-$C_3$-haloalkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
$R^1$ is selected from a halogen atom, a $C_1$-$C_3$-alkyl group and a $C_2$-$C_3$-haloalkyl group;
$R^2$ is selected from a hydrogen atom and a halogen atom;
$R^3$ is selected from,
- a $C_1$-$C_3$-alkoxy group,
- a $C_2$-$C_4$-alkenyl group
- a $C_5$-$C_6$-cycloalkenyl group,
- a 3- to 6-membered heterocycloalkyl group, which is optionally substituted with one or two substituents and each substituent is independently selected from a halogen atom, a hydroxy group and a $C_1$-$C_3$-alkyl group,
- a 5- to 6-membered heterocycloalkyl group which is partially unsaturated,
- an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
a mono- or bicyclic heteroaryl group which is optionally substituted with one, two or three substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group,
and a NR$^6$R$^7$ group,
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;
R$^4$/R$^5$ is independently selected from a hydrogen atom and a $C_1$-$C_3$-alkyl group; and
R$^6$/R$^7$ is independently selected from a hydrogen atom, a $C_1$-$C_6$-alkyl group, a —$C_1$-$C_5$-alkylen-O—$C_1$-$C_5$-alkyl group, and a —$C_1$-$C_5$-hydroxyalkylen-$C_1$-$C_3$-haloalkyl group;
or a stereoisomer, a tautomer, an N-oxide, a hydrate, a solvate, or a salt thereof, or a mixture of same.

In accordance with an embodiment of the first aspect, the present invention provides compounds of general formula (I):
wherein
R$^1$ is selected from a hydrogen atom, a halogen atom, a $C_1$-$C_3$-alkyl group, a $C_1$-$C_3$-haloalkyl group, a $C_1$-$C_3$-haloalkoxy group;
R$^2$ is selected from a hydrogen atom and a halogen atom,
R$^3$ is selected from a halogen atom,
a $C_1$-$C_6$-alkoxy group,
a $C_2$-$C_4$-alkenyl group,
a $C_5$-$C_6$-cycloalkenyl group,
a 3- to 6-membered heterocycloalkyl group, which is optionally substituted with one or two substituents and each substituent is independently selected from a halogen atom and a $C_1$-$C_3$-alkyl group;
a 5- to 6-membered heterocycloalkyl group which is partially unsaturated and optionally substituted with one or two substituents and each substituent is independently selected from an oxo group (═O), a $C_1$-$C_3$-alkyl group and a halogen atom;
an aryl group which is optionally substituted with one, two or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group;
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a NR$^4$R$^5$ group;
and a NR$^6$R$^7$ group;
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom,
R$^4$/R$^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group; and
R$^6$/R$^7$ is independently selected from hydrogen atom, and a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, a —$C_1$-$C_3$-alkylen-NR$^8$—$C_1$-$C_3$-alkyl group, a $C_3$-$C_6$-cycloalkyl group, a 3- to 5-membered heterocycloalkyl group
or R$^6$ and R$^7$ together form a 4-, 5-, or 6-membered ring optionally containing one or two additional heteroatoms selected from the group consisting of —O—, —S— and —NR$^8$—, In accordance with an embodiment of the first aspect, the present invention provides compounds of general formula (I):
wherein
R$^1$ is selected from a hydrogen atom, a halogen atom, a $C_1$-$C_3$-alkyl group, a $C_1$-$C_3$-haloalkyl group, a $C_1$-$C_3$-haloalkoxy group;
R$^2$ is selected from a hydrogen atom and a halogen atom,
R$^3$ is selected from,
a $C_1$-$C_6$-alkoxy group,
a $C_2$-$C_4$-alkenyl group,
a $C_5$-$C_6$-cycloalkenyl group,
a 3- to 6-membered heterocycloalkyl group, which is optionally substituted with one or two substituents and each substituent is independently selected from a halogen atom and a $C_1$-$C_3$-alkyl group;
a 5- to 6-membered heterocycloalkyl group which is partially unsaturated and optionally substituted with one or two substituents and each substituent is independently selected from an oxo group (═O), a $C_1$-$C_3$-alkyl group and a halogen atom;
an aryl group which is optionally substituted with one, two or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group;
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a NR$^4$R$^5$ group;
and a NR$^6$R$^7$ group;
with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom,
R$^4$/R$^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group; and
R$^6$/R$^7$ is independently selected from hydrogen atom, and a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, a —$C_1$-$C_3$-alkylen-NR$^8$—$C_1$-$C_3$-alkyl group, a $C_3$-$C_6$-cycloalkyl group, a 3- to 5-membered heterocycloalkyl group
or R$^6$ and R$^7$ together form a 4-, 5-, or 6-membered ring optionally containing one or two additional heteroatoms selected from the group consisting of —O—, —S— and —NR$^8$—,
and which is optionally substituted one, two or three times with a substituent selected from a halogen atom and a $C_1$-$C_3$-alkyl group;
and if R$^7$ and R$^8$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
R$^8$ is a hydrogen atom or a $C_1$-$C_3$-alkyl group,
or a stereoisomer, a tautomer, an N-oxide, a hydrate, a solvate, or a salt thereof, or a mixture of same.

and which is optionally substituted one, two or three times with a substituent selected from a halogen atom and a $C_1$-$C_3$-alkyl group;

and if $R^7$ and $R^8$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group, or a stereoisomer, a tautomer, an N-oxide, a hydrate, a solvate, or a salt thereof, or a mixture of same.

In accordance with a second embodiment of the first aspect, the present invention provides compounds of general formula (I):
wherein
$R^1$ is selected from a halogen atom, a $C_1$-$C_3$-alkyl group and a $C_1$-$C_3$-haloalkyl group;
$R^2$ is selected from a hydrogen atom and a halogen atom,
$R^3$ is selected from a halogen atom,
  a $C_1$-$C_3$-alkoxy group,
  a $C_2$-$C_4$-alkenyl group
  a $C_5$-$C_6$-cycloalkenyl group,
  a 3- to 6-membered heterocycloalkyl group, which is optionally substituted with one or two substituents and each substituent is independently selected from a halogen atom and a $C_1$-$C_3$-alkyl group;
  a 5- to 6-membered heterocycloalkyl group which is partially unsaturated and optionally substituted an oxo group (=O),
  an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;
  a mono- or bicyclic heteroaryl group which is optionally substituted with one, two or three substituents and each substituent is independently selected from a halogen atom, a $C_1$-$C_3$-alkyl group, a $C_1$-$C_3$-haloalkyl group, a $C_1$-$C_3$-alkoxy group, and a $NR^4R^5$ group;
  and a $NR^6R^7$ group;
  with the proviso that $R^3$ can not be imidazol-1-yl if $R^1$ and $R^2$ are a hydrogen atoms,
$R^4$/$R^5$ is independently selected from a hydrogen atom and a $C_1$-$C_3$-alkyl group; and
$R^6$/$R^7$ is independently selected from a hydrogen atom, a $C_3$-$C_5$-cycloalkyl group, and a $C_1$-$C_6$-alkyl group
or $R^6$ and $R^7$ together form a 4-, 5-, 6-membered ring optionally containing one or two additional heteroatoms selected from the group consisting of —O—, —S— and —$NR^8$—,
  and which is optionally substituted one, two times with a substituent selected from a halogen atom, a hydroxy group and a $C_1$-$C_3$-alkyl group;
  and if $R^6$ and $R^7$ together form a 5-, or 6-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;
  where $R^8$ is a hydrogen atom or a $C_1$-$C_3$-alkyl group, or a stereoisomer, a tautomer, an N-oxide, a hydrate, a solvate, or a salt thereof, or a mixture of same.

In accordance with a second embodiment of the first aspect, the present invention provides compounds of general formula (I):
wherein
$R^1$ is selected from a halogen atom, a $C_1$-$C_3$-alkyl group and a $C_1$-$C_3$-haloalkyl group;
$R^2$ is selected from a hydrogen atom and a halogen atom, $R^3$ is selected from,
  a $C_1$-$C_3$-alkoxy group,
  a $C_2$-$C_4$-alkenyl group
  a $C_5$-$C_6$-cycloalkenyl group,
  a 3- to 6-membered heterocycloalkyl group, which is optionally substituted with one or two substituents and each substituent is independently selected from a halogen atom and a $C_1$-$C_3$-alkyl group;
  a 5- to 6-membered heterocycloalkyl group which is partially unsaturated and optionally substituted an oxo group (=O),
  an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group; a mono- or bicyclic heteroaryl group which is optionally substituted with one, two or three substituents and each substituent is independently selected from a halogen atom, a $C_1$-$C_3$-alkyl group, a $C_1$-$C_3$-haloalkyl group, a $C_1$-$C_3$-alkoxy group, and a $NR^4R^5$ group;
  and a $NR^6R^7$ group;
  with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom,
$R^4$/$R^5$ is independently selected from a hydrogen atom and a $C_1$-$C_3$-alkyl group; and
$R^6$/$R^7$ is independently selected from a hydrogen atom, a $C_3$-$C_5$-cycloalkyl group, and a $C_1$-$C_6$-alkyl group
or $R^6$ and $R^7$ together form a 4-, 5-, 6-membered ring optionally containing one or two additional heteroatoms selected from the group consisting of —O—, —S— and —$NR^8$—,
  and which is optionally substituted one, two times with a substituent selected from a halogen atom, a hydroxy group and a $C_1$-$C_3$-alkyl group;
  and if $R^6$ and $R^7$ together form a 5-, or 6-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;
  where $R^8$ is a hydrogen atom or a $C_1$-$C_3$-alkyl group, or a stereoisomer, a tautomer, an N-oxide, a hydrate, a solvate, or a salt thereof, or a mixture of same.

In accordance with a third embodiment of the first aspect, the present invention provides compounds of general formula (I): wherein
$R^1$ is selected from a hydrogen atom, a $CF_3$, group, a fluorine atom, a chlorine atom, a methyl group, a cyano group,
$R^2$ is a hydrogen atom, a fluorine atom, a chlorine atom,
$R^3$ is selected from,
  a methoxy group,
  a 2-methylprop-1-en-1-yl group,
  a -(2E)-but-2-en-2-yl group,
  a cyclopent-1-en-1-yl group,
  a cyclohex-1-en-1-yl group,
  a 3,6-dihydro-2H-pyran-4-yl group,
  a tetrahydropyran-4-yl group,
  a azetidin-1-yl group which is substituted with two halogen atoms or a hydroxy group,
  a 3-azabicyclo[3.1.1]hept-3-yl group which is substituted with two halogen atoms
  a 3-azabicyclo[3.1.0]hex-3-yl group which is optionally substituted with a methyl group,
  a piperidin-1-yl group which is optionally substituted with one or two halogen atoms
  a morpholin-4-yl group, a pyrrolidin-1-yl group which is substituted with a methyl group,
a phenyl group which is optionally substituted with one, two or three substituents and each substituent is independently selected from a halogen atom, a hydroxy group, a methyl group, an ethyl group, a $CF_3$ group, a cyano group, a methoxy group, a ethoxy group, a —$OCF_3$ group, a $NH_2$ group and a $C(O)NH_2$ group,
a 1H-pyrazol-4-yl group, which is optionally substituted with a difluoromethyl group,
a 1H-pyrazol-1-yl group, which is optionally substituted with a trifluoromethyl group,
a furan-3-yl group,
a pyridin-3-yl and a pyridin-4-yl group each group being optionally substituted with one or two substituents and each substituent is independently selected from a halogen atom, a methyl group, a trifluoromethyl group, a methoxy group and a $NH_2$ group,
a pyrimidin-5-yl group, which is optionally substituted with a methyl group, a $NH_2$ group,
a 1H-indol-6-yl group, a 1H-indol-4-yl group,
a —$NHCH_3$ group, a —$NH(C_2H_5)$ group, a —NH—$(CH_2)_2$—O—$CH_3$ group, a —NH—$CH_2$—CH(OH)—$CF_3$ group;
with the proviso that $R^3$ can not be morpholin-4-yl, if $R^1$ is trifluoromethyl and $R^2$ is a hydrogen atom
or a stereoisomer, a tautomer, an N-oxide, a hydrate, a solvate, or a salt thereof, or a mixture of same.

In accordance with a third embodiment of the first aspect, the present invention provides compounds of general formula (I): wherein
$R^1$ is selected from a hydrogen atom, a fluorine atom, a chlorine atom, a methyl group, a cyano group,
$R^2$ is a hydrogen atom, a fluorine atom, a chlorine atom,
$R^3$ is selected from,
 a methoxy group,
 a 2-methylprop-1-en-1-yl group,
 a -(2E)-but-2-en-2-yl group,
 a cyclopent-1-en-1-yl group,
 a cyclohex-1-en-1-yl group,
 a 3,6-dihydro-2H-pyran-4-yl group,
 a tetrahydropyran-4-yl group,
 a azetidin-1-yl group which is substituted with two halogen atoms or a hydroxy group,
 a 3-azabicyclo[3.1.1]hept-3-yl group which is substituted with two halogen atoms
 a 3-azabicyclo[3.1.0]hex-3-yl group which is optionally substituted with a methyl group,
 a piperidin-1-yl group which is optionally substituted with one or two halogen atoms
 a morpholin-4-yl group,
 a pyrrolidin-1-yl group which is substituted with a methyl group,
 a phenyl group which is optionally substituted with one, two or three substituents and each substituent is independently selected from a halogen atom, a hydroxy group, a methyl group, an ethyl group, a $CF_3$ group, a cyano group, a methoxy group, a ethoxy group, a —$OCF_3$ group, a $NH_2$ group and a $C(O)NH_2$ group,
 a 1H-pyrazol-4-yl group, which is optionally substituted with a difluoromethyl group,
 a 1H-pyrazol-1-yl group, which is optionally substituted with a trifluoromethyl group,
 a furan-3-yl group,
 a pyridin-3-yl and a pyridin-4-yl group each group being optionally substituted with one or two substituents and each substituent is independently selected from a halogen atom, a methyl group, a trifluoromethyl group, a methoxy group and a $NH_2$ group,
 a pyrimidin-5-yl group, which is optionally substituted with a methyl group, a $NH_2$ group,
 a 1H-indol-6-yl group, a 1H-indol-4-yl group,
 a —$NHCH_3$ group, a —$NH(C_2H_5)$ group, a —NH—$(CH_2)_2$—O—$CH_3$ group, a —NH—$CH_2$—CH(OH)—$CF_3$ group;
with the proviso that $R^3$ can not be morpholin-4-yl, if $R^1$ is trifluoromethyl and $R^2$ is a hydrogen atom
or a stereoisomer, a tautomer, an N-oxide, a hydrate, a solvate, or a salt thereof, or a mixture of same.

In accordance with a third embodiment of the first aspect, the present invention provides compounds of general formula (I):
 wherein
$R^1$ is selected from a $CF_3$, group, a fluorine atom, a chlorine atom, a hydroxy group, a methyl group, an ethyl group, a methoxy group and an amino group,
$R^2$ is a hydrogen atom, a fluorine atom,
$R^3$ is selected from
 a methoxy group,
 a 2-methylprop-1-en-1-yl group,
 a -(2E)-but-2-en-2-yl group,
 a 3,6-dihydro-2H-pyran-4-yl group,
 a azetidin-1-yl group which is optionally substituted with one or two halogen atoms or a hydroxy group,
 a 3-azabicyclo[3.1.1]hept-3-yl group which is optionally substituted with one or two halogen atoms,
 a piperidin-1-yl group which is optionally substituted with one or two substituents and each substituent is independently selected from a fluorine atom and a methyl group,
 a morpholinyl group which is optionally substituted with one or two methyl groups,
 a pyrrolidin-1-yl group which is optionally substituted with one or two halogen atoms or a methyl group,
 a 5,6-dihydro-1H-pyran-4-yl group,
 a 6-oxo-1,6-dihydropyridin-3-yl group which is optionally substituted with one or two substituents and each substituent is independently selected from a hydrogen atom and a methyl group,
 a 6-oxo-1,4,5,6-tetrahydropyridazin-3-yl group,
 a 3-azabicyclo[3.1.0]hex-3-yl group which is optionally substituted with a methyl group,
 a cyclopent-1 en-1-yl group,
 a cyclohex-1-en-1-yl group,
 a phenyl group which is optionally substituted with one, two or three substituents and each substituent is independently selected from from a halogen atom, a hydroxy group, a methyl group, an ethyl group, a $CF_3$, $CF_2H$ group, a methoxy group, a $NH_2$ group and a $NHCH_3$ group,
 a 2H-pyrrol-1-yl group, which is optionally substituted with one or two substituents and each substituent is independently selected from a hydrogen atom, a cyano group and a methyl group,
 a 1H-pyrazol-4-yl group, which is optionally substituted with a methyl group,
 a 1H-pyrazol-5-yl group, which is optionally substituted with a methyl group,
 a furan-3-yl group,
 a 1,2-thiazol-4-yl group which is optionally substituted with a methyl group,
 a 1,3-thiazol-5-yl group which is optionally substituted with a methyl groups, a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group, a pyrimidin-5-yl group, which is optionally substituted with a methyl group, an amino group, (unsubst., CH3)

a 1H-indol-6-yl group, a 1H-indol-4-yl group, a 1H-indazol-6-yl group, a 1H-benzimidazol-6-yl group, a $NHCH_3$ group, a $NH(C_2H_5)$ group, a $NH(C_3H_7)$ group, a $NH(C_4H_9)$ group, a $NCH_3(C_4H_9)$ group, a $NH(C_5H_{11})$ group, a NH(cyclopentyl) group, a $NCH_3$(cyclopentyl) group;

or a stereoisomer, a tautomer, an N-oxide, a hydrate, a solvate, or a salt thereof, or a mixture of same.

In accordance with a third embodiment of the first aspect, the present invention provides compounds of general formula (I):

wherein $R^1$ is selected from a $CF_3$, group, a fluorine atom, a chlorine atom, a hydroxy group, a methyl group, an ethyl group, a methoxy group and an amino group, $R^2$ is a hydrogen atom, a fluorine atom, $R^3$ is selected from a methoxy group, a 2-methylprop-1-en-1-yl group, a -(2E)-but-2-en-2-yl group, a 3,6-dihydro-2H-pyran-4-yl group, a azetidin-1-yl group which is optionally substituted with one or two halogen atoms or a hydroxy group, a 3-azabicyclo[3.1.1]hept-3-yl group which is optionally substituted with one or two halogen atoms, a piperidin-1-yl group which is optionally substituted with one or two substituents and each substituent is independently selected from a fluorine atom and a methyl group, a morpholinyl group which is optionally substituted with one or two methyl groups, a pyrrolidin-1-yl group which is optionally substituted with one or two halogen atoms or a methyl group, a 5,6-dihydro-1H-pyran-4-yl group, a 6-oxo-1,6-dihydropyridin-3-yl group which is optionally substituted with one or two substituents and each substituent is independently selected from a hydrogen atom and a methyl group, a 6-oxo-1,4,5,6-tetrahydropyridazin-3-yl group, a 3-azabicyclo[3.1.0]hex-3-yl group which is optionally substituted with a methyl group, a cyclopent-1 en-1-yl group, a cyclohex-1-en-1-yl group, a phenyl group which is optionally substituted with one, two or three substituents and each substituent is independently selected from a halogen atom, a hydroxy group, a methyl group, an ethyl group, a $CF_3$, $CF_2H$ group, a methoxy group, a $NH_2$ group and a $NHCH_3$ group, a 2H-pyrrol-1-yl group, which is optionally substituted with one or two substituents and each substituent is independently selected from a hydrogen atom, a cyano group and a methyl group, a 1H-pyrazol-4-yl group, which is optionally substituted with a methyl group, a 1H-pyrazol-5-yl group, which is optionally substituted with a methyl group, a furan-3-yl group, a 1,2-thiazol-4-yl group which is optionally substituted with a methyl group, a 1,3-thiazol-5-yl group which is optionally substituted with a methyl groups, a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group, a pyrimidin-5-yl group, which is optionally substituted with a methyl group, an amino group, (unsubst., CH3)

a 1H-indol-6-yl group, a 1H-indol-4-yl group, a 1H-indazol-6-yl group, a 1H-benzimidazol-6-yl group, a $NHCH_3$ group, a $NH(C_2H_5)$ group, a $NH(C_3H_7)$ group, a $NH(C_4H_9)$ group, a $NCH_3(C_4H_9)$ group, a $NH(C_5H_{11})$ group, a NH(cyclopentyl) group, a $NCH_3$(cyclopentyl) group;

with the proviso that $R^3$ can not be morpholin-4-yl, if $R^1$ is trifluoromethyl and $R^2$ is a hydrogen atom or a stereoisomer, a tautomer, an N-oxide, a hydrate, a solvate, or a salt thereof, or a mixture of same.

In accordance with a further embodiment of the first aspect, the present invention provides compounds of general formula (I):

wherein $R^1$ is selected from a $CF_3$, group, a fluorine atom, a chlorine atom, a hydroxy group, a methyl group, an ethyl group, a methoxy group and an amino group, $R^2$ is a hydrogen atom, a fluorine atom, $R^3$ is selected from a methoxy group, a 2-methylprop-1-en-1-yl group, a -(2E)-but-2-en-2-yl group, a 3,6-dihydro-2H-pyran-4-yl group, a azetidin-1-yl group which is optionally substituted with one or two halogen atoms or a hydroxy group, a 3-azabicyclo[3.1.1]hept-3-yl group which is optionally substituted with one or two halogen atoms a piperidin-1-yl group which is optionally substituted with one or two substituents and each substituent is independently selected from a fluorine atom and a methyl group a morpholinyl group which is optionally substituted with one or two methyl groups, a pyrrolidin-1-yl group which is optionally substituted with one or two halogen atoms or a methyl group a 6-oxo-1,4,5,6-tetrahydropyridazin-3-yl group, a 3-azabicyclo[3.1.0]hex-3-yl group which is optionally substituted with a methyl group, a cyclopent-1 en-1-yl group, a cyclohex-1-en-1-yl group, a phenyl group which is optionally substituted with one, two or three substituents and each substituent is independently selected from a halogen atom, a hydroxy group, a methyl group, a $CF_3$, a methoxy group, and a $NH_2$ group, a 1H-pyrazol-4-yl group, which is optionally substituted with a methyl group, a furan-3-yl group, a pyridin-3-yl, a pyridin-4-yl and a pyridin 5-yl group each group being optionally substituted with one or two substituents and each substituent is independently selected from a halogen atom (F, Cl, a methyl group, a trifluoromethyl group, a methoxy group and a $NH_2$ group,
a pyrimidin-5-yl group, which is optionally substituted with a methyl group, an amino group, (unsubst., CH3)
a 1H-indol-6-yl group, a 1H-indol-4-yl group,
a $NHCH_3$ group, and a $NH(C_2H_5)$ group;
with the proviso that $R^3$ can not be morpholin-4-yl, if $R^1$ is trifluoromethyl and $R^2$ is a hydrogen atom
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
6-(3-Chloro-4-methoxyphenyl)-4,5-dihydropyridazin-3(2H)-one,
6-(4-Chloro-3-methylphenyl)-4,5-dihydropyridazin-3(2H)-one,
6-(3,4-Dichlorophenyl)-4,5-dihydropyridazin-3(2H)-one,
6-[4-(Morpholin-4-yl)-3-(trifluoromethyl)phenyl]-4,5-dihydropyridazin-3(2H)-one)
6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on,
6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[4-(Ethylamino)-3-(trifluoromethyl)phenyl]-4,5-dihydropyridazin-3(2H)-one,
6-[4-(3,3-Difluoroazetidin-1-yl)-3-(trifluoromethyl)phenyl]-4,5-dihydropyridazin-3(2H)-one,
6-{4-[2-Methylpyrrolidin-1-yl]-3-(trifluoromethyl)phenyl}-4,5-dihydropyridazin-3(2H)-one,
6-[4-(6,6-Difluoro-3-azabicyclo[3.1.1]hept-3-yl)-3-(trifluoromethyl)phenyl]-4,5-dihydropyridazin-3(2H)-one,
6-[4-(3,3-Difluoropyrrolidin-1-yl)-3-(trifluoromethyl)phenyl]-4,5-dihydropyridazin-3(2H)-one,
6-[4-(Methylamino)-3-(trifluoromethyl)phenyl]-4,5-dihydropyridazin-3(2H)-one,
6-[4-(3-Hydroxyazetidin-1-yl)-3-(trifluoromethyl)phenyl]-4,5-dihydropyridazin-3(2H)-one,
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one
6-(2,2'-Difluoro-4-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4-dimethylbiphenyl-4-yl)-4,5-dihydropyridazin-3(2H)-one,
6-(2,5'-Difluoro-2'-methylbiphenyl-4-yl)-4,5-dihydropyridazin-3(2H)-one, 6-(2,3'-Difluoro-4'-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one,
6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one,
6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one,
6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one,
6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3-dimethylbiphenyl-4-yl)-4,5-dihydropyridazin-3(2H)-one,
6-(2,3'-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one,
6-(4-Morpholinophenyl)-4,5-dihydropyridazin-3(2H)-one,
6-(3,5-Dichloro-4-morpholinophenyl)-4,5-dihydropyridazin-3(2H)-one, 6-{4-[1-(difluoromethyl)-1H-pyrazol-4-yl]-3-(trifluoromethyl)phenyl}-4,5-dihydropyridazin-3(2H)-one,
6-[4'-fluoro-2-(trifluoromethyl)[1,1'-biphenyl]-4-yl]-4,5-dihydropyridazin-3(2H)-one,
6-{4-[(2-methoxyethyl)amino]-3-(trifluoromethyl)phenyl}-4,5-dihydropyridazin-3(2H)-one,
6-[4-{[3,3,3-trifluoro-2-hydroxypropyl]amino}-3-(trifluoromethyl)phenyl-4,5-dihydropyridazin-3(2H)-one (racemic) and
6-{3-fluoro-4-[3-(trifluoromethyl)-1H-pyrazol-1-yl]phenyl}-4,5-dihydropyridazin-3(2H)-one or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group 6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on,
6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[4-(Ethylamino)-3-(trifluoromethyl)phenyl]-4,5-dihydropyridazin-3(2H)-one,
6-[4-(3,3-Difluoroazetidin-1-yl)-3-(trifluoromethyl)phenyl]-4,5-dihydropyridazin-3(2H)-one,
6-{4-[2-Methylpyrrolidin-1-yl]-3-(trifluoromethyl)phenyl}-4,5-dihydropyridazin-3(2H)-one,
6-[4-(6,6-Difluoro-3-azabicyclo[3.1.1]hept-3-yl)-3-(trifluoromethyl)phenyl]-4,5-dihydropyridazin-3(2H)-one,
6-[4-(3,3-Difluoropyrrolidin-1-yl)-3-(trifluoromethyl)phenyl]-4,5-dihydropyridazin-3(2H)-one,
6-[4-(Methylamino)-3-(trifluoromethyl)phenyl]-4,5-dihydropyridazin-3(2H)-one,
6-[4-(3-Hydroxyazetidin-1-yl)-3-(trifluoromethyl)phenyl]-4,5-dihydropyridazin-3(2H)-one,
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one
6-(2,2'-Difluoro-4'-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4-dimethylbiphenyl-4-yl)-4,5-dihydropyridazin-3(2H)-one,
6-(2,5'-Difluoro-2-methylbiphenyl-4-yl)-4,5-dihydropyridazin-3(2H)-one,
6-(2,3'-Difluoro-4-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one, 6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one,
6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one,
6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one,
6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3-dimethylbiphenyl-4-yl)-4,5-dihydropyridazin-3(2H)-one,
6-(2,3-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one,
6-(3,5-Dichloro-4-morpholinophenyl)-4,5-dihydropyridazin-3(2H)-one,
6-{4-[1-(difluoromethyl)-1H-pyrazol-4-yl]-3-(trifluoromethyl)phenyl}-4,5-dihydropyridazin-3(2H)-one,
6-[4'-fluoro-2-(trifluoromethyl)[1,1'-biphenyl]-4-yl]-4,5-dihydropyridazin-3(2H)-one,
6-{4-[(2-methoxyethyl)amino]-3-(trifluoromethyl)phenyl}-4,5-dihydropyridazin-3(2H)-one, 6-[4-{[3,3,3-trifluoro-2-hydroxypropyl]amino}-3-(trifluoromethyl)phenyl]-4,5-dihydropyridazin-3(2H)-one (racemic) and 6-{3-fluoro-4-[3-(trifluoromethyl)-1H-pyrazol-1-yl]phenyl}-4,5-dihydropyridazin-3(2H)-one or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on,
6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one
6-(2,2'-Difluoro-4-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4-dimethylbiphenyl-4-yl)-4,5-dihydropyridazin-3(2H)-one,
6-(2,5'-Difluoro-2'-methylbiphenyl-4-yl)-4,5-dihydropyridazin-3(2H)-one,
6-(2,3'-Difluoro-4-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one,
6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one,
6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one, 6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one,
6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6'-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3'-dimethylbiphenyl-4-yl)-4,5-dihydropyridazin-3(2H)-one,
6-(2,3'-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one,
6-(4-Morpholinophenyl)-4,5-dihydropyridazin-3(2H)-one,
6-(3,5-Dichloro-4-morpholinophenyl)-4,5-dihydropyridazin-3(2H)-one,
6-{4-[(2-methoxyethyl)amino]-3-(trifluoromethyl)phenyl}-4,5-dihydropyridazin-3(2H)-one,
6-[4-{[3,3,3-trifluoro-2-hydroxypropyl]amino}-3-(trifluoromethyl)phenyl]-4,5-dihydropyridazin-3(2H)-one (racemic) and
6-{3-fluoro-4-[3-(trifluoromethyl)-1H-pyrazol-1-yl]phenyl}-4,5-dihydropyridazin-3(2H)-one or a stereoisomer, a tautomer, an N-oxide, a hydrate, a solvate, or a salt thereof, or a mixture of same.

In accordance with a third embodiment of the first aspect, the present invention provides compounds of general formula (I): wherein the compound is selected from the group
6-{4-[1-(difluoromethyl)-1H-pyrazol-4-yl]-3-(trifluoromethyl)phenyl}-4,5-dihydropyridazin-3(2H)-one
6-[4'-fluoro-2-(trifluoromethyl)[1,1'-biphenyl]-4-yl]-4,5-dihydropyridazin-3(2H)-one
6-{4-[(2-methoxyethyl)amino]-3-(trifluoromethyl)phenyl}-4,5-dihydropyridazin-3(2H)-one
6-[4-{[3,3,3-trifluoro-2-hydroxypropyl]amino}-3-(trifluoromethyl)phenyl]-4,5-dihydropyridazin-3(2H)-one (racemic)
[Last name still missing]-6-{4-[1-(trifluoromethyl)-1H-pyrazol-1-yl]-3-(fluoro)phenyl}-4,5-dihydropyridazin-3(2H)-one?
or a stereoisomer, a tautomer, an N-oxide, a hydrate, a solvate, or a salt thereof, or a mixture of same.

In accordance with a further embodiment of the first aspect, the present invention provides compounds of general formula (I):

wherein the compound is selected from the group

6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on,
6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(3-Chloro-4-methoxyphenyl)-4,5-dihydropyridazin-3(2H)-one,
6-(4-Chloro-3-methylphenyl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[4-(Ethylamino)-3-(trifluoromethyl)phenyl]-4,5-dihydropyridazin-3(2H)-one,
6-[4-(3,3-Difluoroazetidin-1-yl)-3-(trifluoromethyl)phenyl]-4,5-dihydropyridazin-3(2H)-one,
6-{4-[2-Methylpyrrolidin-1-yl]-3-(trifluoromethyl)phenyl}-4,5-dihydropyridazin-3(2H)-one,
6-[4-(6,6-Difluoro-3-azabicyclo[3.1.1]hept-3-yl)-3-(trifluoromethyl)phenyl]-4,5-dihydropyridazin-3(2H)-one,
6-[4-(3,3-Difluoropyrrolidin-1-yl)-3-(trifluoromethyl)phenyl]-4,5-dihydropyridazin-3(2H)-one,
6-[4-(Methylamino)-3-(trifluoromethyl)phenyl]-4,5-dihydropyridazin-3(2H)-one,
6-[4-(3-Hydroxyazetidin-1-yl)-3-(trifluoromethyl)phenyl]-4,5-dihydropyridazin-3(2H)-one,
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one
6-(2,2'-Difluoro-4-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4-dimethylbiphenyl-4-yl)-4,5-dihydropyridazin-3(2H)-one,
6-(2,5'-Difluoro-2-methylbiphenyl-4-yl)-4,5-dihydropyridazin-3(2H)-one,
6-(2,3'-Difluoro-4-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one,
6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one, 6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one,
6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one,
6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3-dimethylbiphenyl-4-yl)-4,5-dihydropyridazin-3(2H)-one,
6-(2,3'-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one,
6-(4-Morpholinophenyl)-4,5-dihydropyridazin-3(2H)-one,
6-(3,5-Dichloro-4-morpholinophenyl)-4,5-dihydropyridazin-3(2H)-one,
6-(3,4-Dichlorophenyl)-4,5-dihydropyridazin-3(2H)-one
and
6-[4-(Morpholin-4-yl)-3-(trifluoromethyl)phenyl]-4,5-dihydropyridazin-3(2H)-one
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on, 6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[4-(Ethylamino)-3-(trifluoromethyl)phenyl]-4,5-dihydropyridazin-3(2H)-one,
6-[4-(3,3-Difluoroazetidin-1-yl)-3-(trifluoromethyl)phenyl]-4,5-dihydropyridazin-3(2H)-one,
6-{4-[2-Methylpyrrolidin-1-yl]-3-(trifluoromethyl)phenyl}-4,5-dihydropyridazin-3(2H)-one,
6-[4-(6,6-Difluoro-3-azabicyclo[3.1.1]hept-3-yl)-3-(trifluoromethyl)phenyl]-4,5-dihydropyridazin-3(2H)-one,
6-[4-(3,3-Difluoropyrrolidin-1-yl)-3-(trifluoromethyl)phenyl]-4,5-dihydropyridazin-3(2H)-one,
6-[4-(Methylamino)-3-(trifluoromethyl)phenyl]-4,5-dihydropyridazin-3(2H)-one,
6-[4-(3-Hydroxyazetidin-1-yl)-3-(trifluoromethyl)phenyl]-4,5-dihydropyridazin-3(2H)-one,
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one,
6-(2,2'-Difluoro-4-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4'-dimethylbiphenyl-4-yl)-4,5-dihydropyridazin-3(2H)-one,
6-(2,5'-Difluoro-2-methylbiphenyl-4-yl)-4,5-dihydropyridazin-3(2H)-one,
6-(2,3'-Difluoro-4-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one,
6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one,
6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one, 6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one,
6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6'-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3'-dimethylbiphenyl-4-yl)-4,5-dihydropyridazin-3(2H)-one,
6-(2,3'-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one, and
6-(3,5-Dichloro-4-morpholinophenyl)-4,5-dihydropyridazin-3(2H)-one
or a stereoisomer, a tautomer, an N-oxide, a hydrate, a solvate, or a salt thereof, or a mixture of same.

Further Embodiments of the Present Invention

In a further embodiment of the first aspect or any embodiment derived therefrom, the present invention provides compounds of formula (I), supra, in which:
$R^1$ is selected from a hydrogen atom, a halogen atom, and a cyano group, a $C_1$-$C_3$-alkyl group, a $C_1$-$C_3$-haloalkyl group, a $C_1$-$C_3$-haloalkoxy group; and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is selected from a hydrogen atom, a halogen atom, and a cyano group, a $C_1$-$C_3$-alkyl group, a $C_2$-$C_3$-haloalkyl group, a $C_1$-$C_3$-haloalkoxy group; and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is selected from a hydrogen atom, a halogen atom, and a cyano group, a $C_1$-$C_3$-alkyl group, a $C_1$-$C_3$-haloalkyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a halogen atom, a cyano group, a $C_1$-$C_3$-alkyl group, a $C_1$-$C_3$-haloalkyl group, or a $C_1$-$C_3$-haloalkoxy group and stereoisomers, tautomers, N-oxides, hydrates, solvates, and salts thereof, and mixtures of same In another embodiment of the first aspect, the present invention provides compounds of formula (I), supra, in which:
$R^1$ is hydrogen atom, a halogen atom, a $C_1$-$C_3$-alkyl group, a $C_1$-$C_3$-haloalkyl group, or a $C_1$-$C_3$-haloalkoxy group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^1$ is hydrogen atom, a fluorine atom, a methyl group, a trifluormethyl group, or a trifluoromethoxy group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom or a trifluoromethyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a trifluoromethyl group and stereoisomers, tautomers, N-oxides, hydrates, solvates, and salts thereof, and mixtures of same with the proviso that if $R^1$ is trifluoromethyl group and $R^2$ is hydrogen, $R^3$ can not be morpholin-4-yl.

In another embodiment of the first aspect or any embodiment derived therefrom, the present invention provides compounds of formula (I), supra, in which:
$R^2$ is a hydrogen atom or a halogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom or a trifluoromethyl group and $R^2$ is a hydrogen atom or a methyl group and stereoisomers, tautomers, N-oxides, hydrates, solvates, and salts thereof, and mixtures of same with the proviso that if $R^1$ is trifluoromethyl group and $R^2$ is hydrogen, $R^3$ can not be morpholin-4-yl.

In another embodiment of the first aspect or any embodiment derived therefrom, the present invention provides compounds of formula (I), supra, in which
$R^3$ is,
a $C_2$-$C_6$-alkenyl group,
a $C_5$-$C_6$-cycloalkyl group which is optionally partially unsaturated, a 3- to 6-membered heterocycloalkyl group, which is optionally substituted with one, two or three substituents and each substituent is independently selected from a halogen atom and a $C_1$-$C_3$-alkyl group,
a 5- to 6-membered heterocycloalkyl group which is partially unsaturated and optionally substituted with one, two or three substituents and each substituent is independently selected from an oxo group (=O), a $C_1$-$C_3$-alkyl group and a halogen atom,
an aryl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^4R^5$ group; and
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
or a $NR^7R^8$ group,
with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which
$R^3$ is,
a $C_2$-$C_6$-alkenyl group,
a $C_5$-$C_6$-cycloalkyl group which is optionally partially unsaturated,
a 3- to 6-membered heterocycloalkyl group, which is optionally substituted with one, two or three substituents and each substituent is independently selected from a halogen atom and a $C_1$-$C_3$-alkyl group,
a 5- to 6-membered heterocycloalkyl group which is partially unsaturated and optionally substituted with one, two or three substituents and each substituent is independently selected from an oxo group (=O), a $C_1$-$C_3$-alkyl group and a halogen atom, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which
$R^3$ is,
a $C_2$-$C_6$-alkenyl group,
a $C_5$-$C_6$-cycloalkyl group which is optionally partially unsaturated,
a 3- to 6-membered heterocycloalkyl group, which is optionally substituted with one, two or three substituents and each substituent is independently selected from a halogen atom and a $C_1$-$C_3$-alkyl group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which
$R^3$ is an aryl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^4R^5$ group; and a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;

or a $NR^7R^8$ group, with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is an aryl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^4R^5$ group; and and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^4R^5$ group; and and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is an phenyl group which is substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^4R^5$ group; and and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;

with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a $NR^7R^8$ group, with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom, and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

$R^3$ is selected from, a $C_1$-$C_6$-alkoxy group, a $C_2$-$C_6$-alkenyl group, a $C_3$-$C_6$-cycloalkyl group, a $C_5$-$C_6$-cycloalkenyl group, a 3- to 7-membered heterocycloalkyl group, which is optionally substituted with one, two, or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an phenyl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;

a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;

and a $NR^6R^7$ group, with the proviso that $R^3$ can not be imidazol-1-yl if $R^1$ and $R^2$ are a hydrogen atoms, with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom, and stereoisomers, tautomers, N-oxides, hydrates, solvates, and salts thereof, and mixtures of same.

In yet another embodiment of the first aspect, the present invention provides compounds of formula (I), supra, in which:

$R^3$ is selected from, a $C_3$-$C_6$-cycloalkyl group, a $C_5$-$C_6$-cycloalkenyl group, a 3- to 7-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;

a mono- or bicyclic heteroaryl group which is optionally substituted with one, two or three substituents and each substituent is independently selected from a halogen atom, a $C_1$-$C_3$-alkyl group, a cyano group, a $C_1$-$C_3$- haloalkyl group, a $C_1$-$C_3$-alkoxy group, a hydroxy group, and a $NR^4R^5$ group;
with the proviso that $R^3$ can not be imidazol-1-yl if $R^1$ and $R^2$ are a hydrogen atoms and $R^3$ can not be morpholin-4-yl if $R^1$ is a trifluoromethyl group and $R^2$ is a hydrogen atom,
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is selected from,
a $C_1$-$C_6$-alkoxy group,
a $C_2$-$C_6$-alkenyl group,
a hydroxy group, and a $NR^4R^5$ group;
and a $NR^6R^7$ group, with the proviso that $R^3$ can not be imidazol-1-yl if $R^1$ and $R^2$ are a hydrogen atoms,
and stereoisomers, tautomers, N-oxides, hydrates, solvates, and salts thereof, and mixtures of same.

In yet another embodiment of the first aspect, the present invention provides compounds of formula (I), supra, in which:
$R^3$ is selected from
an aryl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;
with the proviso that $R^3$ can not be imidazol-1-yl if $R^1$ and $R^2$ are a hydrogen atoms, and stereoisomers, tautomers, N-oxides, hydrates, solvates, and salts thereof,
and mixtures of same.

In yet another embodiment of the first aspect or any embodiment derived therefrom, the present invention provides compounds of formula (I), supra, in which:
$R^3$ is selected from
an phenyl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;
with the proviso that $R^3$ can not be imidazol-1-yl if $R^1$ and $R^2$ are a hydrogen atoms, and stereoisomers, tautomers, N-oxides, hydrates, solvates, and salts thereof,
and mixtures of same.

In yet another embodiment of the first aspect or any embodiment derived therefrom, the present invention provides compounds of formula (I), supra, in which:
$R^3$ is a 3- to 7-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, with the proviso that $R^3$ can not be morpholin-4-yl if $R^1$ is a trifluoromethyl group and $R^2$ is a hydrogen atom.

In another embodiment of the first aspect or any embodiment derived therefrom, the present invention provides compounds of formula (I), supra, in which:
$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^4/R^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^4/R^5$ is independently selected from a hydrogen atom and a $C_1$-$C_6$-alkyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which: $R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a $C_3$-$C_6$-cycloalkyl group, and a 3- to 5-membered heterocycloalkyl group,
or $R^6$ and $R^7$ together form a 3-, 4-, 5-, 6- or 7-membered ring optionally containing one or two additional heteroatoms selected from the group consisting of —O—, —S— and —$NR^8$—,
and which is optionally substituted one, two or three times with a substituent selected from a halogen atom, a hydroxy group and a $C_1$-$C_3$-alkyl group;
and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;
$R^8$ is a hydrogen atom or a $C_1$-$C_3$-alkyl group,
or a stereoisomer, a tautomer, an N-oxide, a hydrate, a solvate, or a salt thereof, or a mixture of same.

In another embodiment of the first aspect or any embodiment derived therefrom, the present invention provides compounds of formula (I), supra, in which: $R^6/R^7$ is independently selected from a hydrogen atom and a $C_1$-$C_6$-alkyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which: $R^6$ and $R^7$ together form a 3-, 4-, 5-, 6-membered ring optionally containing one or two additional heteroatoms selected from the group consisting of —O—, —S— and —$NR^8$—, where $R^8$ is a hydrogen atom or a $C_1$-$C_3$-alkyl group,
and which is optionally substituted one, two or three times, particularly one or two times, even more particularly one time with a substituent selected from a halogen atom and a $C_1$-$C_3$-alkyl group;

In a further embodiment of the first aspect or any embodiment derived therefrom, the present invention provides compounds of formula (I), supra, in which:

$R^6$ and $R^7$ together form a 5-, or 6-membered ring optionally containing one additional oxygen atom, which ring can optionally contain a bridging group selected from —O—, —NR$^8$—, —CH$_2$—, —CH$_2$—CH$_2$—, —O—CH$_2$—, —NR$^8$—CH$_2$—
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

or $R^6$ and $R^7$ together form a 4-, 5-, or 6-membered ring optionally containing one or two additional heteroatoms selected from the group consisting of —O—, —S— and —NR$^8$—, where $R^8$ is a hydrogen atom or a $C_1$-$C_3$-alkyl group,
and which is optionally substituted one, two or three times with a substituent selected from a halogen atom and a $C_1$-$C_3$-alkyl group;
and if $R^6$ and $R^7$ together form a 5-, 6- or 7-membered ring, said ring can optionally contain a bridging group selected from —O—, —NR$^8$—, —CH$_2$—, —CH$_2$—CH$_2$—, —O—CH$_2$—, —NR$^8$—CH$_2$—,
and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:

or $R^6$ and $R^7$ together form a 4-, 5-, or 6-membered ring optionally containing one additional oxygen atom,
and which is optionally substituted one or two times with a substituent selected from a halogen atom and a $C_1$-$C_3$-alkyl group;
and stereoisomers, tautomers, N-oxides, hydrates, solvates, and salts thereof, and mixtures of same.

In another aspect, the invention provides a pharmaceutical composition containing one or more pharmaceutically acceptable carriers or excipients and a compound of formula (I)
or stereoisomers, tautomers, N-oxides, hydrates, solvates, salts thereof, or mixtures of same.

In yet another aspect, the invention provides a pharmaceutical composition containing one or more pharmaceutically acceptable carriers or excipients and a compound of formula (I)
a pharmaceutically acceptable salt or prodrug thereof.

In a further aspect, the present invention provides methods of using the compounds of formula (I), supra, in which:

$R^1$ is selected from a hydrogen atom, a halogen atom, a cyano group, a $C_1$-$C_3$-alkyl group, a $C_1$-$C_3$-haloalkyl group, a $C_1$-$C_3$-haloalkoxy group;
$R^2$ is selected from a hydrogen atom and a halogen atom;
$R^3$ is selected from,
a $C_1$-$C_6$-alkoxy group,
a $C_2$-$C_6$-alkenyl group,
a $C_3$-$C_6$-cycloalkyl group,
a $C_5$-$C_6$-cycloalkenyl group,
a 3- to 7-membered heterocycloalkyl group, which is optionally substituted with one, two or three substituents and each substituent is independently selected
from a halogen atom, a $C_1$-$C_3$-alkyl group, a hydroxy group, NR$^4$R$^5$ group, a $C_1$-$C_3$-haloalkyl group and a $C_1$-$C_3$-haloalkoxy group,
a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^4$R$^5$ group,
and a NR$^6$R$^7$ group,
with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;
$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;
$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-NR$^8$—$C_1$-$C_5$-alkyl group, a —$C_1$-$C_5$-hydroxyalkylen-($C_1$-$C_3$-haloalkyl) group, a $C_3$-$C_6$-cycloalkyl group, and a 3- to 5-membered heterocycloalkyl group,
or $R^6$ and $R^7$ together form a 3-, 4-, 5-, 6- or 7-membered ring optionally containing one or two additional heteroatoms selected from the group consisting of —O—, —S— and —NR$^8$—,
and which is optionally substituted one, two, or three times with a substituent selected from a halogen atom, a hydroxy group, and a $C_1$-$C_3$-alkyl group
and if $R^6$ and $R^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
$R^8$ is a hydrogen atom or a $C_1$-$C_3$-alkyl group;
or a stereoisomer, a tautomer, an N-oxide, a hydrate, a solvate, or a salt thereof, or a mixture of same, for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:
$R^1$ is a trifluoromethyl group;
$R^2$ is selected from a hydrogen atom and a halogen atom;
$R^3$ is selected from,
a $C_1$-$C_6$-alkoxy group,
a $C_2$-$C_6$-alkenyl group,
a $C_3$-$C_6$-cycloalkyl group,
a $C_5$-$C_6$-cycloalkenyl group,
a 3- to 7-membered heterocycloalkyl group, which is optionally substituted with one, two or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group, and a $NR^6R^7$ group, with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;

$R^4/R^5$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, $C_3$-$C_6$-cycloalkyl group, and a 3- to 5-membered heterocycloalkyl group;

$R^6/R^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-alkylen-S—$C_1$-$C_5$-alkyl group, a —$C_1$-$C_5$-alkylen-$NR^8$—$C_1$-$C_5$-alkyl group, a —$C_1$-$C_5$-hydroxyalkylen-($C_1$-$C_3$-haloalkyl) group, a $C_3$-$C_6$-cycloalkyl group, and a 3- to 5-membered heterocycloalkyl group, or $R^6$ and $R^7$ together form a 3-, 4-, 5-, 6- or 7-membered ring optionally containing one or two additional heteroatoms selected from the group consisting of —O—, —S— and —$NR^8$—, and which is optionally substituted one, two, or three times with a substituent selected from a halogen atom, a hydroxy group, and a $C_1$-$C_3$-alkyl group and if $R^6$ and $R^7$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;

or a stereoisomer, a tautomer, an N-oxide, a hydrate, a solvate, or a salt thereof, or a mixture of same.

In a further aspect, the present invention provides methods of using the compounds of formula (I), supra, in which:

$R^1$ is selected from a hydrogen atom, a halogen atom, a $C_1$-$C_3$-alkyl group, a $C_1$-$C_3$-haloalkyl group, a $C_1$-$C_3$-haloalkoxy group;

$R^2$ is selected from a hydrogen atom and a halogen atom;

$R^3$ is selected from,
 a $C_1$-$C_6$-alkoxy group,
 a $C_2$-$C_4$-alkenyl group,
 a $C_5$-$C_6$-cycloalkenyl group,
 a 3- to 6-membered heterocycloalkyl group, which is optionally substituted with one or two substituents and each substituent is independently selected from a halogen atom and a $C_1$-$C_3$-alkyl group, a 5- to 6-membered heterocycloalkyl group which is partially unsaturated and optionally substituted with one or two substituents and each substituent is independently selected from an oxo group (=O), a $C_1$-$C_3$-alkyl group and a halogen atom, an aryl group which is optionally substituted with one, two or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^4R^5$ group, and a $NR^6R^7$ group, with the proviso that $R^3$ can not be imidazol-1-yl if $R^1$ and $R^2$ are a hydrogen atoms and $R^3$ can not be morpholin-4-yl, if $R^1$ is trifluoromethyl and $R^2$ is a hydrogen atom;

$R^4/R^5$ is independently selected from a hydrogen atom, a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, $C_3$-$C_6$-cycloalkyl group, and a 3- to 5-membered heterocycloalkyl group; and $R^6/R^7$ is independently selected from hydrogen atom, and a $C_1$-$C_6$-alkyl group, a —$C_1$-$C_3$-alkylen-O—$C_1$-$C_3$-alkyl group, a —$C_1$-$C_3$-alkylen-S—$C_1$-$C_3$-alkyl group, a —$C_1$-$C_3$-alkylen-$NR^8$—$C_1$-$C_3$-alkyl group, a —$C_1$-$C_3$-hydroxyalkylen-($C_1$-$C_3$-haloalkyl) group, a $C_3$-$C_6$-cycloalkyl group, a 3- to 5-membered heterocycloalkyl group, or $R^6$ and $R^7$ together form a 4-, 5-, or 6-membered ring optionally containing one or two additional heteroatoms selected from the group consisting of —O—, —S— and —$NR^8$—, and which is optionally substituted one, two or three times with a substituent selected from a halogen atom and a $C_1$-$C_3$-alkyl group;

and if $R^7$ and $R^8$ together form a 5-, 6- or 7-membered ring, said ring can optionally contain a bridging group selected from a bond, —O—, —$NR^8$—, —$CH_2$—, —$CH_2$—$CH_2$—, —O—$CH_2$—, —$NR^8$—$CH_2$—;

$R^8$ is a hydrogen atom or a $C_1$-$C_3$-alkyl group;

or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:

$R^1$ is selected from a hydrogen atom, a halogen atom, a cyano group, a $C_1$-$C_3$-alkyl group, a $C_1$-$C_3$-haloalkyl group;

$R^2$ is selected from a hydrogen atom and a halogen atom;

$R^3$ is selected,
 a $C_1$-$C_6$-alkoxy group,
 a $C_2$-$C_6$-alkenyl group,
 a $C_5$-$C_6$-cycloalkenyl group,
 a 3- to 7-membered heterocycloalkyl group, which is optionally substituted with one or two substituents and each substituent is independently selected from a halogen atom, a $C_1$-$C_3$-alkyl group, or a hydroxy group,
 a 5- to 7-membered heterocycloalkyl group which is partially unsaturated;

an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group;

a mono- or bicyclic heteroaryl group which is optionally substituted with one, or two substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group;

and a NR$^6$R$^7$ group;

with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;

R$^4$/R$^5$ is a hydrogen atom;

R$^6$/R$^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group, or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:

R$^1$ is selected from a hydrogen atom, a halogen atom, a cyano group, a $C_1$-$C_3$-alkyl group, a $C_1$-$C_3$-haloalkyl group;

R$^2$ is selected from a hydrogen atom and a halogen atom;

R$^3$ is selected from,
 a $C_2$-$C_6$-alkenyl group,
 a $C_5$-$C_6$-cycloalkenyl group,
 a 3- to 7-membered heterocycloalkyl group, which is optionally substituted with one or two substituents and each substituent is independently selected from a halogen atom, a $C_1$-$C_3$-alkyl group, or a hydroxy group,
 a 5- to 7-membered heterocycloalkyl group which is partially unsaturated;
 an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a —C(O)NR$^4$R$^5$ group and a NR$^4$R$^5$ group;
 a mono- or bicyclic heteroaryl group which is optionally substituted with one, or two substituents and each substituent is independently selected from a halogen atom, a $C_1$-$C_3$-alkyl group;
 and a NR$^6$R$^7$ group;
 with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;

R$^4$/R$^5$ is a hydrogen atom;

R$^6$/R$^7$ is independently selected from a hydrogen atom, a $C_1$-$C_6$-alkyl group, a —$C_1$-$C_5$-alkylen-O—$C_1$-$C_5$-alkyl group, a —$C_1$-$C_5$-hydroxyalkylen-$C_1$-$C_3$-haloalkyl group;

or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:

R$^1$ is selected from a hydrogen atom, a halogen atom, a cyano group, a $C_1$-$C_3$-alkyl group, a $C_1$-$C_3$-haloalkyl group;

R$^2$ is selected from a hydrogen atom and a halogen atom;

R$^3$ is selected from,
 a $C_2$-$C_6$-alkenyl group,
 a $C_5$-$C_6$-cycloalkenyl group,
 a 3- to 7-membered heterocycloalkyl group, which is optionally substituted with one or two substituents and each substituent is independently selected from a halogen atom, a $C_1$-$C_3$-alkyl group, or a hydroxy group,
 a 5- to 7-membered heterocycloalkyl group which is partially unsaturated;
 an aryl group which is optionally substituted with one, or two substituents and each substituent is independently selected from a halogen atom, a hydroxy group, a cyano group, a $C_1$-$C_3$-alkyl group, a $C_1$-$C_3$-alkoxy group, a —C(O)NR$^4$R$^5$ group and a NR$^4$R$^5$ group;
 a monocyclic heteroaryl group which is optionally substituted with one or two substituents and each substituent is independently selected from a halogen atom, a $C_1$-$C_3$-alkyl group;
 and a NR$^6$R$^7$ group;
 with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;

R$^4$/R$^5$ is a hydrogen atom;

R$^6$/R$^7$ is independently selected from a hydrogen atom or a —$C_1$-$C_5$-alkylen-O—$C_1$-$C_5$-alkyl group;

or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:

R$^1$ is selected from a halogen atom, a $C_1$-$C_3$-alkyl group and a $C_1$-$C_3$-haloalkyl group;

R$^2$ is selected from a hydrogen atom and a halogen atom;

R$^3$ is selected from,
 a $C_1$-$C_3$-alkoxy group,
 a $C_2$-$C_4$-alkenyl group
 a $C_5$-$C_6$-cycloalkenyl group,
 a 3- to 6-membered heterocycloalkyl group, which is optionally substituted with one or two substituents and each substituent is independently selected from a halogen atom, a hydroxy group and a $C_1$-$C_3$-alkyl group,
 a 5- to 6-membered heterocycloalkyl group which is partially unsaturated,
 an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)NR$^4$R$^5$ group and a NR$^4$R$^5$ group,
 a mono- or bicyclic heteroaryl group which is optionally substituted with one, two or three substituents and each substituent is independently selected from a halogen atom, a $C_1$-$C_3$-alkyl group, a $C_1$-$C_3$-haloalkyl group, a $C_1$-$C_3$-alkoxy group, and a NR$^4$R$^5$ group,
 and a NR$^6$R$^7$ group,
 with the proviso that R$^3$ can not be imidazol-1-yl if R$^1$ and R$^2$ are a hydrogen atoms and R$^3$ can not be morpholin-4-yl, if R$^1$ is trifluoromethyl and R$^2$ is a hydrogen atom;

R$^4$/R$^5$ is independently selected from a hydrogen atom and a $C_1$-$C_3$-alkyl group; and R⁶/R⁷ is independently selected from a hydrogen atom, a C₁-C₆-alkyl group, a —C₁-C₅-alkylen-O—C₁-C₅-alkyl group, and a —C₁-C₅-hydroxyalkylen-C₁-C₃-haloalkyl group;
or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:
R¹ is selected from a hydrogen atom, a trifluoromethyl group, a fluorine atom, a chlorine atom, a methyl group, a cyano group,
R² is a hydrogen atom, a fluorine atom,
R³ is selected from,
  a methoxy group,
  a 2-methylprop-1-en-1-yl group,
  a -(2E)-but-2-en-2-yl group,
  a cyclopent-1-en-1-yl group,
  a cyclohex-1-en-1-yl group,
  a 3,6-dihydro-2H-pyran-4-yl group,
  a tetrahydropyran-4-yl group,
  a azetidin-1-yl group which is substituted with two halogen atoms or a hydroxy group,
  a 3-azabicyclo[3.1.1]hept-3-yl group which is substituted with two halogen atoms
  a 3-azabicyclo[3.1.0]hex-3-yl group which is optionally substituted with a methyl group,
  a piperidin-1-yl group which is optionally substituted with one or two halogen atoms
  a morpholin-4-yl group,
  a pyrrolidin-1-yl group which is substituted with a methyl group,
  a phenyl group which is optionally substituted with one, two or three substituents and each substituent is independently selected from a halogen atom, a hydroxy group, a methyl group, an ethyl group, a CF₃ group, a cyano group, a methoxy group, a ethoxy group, a —OCF₃ group, a NH₂ group and a C(O)NH₂ group,
  a 1H-pyrazol-4-yl group, which is optionally substituted with a difluoromethyl group,
  a 1H-pyrazol-1-yl group, which is optionally substituted with a trifluoromethyl group,
  a furan-3-yl group,
  a pyridin-3-yl and a pyridin-4-yl group each group being optionally substituted with one or two substituents and each substituent is independently selected from a halogen atom, a methyl group, a trifluoromethyl group, a methoxy group and a NH₂ group,
  a pyrimidin-5-yl group, which is optionally substituted with a methyl group, a NH₂ group,
  a 1H-indol-6-yl group, a 1H-indol-4-yl group,
  a —NHCH₃ group, a —NH(C₂H₅) group, a —NH—(CH₂)₂—O—CH₃ group, a —NH—CH₂—CH(OH)—CF₃ group;
with the proviso that R³ can not be morpholin-4-yl, if R¹ is trifluoromethyl and R² is a hydrogen atom
or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

In a further aspect, the present invention provides methods of using the compounds of formula (I), supra, in which:
6-[4-(3,6-Dihydro-2H-pyran-4-yl)phenyl]-4,5-dihydropyridazin-3(2H)-one,
6-[3-Methyl-4-(pyridin-3-yl)phenyl]-4,5-dihydropyridazin-3(2H)-on,
6-(4'-Fluoro-2-methylbiphenyl-4-yl)-4,5-dihydropyridazin-3(2H)-one,
6-(4'-Fluoro-2,2'-dimethylbiphenyl-4-yl)-4,5-dihydropyridazin-3(2H)-one,
6-[3-Methyl-4-(pyridin-4-yl)phenyl]-4,5-dihydropyridazin-3(2H)-one,
6-[3-Methyl-4-(1H-pyrazol-4-yl)phenyl]-4,5-dihydropyridazin-3(2H)-one,
6-[4-(3,6-Dihydro-2H-pyran-4-yl)-3-methylphenyl]-4,5-dihydropyridazin-3(2H)-one,
6-(2,4'-Difluorobiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-[4-(4,4-Difluoropiperidin-1-yl)-3,5-difluorophenyl]-4,5-dihydropyridazin-3(2H)-one,
6-[4-(3,3-Difluoropyrrolidin-1-yl)-3,5-difluorophenyl]-4,5-dihydropyridazin-3(2H)-one,
-[4-(3-Azabicyclo[3.1.0]hex-3-yl)-3,5-difluorophenyl]-4,5-dihydropyridazin-3(2H)-one,
2-(Morpholin-4-yl)-5-(6-oxo-1,4,5,6-tetrahydropyridazin-3-yl)benzonitrile,
6-[3,5-Difluoro-4-(piperidin-1-yl)phenyl]-4,5-dihydropyridazin-3(2H)-one,
6-{3,5-Difluoro-4-[2-methyl-3-azabicyclo[3.1.0]hex-3-yl]phenyl}-4,5-dihydropyridazin-3(2H)-one
6-[4-(Ethylamino)-3-(trifluoromethyl)phenyl]-4,5-dihydropyridazin-3(2H)-one,
6-[4-(3,3-Difluoroazetidin-1-yl)-3-(trifluoromethyl)phenyl]-4,5-dihydropyridazin-3(2H)-one,
6-{4-[2-Methylpyrrolidin-1-yl]-3-(trifluoromethyl)phenyl}-4,5-dihydropyridazin-3(2H)-one,
6-[4-(6,6-Difluoro-3-azabicyclo[3.1.1]hept-3-yl)-3-(trifluoromethyl)phenyl]-4,5-dihydropyridazin-3(2H)-one,
6-[4-(3,3-Difluoropyrrolidin-1-yl)-3-(trifluoromethyl)phenyl]-4,5-dihydropyridazin-3(2H)-one,
6-[4-(Methylamino)-3-(trifluoromethyl)phenyl]-4,5-dihydropyridazin-3(2H)-one,
6-[4-(3-Hydroxyazetidin-1-yl)-3-(trifluoromethyl)phenyl]-4,5-dihydropyridazin-3(2H)-one,
6-[3-Fluoro-4-(morpholin-4-yl)phenyl]-4,5-dihydropyridazin-3(2H)-one,
6-(4'-Fluoro-2'-methylbiphenyl-4-yl)-4,5-dihydropyridazin-3(2H)-one,
6-[3-Fluoro-4-(2-methylprop-1-en-1-yl)phenyl]-4,5-dihydropyridazin-3(2H)-one,
6-[4-(2-Aminopyridin-4-yl)-3-fluorophenyl]-4,5-dihydropyridazin-3(2H)-one,
6-{3-Fluoro-4-[5-(trifluoromethyl)pyridin-3-yl]phenyl}-4,5-dihydropyridazin-3(2H)-one,
6-[3-Fluoro-4-(pyridin-4-yl)phenyl]-4,5-dihydropyridazin-3(2H)-one,
6-[3-Fluoro-4-(2-methylpyrimidin-5-yl)phenyl]-4,5-dihydropyridazin-3(2H)-one,
6-[3-Fluoro-4-(2-methoxypyridin-4-yl)phenyl]-4,5-dihydropyridazin-3(2H)-one,
6-[3-Fluoro-4-(2-methylpyridin-3-yl)phenyl]-4,5-dihydropyridazin-3(2H)-one,
6-[3-Fluoro-4-(6-methylpyridin-3-yl)phenyl]-4,5-dihydropyridazin-3(2H)-one,
6-(2-Fluoro-3',4-dimethylbiphenyl-4-yl)-4,5-dihydropyridazin-3(2H)-one,
6-{4-[(2E)-But-2-en-2-yl]-3-fluorophenyl}-4,5-dihydropyridazin-3(2H)-one 6-(2,2'-Difluoro-4-methylbiphenyl-4-yl)-4,5-dihydropyridazin-3(2H)-one,
6-(2,2',4,5-Tetrafluorobiphenyl-4-yl)-4,5-dihydropyridazin-3(2H)-one,
6-(2,2',3,4-Tetrafluorobiphenyl-4-yl)-4,5-dihydropyridazin-3(2H)-one
6-[3-Fluoro-4-(pyrimidin-5-yl)phenyl]-4,5-dihydropyridazin-3(2H)-one,
6-(2-Fluoro-2',5-dimethoxybiphenyl-4-yl)-4,5-dihydropyridazin-3(2H)-one,
6-(2,2',5-Trifluorobiphenyl-4-yl)-4,5-dihydropyridazin-3(2H)-one,
6-(2'-Amino-2,5-difluorobiphenyl-4-yl)-4,5-dihydropyridazin-3(2H)-one,
6-[2-Fluoro-2'-(trifluoromethoxy)biphenyl-4-yl]-4,5-dihydropyridazin-3(2H)-one,
6-[3-Fluoro-4-(furan-3-yl)phenyl]-4,5-dihydropyridazin-3(2H)-one,
2'-Fluoro-4'-(6-oxo-1,4,5,6-tetrahydropyridazin-3-yl)biphenyl-4-carbonitrile
2'-Fluoro-4'-(6-oxo-1,4,5,6-tetrahydropyridazin-3-yl)biphenyl-3-carbonitrile,
6-(3'-Amino-2-fluoro-4'-methyl biphenyl-4-yl)-4,5-dihydropyridazin-3(2H)-one
6-(2-Fluoro-3'-hydroxybiphenyl-4-yl)-4,5-dihydropyridazin-3(2H)-one,
-(2-Fluoro-2'-hydroxybiphenyl-4-yl)-4,5-dihydropyridazin-3(2H)-one,
6-(2,3',4-Trifluorobiphenyl-4-yl)-4,5-dihydropyridazin-3(2H)-one,
6-(2'-Ethoxy-2-fluorobiphenyl-4-yl)-4,5-dihydropyridazin-3(2H)-one,
6-(2,2',3-Trifluorobiphenyl-4-yl)-4,5-dihydropyridazin-3(2H)-one,
6-(2,3',5-Trifluorobiphenyl-4-yl)-4,5-dihydropyridazin-3(2H)-one,
6-(2,2',4-Trifluorobiphenyl-4-yl)-4,5-dihydropyridazin-3(2H)-one,
6-(2-Fluoro-2',4-dimethylbiphenyl-4-yl)-4,5-dihydropyridazin-3(2H)-one,
6-(2,5'-Difluoro-2'-methylbiphenyl-4-yl)-4,5-dihydropyridazin-3(2H)-one,
6-(2,3'-Difluoro-4-methylbiphenyl-4-yl)-4,5-dihydropyridazin-3(2H)-one,
6-(3'-Amino-4'-chloro-2-fluorobiphenyl-4-yl)-4,5-dihydropyridazin-3(2H)-one,
6-(2,2'-Difluorobiphenyl-4-yl)-4,5-dihydropyridazin-3(2H)-one,
6-[2-Fluoro-2'-(trifluoromethyl) biphenyl-4-yl]-4,5-dihydropyridazin-3(2H)-one,
6-(2-Fluoro-2'-methoxybiphenyl-4-yl)-4,5-dihydropyridazin-3(2H)-one,
6-(2,3'-Difluorobiphenyl-4-yl)-4,5-dihydropyridazin-3(2H)-one,
6-(2-Fluoro-3'-methoxybiphenyl-4-yl)-4,5-dihydropyridazin-3(2H)-one,
6-(3'-Amino-2-fluorobiphenyl-4-yl)-4,5-dihydropyridazin-3(2H)-one,
6-(2'-Amino-2-fluorobiphenyl-4-yl)-4,5-dihydropyridazin-3(2H)-one,
6-[3-Fluoro-4-(4-methylpyridin-3-yl)phenyl]-4,5-dihydropyridazin-3(2H)-one,
6-(2,2'-Difluoro-5'-methylbiphenyl-4-yl)-4,5-dihydropyridazin-3(2H)-one,
6-[4-(3-Chloropyridin-4-yl)-3-fluorophenyl]-4,5-dihydropyridazin-3(2H)-one,
6-[3-Fluoro-4-(2-methoxypyridin-3-yl)phenyl]-4,5-dihydropyridazin-3(2H)-one,
6-[3-Fluoro-4-(6-fluoropyridin-3-yl)phenyl]-4,5-dihydropyridazin-3(2H)-one,
6-[3-Fluoro-4-(2-fluoropyridin-3-yl)phenyl]-4,5-dihydropyridazin-3(2H)-one,
6-[3-Fluoro-4-(3-methylpyridin-4-yl)phenyl]-4,5-dihydropyridazin-3(2H)-one,
6-[3-Fluoro-4-(1H-indol-6-yl)phenyl]-4,5-dihydropyridazin-3(2H)-one,
6-[3-Fluoro-4-(1H-indol-4-yl)phenyl]-4,5-dihydropyridazin-3(2H)-one,
6-(4'-Amino-2-fluorobiphenyl-4-yl)-4,5-dihydropyridazin-3(2H)-one,
6-(2-Fluoro-2'-methylbiphenyl-4-yl)-4,5-dihydropyridazin-3(2H)-one,
6-(2-Fluoro-2',3-dimethoxybiphenyl-4-yl)-4,5-dihydropyridazin-3(2H)-one,
6-[4-(Cyclohex-1-en-1-yl)-3-fluorophenyl]-4,5-dihydropyridazin-3(2H)-one,
6-[4-(Cyclopent-1-en-1-yl)-3-fluorophenyl]-4,5-dihydropyridazin-3(2H)-one,
6-(2'-Ethyl-2-fluorobiphenyl-4-yl)-4,5-dihydropyridazin-3(2H)-one,
6-[3-Fluoro-4-(6-methoxypyridin-3-yl)phenyl]-4,5-dihydropyridazin-3(2H)-one,
6-(3'-Chloro-2,4-difluorobiphenyl-4-yl)-4,5-dihydropyridazin-3(2H)-one,
6-(2,4'-Difluoro-3-methylbiphenyl-4-yl)-4,5-dihydropyridazin-3(2H)-one,
6-(2-Fluoro-2',3-dimethylbiphenyl-4-yl)-4,5-dihydropyridazin-3(2H)-one,
6-(2-Fluoro-4'-methoxybiphenyl-4-yl)-4,5-dihydropyridazin-3(2H)-one,
6-(2-Fluoro-4'-methylbiphenyl-4-yl)-4,5-dihydropyridazin-3(2H)-one,
6-(2-Fluoro-2',5-dimethylbiphenyl-4-yl)-4,5-dihydropyridazin-3(2H)-one,
2',6-Difluoro-4'-(6-oxo-1,4,5,6-tetrahydropyridazin-3-yl)biphenyl-3-carbonitrile,
6-[4-(2-Aminopyridin-4-yl)-3-methylphenyl]-4,5-dihydropyridazin-3(2H)-one,
6-[4-(2-Aminopyrimidin-5-yl)-3-methylphenyl]-4,5-dihydropyridazin-3(2H)-one,
6-[3-Methyl-4-(2-methylpyrimidin-5-yl)phenyl]-4,5-dihydropyridazin-3(2H)-one,
6-[3-Methyl-4-(6-methylpyridin-3-yl)phenyl]-4,5-dihydropyridazin-3(2H)-one,
6-(2'-Fluoro-2,4-dimethylbiphenyl-4-yl)-4,5-dihydropyridazin-3(2H)-one,
6-(2',4,5-Trifluoro-2-methylbiphenyl-4-yl)-4,5-dihydropyridazin-3(2H)-one,
6-(3',4,5-Trifluoro-2-methylbiphenyl-4-yl)-4,5-dihydropyridazin-3(2H)-one,
6-(2',3,4-Trifluoro-2-methylbiphenyl-4-yl)-4,5-dihydropyridazin-3(2H)-one,
6-(2',5-Difluoro-2-methylbiphenyl-4-yl)-4,5-dihydropyridazin-3(2H)-one,
2'-Methyl-4'-(6-oxo-1,4,5,6-tetrahydropyridazin-3-yl)biphenyl-2-carbonitrile,
2'-Methyl-4'-(6-oxo-1,4,5,6-tetrahydropyridazin-3-yl)biphenyl-4-carbonitrile,
6-(3'-Hydroxy-2-methylbiphenyl-4-yl)-4,5-dihydropyridazin-3(2H)-one,
6-(2'-Hydroxy-2-methylbiphenyl-4-yl)-4,5-dihydropyridazin-3(2H)-one, 6-(3'-Amino-2-methylbiphenyl-4-yl)-4,5-dihydropyridazin-3(2H)-one,
-(2',3-Difluoro-2-methylbiphenyl-4-yl)-4,5-dihydropyridazin-3(2H)-one,
6-(3',5-Difluoro-2-methylbiphenyl-4-yl)-4,5-dihydropyridazin-3(2H)-one,
6-(2',4-Difluoro-2-methylbiphenyl-4-yl)-4,5-dihydropyridazin-3(2H)-one,
6-(3'-Fluoro-2,4-dimethylbiphenyl-4-yl)-4,5-dihydropyridazin-3(2H)-one,
6-(3'-Amino-4'-chloro-2-methylbiphenyl-4-yl)-4,5-dihydropyridazin-3(2H)-one,
6-(2'-Fluoro-2-methylbiphenyl-4-yl)-4,5-dihydropyridazin-3(2H)-one,
6-(2',6'-Difluoro-2-methylbiphenyl-4-yl)-4,5-dihydropyridazin-3(2H)-one,
6-(2'-Methoxy-2-methylbiphenyl-4-yl)-4,5-dihydropyridazin-3(2H)-one,
6-(3'-Fluoro-2-methylbiphenyl-4-yl)-4,5-dihydropyridazin-3(2H)-one,
6-(3'-Methoxy-2-methylbiphenyl-4-yl)-4,5-dihydropyridazin-3(2H)-one,
2'-Methyl-4'-(6-oxo-1,4,5,6-tetrahydropyridazin-3-yl)biphenyl-3-carboxamide,
6-(4'-Amino-2-methylbiphenyl-4-yl)-4,5-dihydropyridazin-3(2H)-one,
6-(2,2'-Dimethylbiphenyl-4-yl)-4,5-dihydropyridazin-3(2H)-one,
6-(2'-Ethyl-2-methylbiphenyl-4-yl)-4,5-dihydropyridazin-3(2H)-one,
6-[4-(6-Methoxypyridin-3-yl)-3-methylphenyl]-4,5-dihydropyridazin-3(2H)-one,
6-(4'-Fluoro-2,3'-dimethylbiphenyl-4-yl)-4,5-dihydropyridazin-3(2H)-one,
6-(2,3'-Dimethylbiphenyl-4-yl)-4,5-dihydropyridazin-3(2H)-one,
6-(2,4'-Dimethylbiphenyl-4-yl)-4,5-dihydropyridazin-3(2H)-one,
6-(4'-Chloro-2-methylbiphenyl-4-yl)-4,5-dihydropyridazin-3(2H)-one,
6-(4-Morpholinophenyl)-4,5-dihydropyridazin-3(2H)-one,
6-(3,5-Dichloro-4-morpholinophenyl)-4,5-dihydropyridazin-3(2H)-one,
6-{4-[1-(difluoromethyl)-1H-pyrazol-4-yl]-3-(trifluoromethyl)phenyl}-4,5-dihydropyridazin-3(2H)-one,
6-[4'-fluoro-2-(trifluoromethyl)[1,1'-biphenyl]-4-yl]-4,5-dihydropyridazin-3(2H)-one,
6-{4-[(2-methoxyethyl)amino]-3-(trifluoromethyl)phenyl}-4,5-dihydropyridazin-3(2H)-one,
6-[4-{[3,3,3-trifluoro-2-hydroxypropyl]amino}-3-(trifluoromethyl)phenyl]-4,5-dihydropyridazin-3(2H)-one (racemic) and
6-{3-fluoro-4-[3-(trifluoromethyl)-1H-pyrazol-1-yl]phenyl}-4,5-dihydropyridazin-3(2H)-one or a stereoisomer, a tautomer, an N-oxide, a hydrate, a solvate, or a salt thereof, or a mixture of same for the treatment of a hyperproliferative disease, especially cancer, more specifically the cancer diseases include solid tumors, lymphoma, sarcoma and leukemia.

The method above applies for all exemplified compounds disclosed herein.

"Reference" in this context means an average expression in a representative panel of tumor cells or tumor cell lines.

In various embodiments of any aspect delineated herein, the cancer is responsive to a PDE3A- and/or PDE3B-SLFN12 complex modulator.

In various embodiments, the subject has been diagnosed with a cancer responsive to a PDE3A- and/or PDE3B-SLFN12 complex modulator.

In various embodiments, the cancer is a melanoma, endometrium, lung, hematopoetic/lymphoid, ovarian, cervical, soft-tissue sarcoma, leiomyosarcoma, urinary tract, pancreas, thyroid, kidney, glioblastoma, or breast cancer.

In various embodiments, the cancer is a skin cancer, especially melanoma, lung adenocarcinoma or a cervical cancer.

In various embodiments of any aspect delineated herein, the PDE3A- and/or PDE3B-SLFN12 complex modulator is administered orally.

In various embodiments of any aspect delineated herein, the PDE3A- and/or PDE3B-SLFN12 complex modulator is administered by intravenous injection.

The invention provides methods for treating subjects having cancer identified as responsive to treatment with a PDE3A- and/or PDE3B-SLFN12 complex modulator of formula (I) by detecting co-expression of PDE3A and/or PDE3B and Schlafen 12 (SLFN12) polynucleotides or polypeptides and/or a lack of decrease in expression of CREB3L1 polynucleotides or polypeptides in the cancer.

Compositions and articles defined by the invention were isolated or otherwise manufactured in connection with the examples provided below. Other features and advantages of the invention will be apparent from the detailed description, and from the claims.

In a particular further embodiment of the first aspect, the present invention provides combinations of two or more of the above mentioned embodiments under the heading "further embodiments of the first aspect of the present invention".

The present invention provides any sub-combination within any embodiment or aspect of the present invention of compounds of general formula (I), supra.

The present invention provides any sub-combination within any embodiment or aspect of the present invention of intermediate compounds of general formula (I).

The present invention provides the compounds of general formula (I) which are disclosed in the Example Section of this text, infra.

Kits

The invention further provides kits comprising a compound of formula (I) and/or means for characterizing the responsiveness or resistance of a subject to PDE3-SLFN12 complex modulator, especially to compounds of formula (I) treatment.

Also provided herein are kits that can include the compound of formula (I) in form of a therapeutic composition containing an effective amount of said compound in e.g., a unit dosage form.

In some embodiments, the kit comprises a sterile container which includes a therapeutic or diagnostic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

In one embodiment, if desired, the kit further comprises instructions for measuring PDE3A/PDE3B and/or SLFN12 and/or instructions for administering the PDE3-SLFN12 complex modulator to a subject having a malignancy, e.g., a malignancy selected as responsive to PDE3-SLFN12 complex modulator treatment.

In particular embodiments, the instructions include at least one of the following: description of the therapeutic agent; dosage schedule and administration for treatment or prevention of malignancy or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of the invention.

General Synthesis of the Compounds of Formula (I)

The compounds according to the invention of general formula (I) can be prepared according to the following schemes 1, 2, 3, 4 and 5. The schemes and procedures described below illustrate synthetic routes to the compounds of general formula (I) of the invention and are not intended to be limiting. It is clear to the person skilled in the art that the order of transformations as exemplified in schemes 1, 2, 3, 4 and 5. can be modified in various ways. The order of transformations exemplified in these schemes is therefore not intended to be limiting. In addition, interconversion of any of the substituents, $R^1$, $R^2$, and $R^3$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Five routes for the preparation of compounds of general formula (I) are described in schemes 1, 2, 3, 4 and 5.

Synthesis Routes

The present invention provides methods of preparing compounds of the present invention of general formula (I), said methods comprising the steps as described in the Experimental Section herein.

Scheme 1

Synthesis of compounds of formula (I) by late introduction of $R^3$ (i), X=F, Cl/Br, I, (as reflected in Scheme 2)

and if X=Cl, Br, I, $R^1/R^2$ can not be Cl, Br, I and if X=F, $R^1/R^2$ are as defined in claim 1)

Synthesis of compounds of formula (II), Part I:

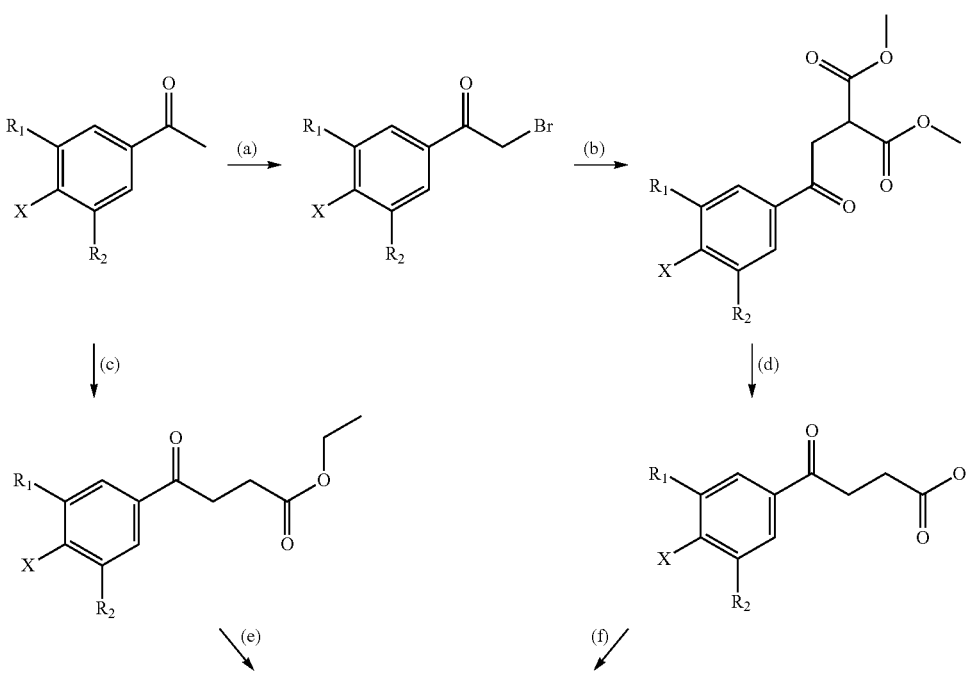

Scheme 1

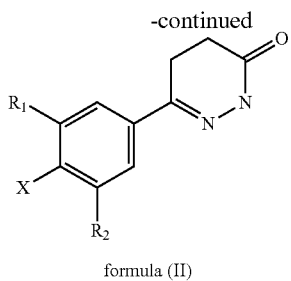

formula (II)

Scheme 1: Route for the preparation of compounds of general formula (II) in which $R^1$ and $R^2$ have the meaning as defined supra.

(a) acetic acid, bromine, hydrogen bromide, 18 h, RT: (b) dimethyl propanedioate, acetone, potassium carbonate, RT, 18 h; (c) LiHMDS, THF, −78° C., then BrCH$_2$COOEt, −78° C. to RT; (d) conc. aqueous hydrochloric acid, 100° C., 3 d; (e) hydrazine, EtOH, reflux, 6 h, or 1-propanol, hydrazine hydrate (1:1), 100° C., 18 h, or hydrazine hydrate (1:1), 100° C., 18 h; (f) hydrazine, EtOH, ref lux, 6 h, or 1-propanol, hydrazine hydrate (1:1), 100° C., 18 h, or hydrazine hydrate (1:1), 100° C., 18 h. Final products containing chiral centers can be optionally separated by any known method such as e.g. chiral chromatography to obtain individual enantiomers or diastereomers.

Conversion of the Compound of Formula (II) into a Compound of Formula (I): Part II:

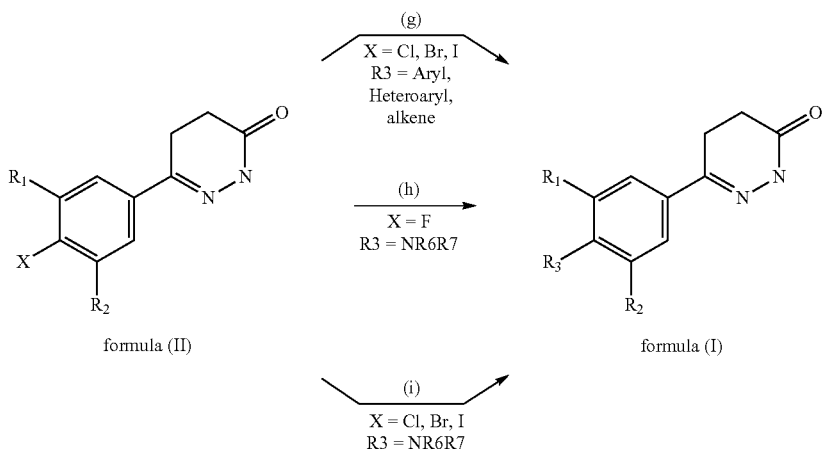

Scheme 2: Route for the preparation of compounds of general formula (I) via formula (II) in which $R^1$ and $R^2$ have the meaning as defined supra.

(g) $R^x$B(OH)$_2$ or $R^x$-boronic esters, potassium carbonate, 2-(Dicyclohexylphosphino)-2',4',6'-triisopropylbiphenyl, Chloro(2-dicyclohexylphosphino-2',4',6'-triisopropyl-1,1'-biphenyl)[2-(2'-amino-1,1'-biphenyl)]palladium(II), water, nitrogen atmosphere, 80° C.-120° C., 2 h-7 d, or $R^x$B(OH)$_2$ or $R^x$-boronic esters, potassium carbonate, dicyclohexyl[2',4',6'-tri(propan-2-yl)biphenyl-2-yl]phosphane, chloro(2-dicyclohexylphosphino-2',4',6'-triisopropyl-1,1'-biphenyl)[2-(2'-amino-1,1'-biphenyl)]palladium(II), dioxane, 100° C., 16 h;

$R^x$ is a C$_1$-C$_6$-alkoxy group,
a C$_2$-C$_6$-alkenyl group,
a C$_3$-C$_6$-cycloalkyl group,
a C$_5$-C$_6$-cycloalkenyl group, a 3- to 7-membered heterocycloalkyl group, which is optionally substituted with one, two, or three substituents and each substituent is independently selected from a halogen atom, a C$_1$-C$_3$-alkyl group, a hydroxy group, NR$^4$R$^5$ group, a C$_1$-C$_3$-haloalkyl group and a C$_1$-C$_3$-haloalkoxy group, a 5- to 7-membered heterocycloalkyl group which is partially unsaturated and optionally substituted with one, two or three substituents and each substituent is independently selected from an oxo group (=O), a C$_1$-C$_3$-alkyl group and a halogen atom, an aryl group which is optionally substituted with one, two, three or four substituents and each substituent is independently selected from a halogen atom, a hydroxy group, a cyano group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, a —C(O)NR$^4$R$^5$ group and a NR$^4$R$^5$ group;

a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, a hydroxy group, and a NR$^4$R$^5$ group;

and a NR$^6$R$^7$ group, R$^y$ is C$_1$-C$_6$-alkyl, or the two residues R$^y$ together form a pinacol ester (h) HNR$_7$R$_8$, triethylamine, 60-150° C., 6 h to 7 d, or HNR$_7$R$_8$, DIPEA, CH$_3$CN, reflux, or HNR$_7$R$_8$ (neat), NaHCO$_3$, 120° C., 5 h; (i) HNR$_7$R$_8$, 2-Dicyclohexylphosphino-2',6'-diisopropoxybiphenyl, Lithium bis(trimethylsilyl)amide, Dicyclolhexylphosphino-2',6'-diisopropyl-1,1'-biphenyl)(2-(2-aminoethyl)phenyl)palladium(II), nitrogen atmosphere, 60° C.-120° C., 2 h-7 d. Final products containing chiral centers can be optionally separated by chiral chromatography to obtain individual enantiomers or diastereomers.

Scheme 3: Intermediate Introduction of R³:

Scheme 3

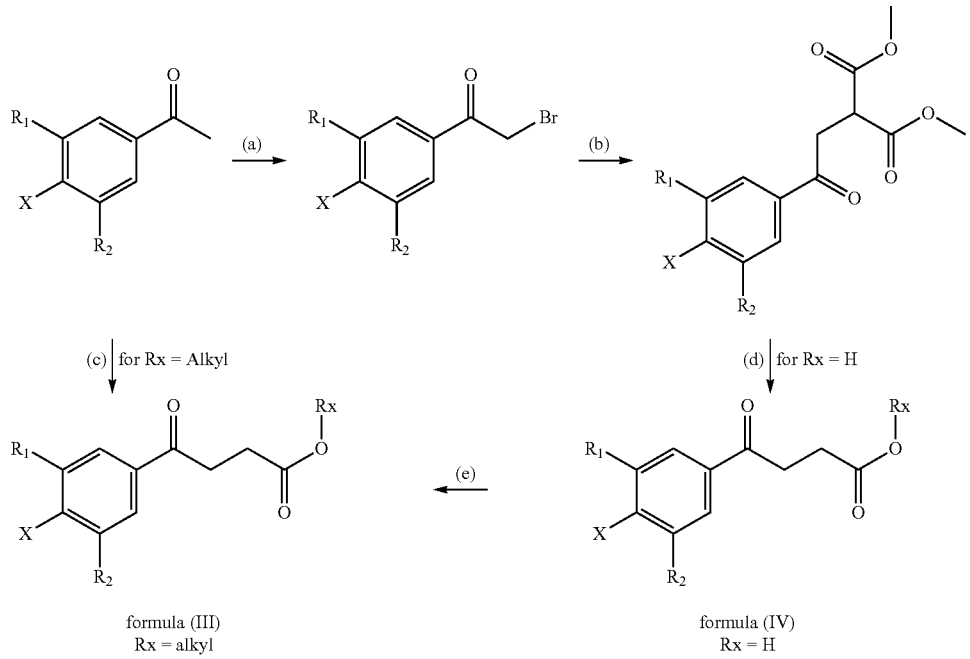

formula (III)
Rx = alkyl formula (IV)
Rx = H

Scheme 3: Route for the preparation of compounds of general formula (III) and formula (IV) in which R¹ and R² have the meaning as defined supra.

(a) acetic acid, bromine, hydrogen bromide, 18 h, RT: (b) dimethyl propanedioate, acetone, potassium carbonate, RT, 18 h; (c) LiHMDS, THF, −78° C., then BrCH₂COOEt, −78° C. to RT; (d) conc. aqueous hydrochloric acid, 100° C., 3 d; (e) MeOH, H₂SO₄, reflux, 15-20 h. (m) NaOCl, HOAc, 1 h, RT. Final products containing chiral centers can be optionally separated by any known method such as e.g. chiral chromatography to obtain individual enantiomers or diastereomers.

Conversion of the Compounds of Formulae (III and IV) into a Compound of Formula (I): Part II:

Scheme 4

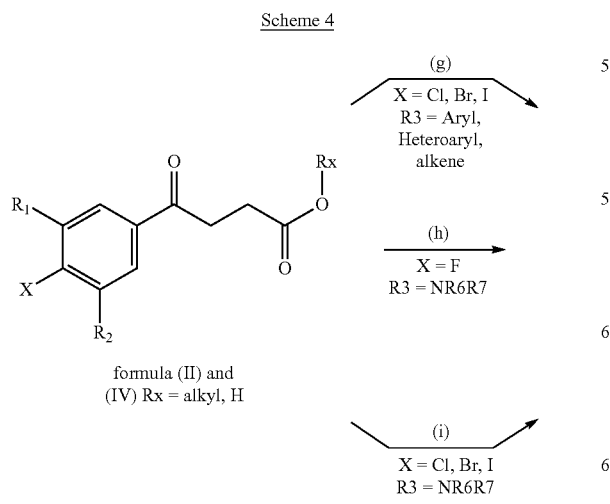

formula (II) and
(IV) Rx = alkyl, H formula (V)

formula (I)

Scheme 4: Route for the preparation of compounds of general formula (I) via formula (III) and formula (IV) in which R¹ and R² have the meaning as defined supra.

(f) hydrazine, EtOH, reflux, 6 h, or 1-propanol, hydrazine hydrate (1:1), 100° C., 18 h, or hydrazine hydrate (1:1), 100° C., 18 h (g) R$^x$B(OH)₂ or R$^x$-boronic esters, potassium carbonate, 2-(Dicyclohexylphosphino)-2',4',6'-triisopropylbiphenyl, Chloro(2-dicyclohexylphosphino-2',4',6'-triisopropyl-1,1'-biphenyl)[2-(2'-amino-1,1'-biphenyl)]palladium (II), water, nitrogen atmosphere, 80° C.-120° C., 2 h-7 d, or R$^x$B(OH)₂ or R$^x$-boronic esters, potassium carbonate, dicyclohexyl[2',4',6'-tri(propan-2-yl)biphenyl-2-yl]phosphane, chloro(2-dicyclohexylphosphino-2',4',6'-triisopropyl-1,1'- biphenyl)[2-(2'-amino-1,1'-biphenyl)]palladium(II), dioxane, 100° C., 16 h; (h) HNR$_7$R$_8$, triethylamine, 60-150° C., 6 h to 7 d, or HNR$_7$R$_8$, DIPEA, CH$_3$CN, reflux, or HNR$_7$R$_8$ (neat), NaHCO$_3$, 120° C., 5 h; (i) HNR$_7$R$_8$, 2-Dicyclohexylphosphino-2',6'-diisopropoxybiphenyl, Lithium bis(trimethylsilyl)amide, Dicyclolhexylphosphino-2',6'-diisopropyl-1,1'-biphenyl)(2-(2-aminoethyl)phenyl)palladium (II), nitrogen atmosphere, 60° C.-120° C., 2 h-7 d.

Final products containing chiral centers can be optionally separated by chiral chromatography to obtain individual enantiomers or diastereomers.

Scheme 5: Early Introduction of R$^3$:

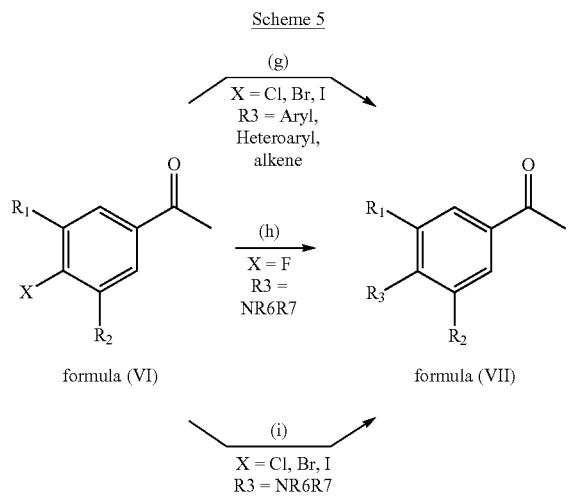

formula (VI) → formula (VII)

Scheme 5: Route for the preparation of compounds of general formula (VII) via formula (VI) in which R$^1$ and R$^2$ have the meaning as defined supra.

(g) R$^x$B(OH)$_2$ or R$^x$-boronic esters, potassium carbonate, 2-(Dicyclohexylphosphino)-2',4',6'-triisopropylbiphenyl, Chloro(2-dicyclohexylphosphino-2',4',6'-triisopropyl-1,1'-biphenyl)[2-(2'-amino-1,1'-biphenyl)]palladium(II), water, nitrogen atmosphere, 80° C.-120° C., 2 h-7 d, or R$^x$B(OH)$_2$ or R$^x$-boronic esters, potassium carbonate, dicyclohexyl[2',4',6'-tri(propan-2-yl)biphenyl-2-yl]phosphane, chloro(2-dicyclohexylphosphino-2',4',6'-triisopropyl-1,1'-biphenyl)[2-(2'-amino-1,1'-biphenyl)]palladium(II), dioxane, 100° C., 16 h; (h) HNR$_7$R$_8$, triethylamine, 60-150° C., 6 h to 7 d, or HNR$_7$R$_8$, DIPEA, CH$_3$CN, reflux, or HNR$_7$R$_8$ (neat), NaHCO$_3$, 120° C., 5 h; (i) HNR$_7$R$_8$, 2-Dicyclohexylphosphino-2',6'-diisopropoxybiphenyl, Lithium bis(trimethylsilyl)amide, Dicyclolhexylphosphino-2',6'-diisopropyl-1,1'-biphenyl)(2-(2-aminoethyl)phenyl)palladium(II), nitrogen atmosphere, 60° C.-120° C., 2 h-7 d. Final products containing chiral centers can be optionally separated by chiral chromatography to obtain individual enantiomers or diastereomers.

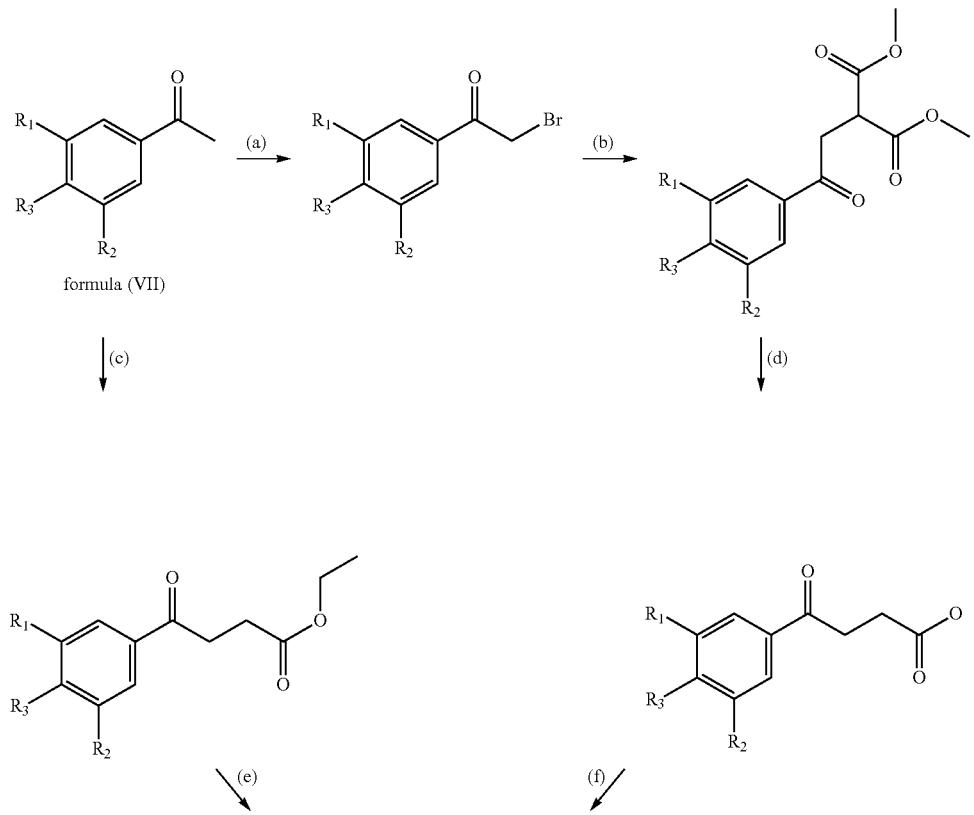

Scheme 6

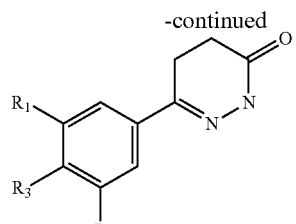

formula (I)

Scheme 6: Route for the preparation of compounds of general formula (I) via formula (VII) in which $R^1$ and $R^2$ have the meaning as defined supra.

(a) acetic acid, bromine, hydrogen bromide, 18 h, RT: (b) dimethyl propanedioate, acetone, potassium carbonate, RT, 18 h; (c) LiHMDS, THF, −78° C., then BrCH$_2$COOEt, −78° C. to RT; (d) conc. aqueous hydrochloric acid, 100° C., 3 d; (e) hydrazine, EtOH, reflux, 6 h, or 1-propanol, hydrazine hydrate (1:1), 100° C., 18 h, or hydrazine hydrate (1:1), 100° C., 18 h; (f) hydrazine, EtOH, reflux, 6 h, or 1-propanol, hydrazine hydrate (1:1), 100° C., 18 h, or hydrazine hydrate (1:1), 100° C., 18 h. Final products containing chiral centers can be optionally separated by any known method such as e.g. chiral chromatography to obtain individual enantiomers or diastereomers.

Scheme 7: Chlorination of Late Stage Intermediates

Scheme 7

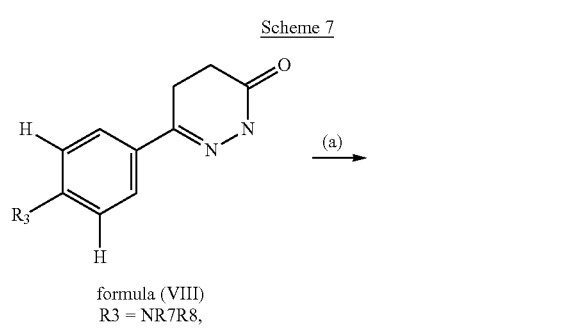

formula (VIII)
R3 = NR7R8, (a)

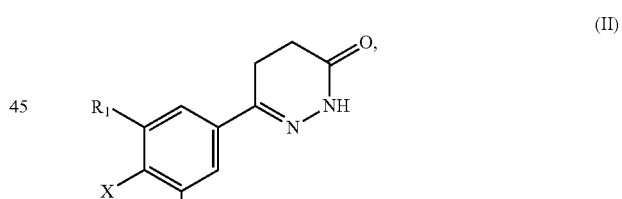

formula (IX)

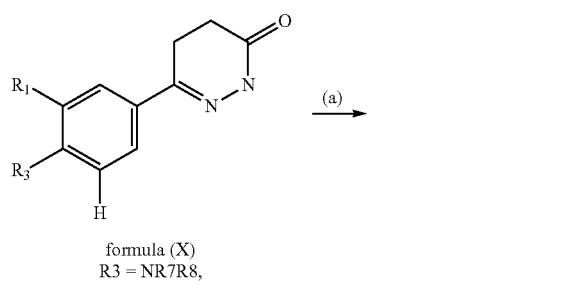

formula (X)
R3 = NR7R8, (a)

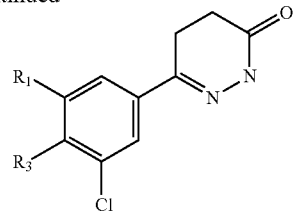

formula (XI)

Scheme 7: Route for the preparation of compounds of general formula (IX) via formula (VIII) and preparation of general formula (XI) via formula (X) in which $R^1$ has the meaning as defined supra.

(a) N-chloro succinimide, THF, RT, 18 h, or, NaOCl/HOAc, 10-15° C., 1-2 h. Final products containing chiral centers can be optionally separated by any known method such as e.g. chiral chromatography to obtain individual enantiomers or diastereomers.

In accordance with a third aspect, the present invention provides a method of preparing a compound of general formula (I) according to any one of claims 1 to 5, said method comprising the step of allowing an intermediate compound of general formula (II):

(II)

in which $R^1$ and $R^2$ have the meaning as defined for the compound of general formula (I) according to claim 1 and X=F, Cl, Br, I
to react a) if X=Cl, Br, I, with the prerequisite that $R^1/R^2$ is not Cl, Br, I, under transmetal catalysed coupling conditions, such as Negishi couplings, Kumada couplings, Stille couplings, particularly Suzuki couplings with of a boronic acid of formula $$(R^x)B(OH)_2 \quad \quad (IIIa)$$

whereby $R^x$ is
a $C_1$-$C_6$-alkoxy group,
a $C_2$-$C_6$-alkenyl group,
a $C_3$-$C_6$-cycloalkyl group, a $C_5$-$C_6$-cycloalkenyl group, a 3- to 7-membered heterocycloalkyl group, which is optionally substituted with one, two, or three substituents and each substituent is independently selected from a halogen atom, a $C_1$-$C_3$-alkyl group, a hydroxy group, $NR^4R^5$ group, a $C_1$-$C_3$-haloalkyl group and a $C_1$-$C_3$-haloalkoxy group, a 5- to 7-membered heterocycloalkyl group which is partially unsaturated and optionally substituted with one, two or three substituents and each substituent is independently selected from an oxo group (=O), a $C_1$-$C_3$-alkyl group and a halogen atom, an aryl group which is optionally substituted with one, two, three or four substituents and each substituent is independently selected from a halogen atom, a hydroxy group, a cyano group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, a —C(O)$NR^4R^5$ group and a $NR^4R^5$ group;

a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^4R^5$ group;

and a $NR^6R^7$ group, or a boronic ester of formula

(IIIb)

wherein $R^x$ is as defined for the boronic acid above and $R^y$ is $C_1$-$C_6$-alkyl, or the two residues $R^y$ together form a pinacol ester,/potassium carbonate/a palladium catalyst selected from the following list: dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene (1,4-naphthoquinone)palladium dimer, allyl(chloro)(1,3-dimesityl-1,3-dihydro-2H-imidazol-2-ylidene) palladium, palladium(III) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), or (2-Dicyclohexylphosphino-2',4',6'-triisopropyl-1,1'-biphenyl)[2-(2'-amino-1,1'-biphenyl)]palladium(II), preference being given to chloro(2-dicyclohexylphosphino-2',4',6'-triisopropyl-1,1'-biphenyl)[2-(2'-amino-1,1'-biphenyl)]palladium(II), in order to obtain a compound of formula (I) wherein $R^3$ is $R^x$.

or b) if X=F, with the prerequisite that $R^1$ is selected from a hydrogen atom, a halogen atom, a cyano group, a $C_1$-$C_3$-haloalkyl group, and $R^2$ is selected from a hydrogen atom and a halogen atom, $R^2$ is F or $CF_3$, ($R^1$ is F or $CF_3$, CN, $R^2$=H, F,) with $HNR^6R^7$ wherein $R^6$ and $R^7$ have the meaning as defined in anyone of claim 1-5, optionally in the presence of a base, and optionally the presence of an inert solvent, and optionally heat, up to the boiling point of the present solvent, especially RT-150° C. in order to obtain a compound of formula (I).

In accordance with a fourth aspect, the present invention provides said intermediate compounds as disclosed above for the preparation of a compound of general formula (I) as defined supra, particularly a compound of formula (II)

In accordance with a fifth aspect, the present invention provides the use of said intermediate compounds for the preparation of a compound of general formula (I) as defined supra.

The present invention provides the intermediate compounds which are disclosed in the Example Section of this text, infra.

The present invention provides any sub-combination within any embodiment or aspect of the present invention of intermediate compounds of general formula (I), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Utility

Compounds of general formula (I) of the present invention demonstrate a valuable pharmacological spectrum of action, which could not have been predicted. Compounds of the present invention have surprisingly been found to effectively modulate a complex formed by SLFN12 and PDE3A and/or PDE3B and it is possible therefore that said compounds be used for the treatment or prophylaxis of diseases, more particularly hyperproliferative diseases, even more particularly cancer diseases in humans and animals.

More particularly the compounds of formula (I) are suitable for the treatment of a patient having a cancer that is sensitive to treatment with a SLFN12-PDE3 complex modulator by detecting co-expression of PDE3A and/or PDE3B and Schlafen 12 (SLFN12) and/or SLFN12L mRNA, polynucleotides or polypeptides and/or a lack of decrease in expression of CREB3L1 mRNA, polynucleotides or polypeptides in a cancer cell derived from such patients.

Compounds of the present invention can be utilized to inhibit, block, reduce, decrease, etc., cell proliferation and/or cell division, and/or produce apoptosis. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disease.

The present compounds of formula (I) may additionally show improved physicochemical properties and/or improved safety pharmacological properties.

Thus a further aspect of the invention are compounds if formula (I) which show improved physicochemical properties compared to compounds of the state of the art.

Another aspect of the invention are those compounds of formula (I) which show an improved safety pharmacological properties.

Further Definitions

By "alteration" is meant a change (increase or decrease) in the expression levels or activity of a gene or polypeptide as detected by standard art known methods such as those described herein. As used herein, in one embodiment an alteration includes an about 10% change in expression levels, preferably an about 25% change, more preferably an about 40% change, and most preferably an about 50% or greater change in expression levels. In certain embodiments an alteration includes a 10% or less (including 10%) change in expression levels, preferably a 25% or less (including 25%) change, more preferably a 40% or less (including 40%) change, and most preferably a 50% or less (including 50%) or greater change in expression levels. In other embodiments an alteration includes a 9%-11% (including 9% and 11%) change in expression levels, preferably a 10%-25% (including 10% and 25%) change, more preferably a 25%-40% (including 25% and 40%) change, and most preferably a 40%-50% (including 40%-50%) or greater than 50% (including 50%) change in expression levels. In other certain embodiments an alteration includes a 9%-11% (including 9% and 11%) change in expression levels, preferably a 22%-28% (including 22% and 28%) change, more preferably a 35%-45% (including 35% and 45%) change, and most preferably a 45%-55% (including 45%-55%) or a greater or equal to 55% change in expression levels By "fragment" is meant a portion of a polypeptide or nucleic acid molecule. This portion contains, preferably, at least about 10%, about 20%, about 30%, about 40%, about 50%, about 60%, about 70%, about 80%, or about 90% of the entire length of the reference nucleic acid molecule or polypeptide. In certain embodiments this portion contains, preferably, at least 9%-11% (including 9% and 11%), 18%-22% (including 18% ands 22%), 27%-33% (including 27% and 33%), 36%-44% (including 36% and 44%), 45%-55% (including 45% and 55%), 54%-66% (including 54% and 66%), 63%-77% (including 63% and 77%), 72%-88% (including 72% and 88%), or 81%-99% (including 81% and 99%) of the entire length of the reference nucleic acid molecule or polypeptide A fragment may contain about 10, about 20, about 30, about 40, about 50, about 60, about 70, about 80, about 90, about 100, about 200, about 300, about 400, about 500, about 600, about 700, about 800, about 900, or about 1000 nucleotides or amino acids. In certain embodiments a fragment may contain 9-11, about 18-22, 27-33, 36-44, 45-55, 54-66, 63-77, 72-88, 81-99, 90-110, 180-220, 270-330, 360-440, 450-550, 540-660, 630-770, 720-880, 810-990, or 900-1100 nucleotides or amino acids (including for each the mentioned limitation e.g. for "9-11" means including 9 and 11.

"Hematopoietic hyperproliferative diseases" also known as myoproliferative diseases include e.g. polycythemia vera, essential thrombocytosis, thrombocytosis, primary myelofibrosis, and others.

"Hyperproliferative diseases" include, but are not limited to, for example: psoriasis, keloids, and other hyperplasias affecting the skin, benign hyperproliferative diseases, hematopoietic hyperproliferative diseases (including polycythemia vera, essential thrombocytosis, primary myelofibrosis), benign prostate hyperplasia (BPH), cancer (especially metastatic or malignant tumors, more specifically solid tumors and haematological tumors).

"Benign hyperproliferative diseases" include for example, endometriosis, leiomyoma and benign prostate hyperplasia.

By "marker" or "biomarker" is meant any protein or polynucleotide having an alteration in expression level or activity (e.g., at the protein or mRNA level) that is associated with a disease or disease. In particular embodiments, a marker of the invention is PDE3A or PBE3B or SLFN12 or CREB3L1.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide. In some embodiments, the modulator which modulates a complex formed by SLFN12 and PDE3A/PDE3B polypeptide is a compound of formula (I).

"Solid tumours" are such as cancers of the breast, brain, digestive tract, eye, head and neck, liver, parathyroid, reproductive organs, respiratory tract, skin, thyroid, urinary tract, and their distant metastases. Those diseases also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of "brain cancers" include, but are not limited to, brain stem and hypophtalmic glioma, cerebellar and cerebral astrocytoma, medulloblastoma, ependymoma, as well as neuroectodermal and pineal tumour.

Tumours of the "digestive tract" include, but are not limited to, anal, colon, colorectal, oesophageal, gallbladder, gastric, pancreatic, rectal, small-intestine, and salivary gland cancers.

"Eye cancers" include, but are not limited to, intraocular melanoma and retinoblastoma.

"Head-and-neck cancers" include, but are not limited to, laryngeal, hypopharyngeal, nasopharyngeal, oropharyngeal cancer, lip and oral cavity cancer and squamous cell.

Examples of "liver cancers" include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Examples of cancers of the "respiratory tract" include, but are not limited to, small-cell and non-small-cell lung carcinoma, as well as bronchial adenoma and pleuropulmonary blastoma.

"Reproductive organs" include female- and male reproductive organs.

"Tumours of the female reproductive organs" include, but are not limited to, endometrial, cervical, ovarian, vaginal, and vulvar cancer, as well as sarcoma of the uterus. T"umours of the male reproductive organs" include, but are not limited to, prostate and testicular cancer.

"Skin cancers" include, but are not limited to, squamous cell carcinoma, Kaposi's sarcoma, malignant melanoma, Merkel cell skin cancer, and non-melanoma skin cancer.

"Tumours of the urinary tract" include, but are not limited to, bladder, penile, kidney, renal pelvis, ureter, urethral and human papillary renal cancers.

"Lymphomas" include, but are not limited to, AIDS-related lymphoma, non-Hodgkin's lymphoma, cutaneous T-cell lymphoma, Burkitt lymphoma, Hodgkin's disease, and lymphoma of the central nervous system.

"Sarcomas" include, but are not limited to, sarcoma of the soft tissue, osteosarcoma, malignant fibrous histiocytoma, lymphosarcoma, and rhabdomyosarcoma.

"Leukemias" include, but are not limited to, acute myeloid leukemia, acute lymphoblastic leukemia, chronic lymphocytic leukemia, chronic myelogenous leukemia, and hairy cell leukemia.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a disease and/or symptoms associated therewith. It will be appreciated that, although not precluded, treating a disease or condition does not require that the disease, condition or symptoms associated therewith be completely eliminated.

Any compositions or methods provided herein can be combined with one or more of any of the other compositions and methods provided herein.

The term "treating" or "treatment" as stated throughout this document is used conventionally, for example the management or care of a subject for the purpose of combating, alleviating, reducing, relieving, improving the condition of a disease or disease, such as a carcinoma. These diseases have been well characterized in humans, but also exist with a similar etiology in other mammals, and can be treated by administering pharmaceutical compositions of the present invention.

The compounds of the present invention can be used in particular in therapy and prevention, i.e. prophylaxis, of hyperproliferative diseases, more particularly of cancer diseases, e.g. heamatological cancer diseases and tumour growth and metastasis, especially in solid tumours and heamatological cancer diseases of all indications and stages with or without pre-treatment of the tumour.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In another aspect, the cell is in vitro. In another embodiment, the cell is in vivo.

Optionally, an anti-neoplasia therapeutic (e.g., compounds of general formula (I)) may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy for the treatment of a neoplasia (e.g., melanoma, lung adenocarcinoma or a cervical cancer).

The present invention also provides compounds of formula (I) for methods of treating hyperproliferative diseases, more particularly cancer diseases including hematological cancer diseases and solid tumors.

In one embodiment the invention provides methods of treatment mentioned above where tumors are selected from list given above, more particularly the tumors are: tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor.

These diseases have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as cancer.

The compounds of the present invention can be used in particular in therapy and prevention, i.e. prophylaxis, of hyperproliferative diseases, more particularly cancer diseases.

In accordance with a further aspect, the present invention provides compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative diseases.

The pharmaceutical activity of the compounds according to the invention can be explained by their activity by effectively modulating a complex formed by SLFN12 and PDE3A and/or PDE3B.

Thus a further aspect of the invention is a method of treatment comprising administering a compound of formula (I) or a pharmaceutical composition thereof to a patient suffering from a cancer disease being sensitive to a treatment with a PDE3A- and/or PDE3B-SLFN12 complex modulator.

Another aspect of the invention is a method of treatment comprising the steps of
  deriving cancer cells from a patient,
  detecting co-expression of PDE3A and/or
  detecting co-expression of PDE3B
  and detecting co-expression of Schlafen 12 (SLFN12) and/or SLFN12L mRNA, polynucleotides or polypeptides
  and/or a lack of decrease in expression of CREB3L1 mRNA, polynucleotides or polypeptides in said cancer cells,
  summarizing the overall results whether the data collected indicate that said cancer cells are sensitive to the treatment with a compound of formula (I),
  and administering a compound of formula (I) to said patient.

Another aspect of the invention is a method of treatment comprising the steps of
deriving cancer cells from a patient,
detecting co-expression of PDE3A and/or
detecting co-expression of PDE3B
and detecting co-expression of Schlafen 12 (SLFN12) and/or SLFN12L mRNA, polynucleotides or polypeptides
and/or a lack of decrease in expression of CREB3L1 mRNA, polynucleotides or polypeptides in said cancer cells,
summarizing the overall results
depending whether the data collected indicate that said cancer cells are sensitive to the treatment with a compound of formula (I) deciding on a treatment of said patient with a compound of formula (I), Another aspect of the invention is a method of treatment comprising the steps of
deriving cancer cells from a patient,
detecting co-expression of PDE3A and/or
detecting co-expression of PDE3B
and detecting co-expression of Schlafen 12 (SLFN12) and/or SLFN12L mRNA, polynucleotides or polypeptides
and/or a lack of decrease in expression of CREB3L1 mRNA, polynucleotides or polypeptides in said cancer cells,
summarizing the overall results
depending whether the data collected indicate that said cancer cells are sensitive to the treatment with a compound of formula (I) deciding on a treatment of said patient with a compound of formula (I),
and treating said patient with a compound of formula (I).

In accordance with a further aspect, the present invention provides the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular hyperproliferative diseases, particularly cancer diseases.

In accordance with a further aspect, the present invention provides the a compound of formula (I), described supra, or a stereoisomer, a tautomer, an N-oxide, a hydrate, a solvate, or a salt thereof, particularly a pharmaceutically acceptable salt thereof, or a mixture of same, for use in the prophylaxis or treatment of diseases, in particular hyperproliferative diseases, particularly cancer diseases.

In accordance with a further aspect, the present invention provides the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular hyperproliferative diseases, particularly cancer diseases.

In accordance with a further aspect, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative diseases, particularly cancer diseases.

In accordance with a further aspect, the present invention provides a method of treatment or prophylaxis of diseases, in particular hyperproliferative diseases, particularly cancer diseases, comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a patient in need thereof.

Pharmaceutical Composition

In accordance with a further aspect, the present invention provides pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore provides pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides, fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Combinations

In accordance with another aspect, the present invention provides pharmaceutical combinations, in particular medicaments, comprising at least one compound of general formula (I) of the present invention and at least one or more further active ingredients, in particular for the treatment and/or prophylaxis of a hyperproliferative disease, a cancer disease.

Particularly, the present invention provides a pharmaceutical combination, which comprises:
one or more first active ingredients, in particular compounds of general formula (I) as defined supra, and
one or more further active ingredients, in particular a hyperproliferative disease, a cancer disease.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also provides such pharmaceutical combinations. For example, the compounds of the present invention can be combined with known anti-cancer agents.

Examples of anti-cancer-agents include:
131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, more particularly cancer diseases by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 500 mg/kg body weight per day, particularly about 0.001 mg/kg to about 200 mg/kg body weight per day, and more particularly from about 0.01 mg/kg to about 50 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. For oral administration the dosing schedule may be once or two time or three times daily and a dose range as referred to above for general dosing is possible.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered.

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$) . . . $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

| Abbreviations | |
|---|---|
| [α] | specific rotation value |
| EtOH | Ethanol |
| THF | Tetrahydrofurane |
| DAD | Diode array detector |
| δ | NMR shift in ppm |
| d | doublet (NMR coupling pattern) |
| DMSO | dimethylsulfoxide |
| M | Molar or molecular Mass |
| ESI | electrospray ionisation (MS) |
| LiHMDS | Lithium 1,1,1,3,3,3-hexamethyldisilazan-2-ide |
| LC-MS | liquid chromatography coupled to mass spectrometry |
| m | multiplet (NMR coupling pattern) |
| MS | mass spectrometry |
| MHz | Megahertz |
| NMR | nuclear magnetic resonance |
| q | quartet (NMR coupling pattern) |
| Rt | retention time |
| RT | room temperature |
| s | singlet (NMR coupling pattern) |
| t | triplet (NMR coupling pattern) |
| UPLC | Ultra Performance Liquid Chromatography |
| UV | ultraviolet |
| WL | wavelength |
| DIPEA | N,N-diisopropylethylamine |
| UPLC-MS | Ultra High Preformance Liquid Chromatography Mass Spectroscopy |
| pH | Potential of Hydrogen |
| MTBE | Metyl tButyl ether |
| EtOAc | Ethyl acetate |
| Et | Ethyl |
| Me | Methyl |
| Pr | Propyl |
| AMC | Automated Medicinal Chemistry |
| DMF | dimethylformamide |
| MeOH | methanol |
| HOAc | Acetic Acid |
| DMF | Dimethylformamide |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Experimental Section—General Procedures

Analytical LC-MS Methods:
Method 1:
Instrument: Waters Acquity UPLC-MS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.;
DAD scan: 210-400 nm.
Method 2:
Instrument: Waters Acquity UPLC-MSUPLC-MS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.
Method 3:
Instrument: SHIMADZU LCMS-UFLC 20-AD-LCMS 2020 MS detector; Column: Waters Atlantis dC18 3 μm, 2.1×100 mm; eluent A: water+0.1% formic acid (v/v), eluent B: acetonitrile+0.1% formic acid (v/v); gradient: 0-5.00 min 5-100% B 5.00-5.40 min 100% B; flow: 0.6 mL/min; temperature: 40° C.; PD A scan: 210-420 nm.

Method 4:
Instrument Waters Acquity UPLCMS SingleQuad; Column: Phenomenex Kinetix-XB C18 1.7 μm, 2.1×100 mm; eluent A: water+0.1% formic acid (v/v), eluent B: acetonitrile+0.1% formic acid (v/v); gradient: 0-5.30 min 5-100% B, 5.30-5.80 min 100% B; flow: 0.6 mL/min; temperature: 40° C.; PDA scan: 200-400 n m.

Method 5:
Instrument: Waters Acquity UPLC-MS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm Preparative HPLC Methods:
Instrument Description:
Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; Eluent acidic: solvent A: water+0.1 vol-% formic acid, solvent B: acetonitrile Gradients:
Gradient_B_150 mL_30-09-2014: gradient: 0.00-0.50 min 10% B (150 mL/min), 0.50-6.00 min 10-50% B (150 mL/min), 6.00-6.10 min 50-100% B (150 mL/min), 6.10-8.00 min 100% B (150 mL/min)

Gradient_D_150 mL_30-09-2014:gradient: 0.00-0.50 min 30% B (150 mL/min), 0.50-6.00 min 30-70% B (150 mL/min), 6.00-6.10 min 70-100% B (150 mL/min), 6.10-8.00 min 100% B (150 mL/min); UV-Detection Method 6:
Instrument: Waters Autopurificationsystem; Colum: Waters XBrigde C18 5μ 100×30 mm; eluent A: water+0.2 Vol-% aqueous ammonia (32%), Eluent B: acetonitrile; gradient: 0.00-0.50 min 25% B (25->70 mL/min), 0.51-5.50 min 25-50% B (70 mL/min), DAD scan: 210-400 nm Experimental Section—General Procedures General Details All reactions were carried out under nitrogen ($N_2$) atmosphere. All reagents and solvents were purchased from commercial vendors and used as received. Nuclear magnetic resonance (NMR) spectra were recorded on a Bruker (300 or 400 MHz $^1$H, 75 or 101 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Flash chromatography was performed using 40-60 μm Silica Gel (60 Å mesh) on a Teledyne Isco Combiflash Rf. Tandem Liquid Chromatography/Mass Spectrometry (LC/MS) was performed on a Waters 2795 separations module and 3100 mass detector with a Waters Symmetry C18 column (3.5 μm, 4.6×100 mm) with a gradient of 0-100% CH3CN in water over 2.5 min with constant 0.1% formic acid. Analytical thin layer chromatography (TLC) was performed on EM Reagent 0.25 mm silica gel 60-F plates.

Experimental Section—Intermediates

Intermediate 1

Methyl 4-(4-fluorophenyl)-4-oxobutanoate

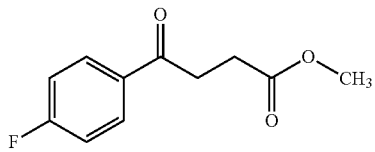

To 4.0 g of 4-(4-fluorophenyl)-4-oxobutanoic acid (20 mmol, CAS 366-77-8) in 150 mL of MeOH was added 2 mL of $H_2SO_4$ and the reaction mixture was heated at reflux temperature overnight. After cooling, the reaction mixture was neutralized with solid $NaHCO_3$, filtered and concentrated. The residue was partitioned between $CH_2Cl_2$ and water, the $CH_2Cl_2$ was dried and concentrated to 3.63 g of white solid (85%).

$^1$H NMR (400 MHz, $CDCl_3$) δ 8.09-7.94 (m, 2H), 7.14 (t, J=8.6 Hz, 2H), 3.71 (s, 3H), 3.29 (t, J=6.6 Hz, 2H), 2.77 (t, J=6.6 Hz, 2H). $^{19}$F NMR (376 MHz, $CDCl_3$) δ−105.09.

Intermediate 2

Methyl 4-(4-morpholinophenyl)-4-oxobutanoate

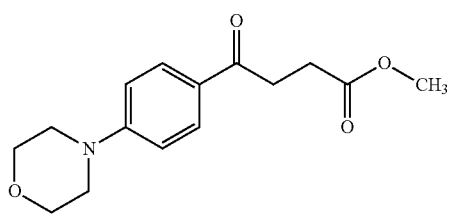 [SMILES: COC(=O)CCC(=O)c1ccc(N2CCOCC2)cc1]

To 10 mL of morpholine was added 1.33 g of methyl 4-(4-fluorophenyl)-4-oxobutanoate (6.33 mmol, Intermediate 1) and some solid $NaHCO_3$ and the mixture was heated at 120° C. for 5 h. The reaction mixture was concentrated, water was added twice and was rinsed twice with $CH_2Cl_2$. The combined $CH_2Cl_2$ layers were dried and concentrated. Chromatography with 20-60% EtOAc in hexane yielded 558 mg product as a white solid (32%).

$^1$H NMR (400 MHz, $CDCl_3$) δ 7.92 (d, J=9.0 Hz, 2H), 6.87 (d, J=9.0 Hz, 2H), 3.91-3.80 (m, 4H), 3.70 (s, 3H), 3.35-3.28 (m, 4H), 3.25 (t, J=6.8 Hz, 2H), 2.74 (t, J=6.8 Hz, 2H). $^{13}$C NMR (101 MHz, $CDCl_3$) δ 196.18, 173.61, 154.31, 130.04, 127.41, 113.30, 66.56, 51.76, 47.52, 32.81, 28.22. Mass 278 (M+1)+.

Intermediate 3

Ethyl 4-(3,4-dichlorophenyl)-4-oxobutanoate

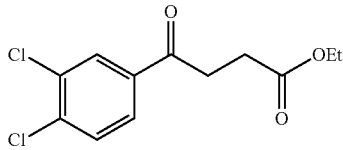 [SMILES: CCOC(=O)CCC(=O)c1ccc(Cl)c(Cl)c1]

To 30 mL of THF was added 26 mL (26 mmol) of a 1 N (THF) solution of LHMDS and the solution was cooled to −78° C. A solution of 5.0 g of 1-(3,4-dichlorophenyl)ethan-1-one (26 mmol, CAS 2642-63-9) in 15 mL of THF was added and stirred cold for 1 h after which a solution of 4.42 g of ethyl bromoacetate (26 mmol) in 10 mL THF was added. The reaction was warmed to room temperature. After several hours, the solution was cooled and quenched with 1 N HCl. EtOAc was added, the water was separated and rinsed with EtOAc, the combined organic layers were dried and concentrated. Chromatography with 0-10% EtOAc in hexane isolated 218 mg of product as an oil (3%).

Mass 275 (M+1)+.

Intermediate 4

Dimethyl [2-(4-chloro-3-methylphenyl)-2-oxoethyl]propanedioate

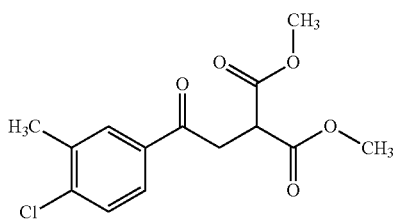 [SMILES: COC(=O)C(CC(=O)c1ccc(Cl)c(C)c1)C(=O)OC]

2-Bromo-1-(4-chloro-3-methylphenyl)ethanone (3.00 g, 12.1 mmol, CAS 205178-80-9) was dissolved in acetone (12 mL, 160 mmol), potassium carbonate (2.51 g, 18.2 mmol) and dimethyl propanedioate (1.7 mL, 15 mmol) were added. The mixture was stirred at RT for 18 h. Precipitates were filtered off and solvents were removed in vacuo to obtain the raw title product.

LC-MS (Method 1): $R_t$=1.23 min; MS (ESIpos): m/z=299 [M+H]+

Intermediate 5

4-(4-Chloro-3-methylphenyl)-4-oxobutanoic acid

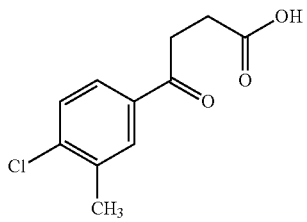

Dimethyl [2-(4-chloro-3-methylphenyl)-2-oxoethyl]propanedioate (3.62 g, 12.1 mmol, Intermediate 4) was treated with conc. aqueous hydrochloric acid (10 mL, 37% purity, 120 mmol) and stirred at 100° C. for 3 d. More conc. aqueous hydrochloric acid (5 mL) was added and the mixture was stirred at 100° C. for another 3 d. Toluene was added and solvets were removed in vacuo to obtain the raw title product (2.75 g).

LC-MS (Method 1): $R_t$=1.04 min; MS (ESIpos): m/z=227 [M+H]+

Intermediate 6

6-(4-Chloro-3-methylphenyl)-4,5-dihydropyridazin-3(2H)-one

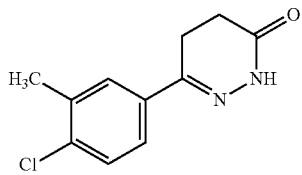

4-(4-chloro-3-methylphenyl)-4-oxobutanoic acid (2.75 g, 12.1 mmol, Intermediate 5) was suspended in 1-propanol (15 mL) and hydrazine hydrate (1:1) (3.0 mL, 100% purity, 61 mmol) was added. The mixture was stirred at 100° C. for 1 h. Precipitates were filtered off and solvents were removed in vacuo to obtain the raw title product. After cooling to RT, water was slowly added and the mixture was stirred for 1 h at RT. The resulting precipitate was filtered, washed with water and dried in vacuo twice. The combined precipitates were purified via chromatography (Method 6) to obtain the desired product (1.60 g, 95% purity, 56% yield).

LC-MS (Method 1): $R_t$=1.04 min; MS (ESIpos): m/z=223 [M+H]$^+$ $^1$H-NMR (400 MHz, DMSO-d6) δ[ppm]: 2.084 (0.21), 2.327 (0.25), 2.332 (0.22), 2.363 (16.00), 2.420 (2.73), 2.441 (5.00), 2.461 (3.32), 2.522 (0.67), 2.585 (0.18), 2.669 (0.21), 2.805 (0.16), 2.911 (3.25), 2.933 (5.03), 2.953 (2.65), 7.442 (2.81), 7.463 (3.84), 7.569 (1.77), 7.574 (1.88), 7.590 (1.25), 7.595 (1.35), 7.722 (2.85), 7.726 (2.67), 10.110 (0.19), 10.962 (3.29).

Intermediate 7

Dimethyl [2-(4-chloro-3-fluorophenyl)-2-oxoethyl]propanedioate

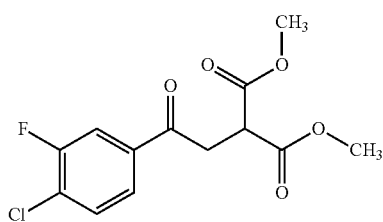 [SMILES: COC(=O)C(CC(=O)c1ccc(Cl)c(F)c1)C(=O)OC]

2-Bromo-1-(4-chloro-3-fluorophenyl)ethanone (900 mg, 3.58 mmol, CAS 231297-62-4) was dissolved in acetone (16 mL, 210 mmol), potassium carbonate (742 mg, 5.37 mmol) and dimethyl propanedioate (3.3 mL, 29 mmol) were added. The mixture was stirred at RT for 18 h. Precipitates were filtered off, washed with acetone, and solvents were removed in vacuo to obtain the raw title product (4.2 g).

LC-MS (Method 1): $R_t$=1.21 min; MS (ESIpos): m/z=303 [M+H]$^+$

Intermediate 8

4-(4-Chloro-3-fluorophenyl)-4-oxobutanoic acid

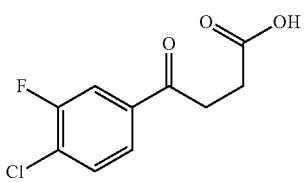 [SMILES: O=C(O)CCC(=O)c1ccc(Cl)c(F)c1]

Dimethyl [2-(4-chloro-3-fluorophenyl)-2-oxoethyl]propanedioate (1.08 g, 3.58 mmol, Intermediate 7) was treated with conc. aqueous hydrochloric acid (15 mL, 37% purity, 180 mmol) and stirred at 100° C. for 3 d. More conc. aqueous hydrochloric acid (5 mL) was added and the mixture was stirred at 100° C. for another 3 d. Toluene was added three times and solvets were removed in vacuo to obtain the raw title product (2 g).

LC-MS (Method 1): Rt=0.95 min; MS (ESIpos): m/z=131 [M+H]$^+$

Intermediate 9

6-(4-Chloro-3-fluorophenyl)-4,5-dihydropyridazin-3(2H)-one

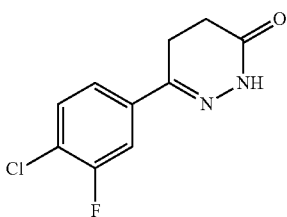 [SMILES: O=C1CCC(c2ccc(Cl)c(F)c2)=NN1]

4-(4-Chloro-3-fluorophenyl)-4-oxobutanoic acid (6.51 g, 28.2 mmol, Intermediate 8) was dissolved in 1-propanol and hydrazine hydrate (1:1) (17 mL, 80% purity, 280 mmol) was added. The mixture was stirred at 100° C. for 18 h. Precipitates were filtered off and solvents were removed in vacuo to obtain the raw title product. After cooling to RT, water was slowly added and the mixture was stirred for 1 h at RT. The resulting precipitate was filtered, washed with water and dried in vacuo twice. The combined precipitates were treated with MTBE and the resulting precipitate was filtered, washed with MTBE and dried in vacuo. The desired product (4.70 g, 90% purity, 66% yield) was obtained.

LC-MS (Method 1): Rt=0.98 min; MS (ESIpos): m/z=227 [M+H]$^+$ $^1$H-NMR (400 MHz, DMSO-d6) δ[ppm]: 1.102 (3.85), 1.739 (0.62), 1.898 (0.52), 2.237 (0.98), 2.322 (0.52), 2.327 (0.76), 2.332 (0.52), 2.437 (5.93), 2.457 (11.16), 2.478 (8.53), 2.518 (2.71), 2.523 (1.99), 2.599 (0.70), 2.618 (0.45), 2.665 (0.58), 2.669 (0.83), 2.673 (1.80), 2.795 (0.45), 2.815 (0.65), 2.895 (16.00), 2.926 (7.64), 2.947 (11.39), 2.967

(5.94), 3.031 (0.65), 3.072 (1.57), 3.154 (0.61), 3.164 (0.76), 3.249 (1.71), 3.263 (1.28), 3.351 (2.20), 3.468 (1.16), 3.541 (0.85), 3.577 (0.50), 3.606 (1.71), 3.639 (0.47), 5.886 (0.50), 7.586 (0.63), 7.592 (2.70), 7.597 (2.86), 7.613 (6.80), 7.618 (8.72), 7.629 (6.19), 7.639 (0.52), 7.648 (6.14), 7.668 (2.83), 7.694 (0.40), 7.700 (0.50), 7.708 (3.98), 7.712 (3.74), 7.735 (4.42), 7.740 (4.09), 9.064 (1.18), 11.059 (5.67).

Intermediate 10

5-Acetyl-2-(morpholin-4-yl)benzonitrile

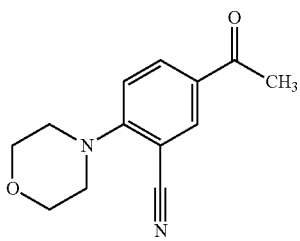 [SMILES: CC(=O)c1ccc(N2CCOCC2)c(C#N)c1]

5-Acetyl-2-fluorobenzonitrile (2.00 g, 12.3 mmol, CAS 288309-07-9) was dissolved in N,N-diisopropylethylamine (6.4 mL, 37 mmol) and morpholine (5.3 mL, 61 mmol) was added. The mixture was heated at 100° C. overnight. The mixture was concentrated in vacuo and then water was added. The aqueous phase was extracted with ethyl acetate three times. Solvents were removed in vacuo to give 3.00 g (quant. yield) of the title compound.

LC-MS (Method 1): $R_t$=0.90 min; MS (ESIpos): m/z=231 [M+H]$^+$

Intermediate 11

5-(Bromoacetyl)-2-(morpholin-4-yl)benzonitrile

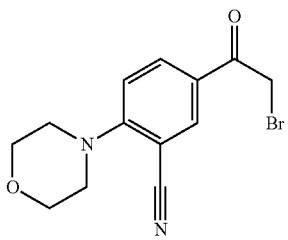 [SMILES: N#Cc1cc(C(=O)CBr)ccc1N1CCOCC1]

5-Acetyl-2-(morpholin-4-yl)benzonitrile (1.18 g, 5.12 mmol, Intermediate 10) was dissolved in acetic acid (12 mL, 210 mmol), then bromine (260 µL, 5.1 mmol) and aqueous hydrobromic acid (29 µL, 48% purity, 260 µmol) were added. The mixture was stirred at RT for 2 d and at 40° C. for 18 h. More aqueous hydrobromic acid (29 µL, 48% purity, 260 µmol) and bromine (2.5 mmol) were added and the mixture stirred at 30° C. for 4 h. After cooling to room temperature under stirring the reaction mixture was poured into water and adjusted to a pH of 5 with sodium hydrogen carbonate. The mixture was stirred for 3 d and the resulting precipitate was filtered, washed with water, and dried in vacuo to obtain 1.40 g (88% yield) of the title compound.

LC-MS (Method 1): $R_t$=1.03 min; MS (ESIpos): m/z=309 [M+H]$^+$

Intermediate 12

Dimethyl {2-[3-cyano-4-(morpholin-4-yl)phenyl]-2-oxoethyl}propanedioate

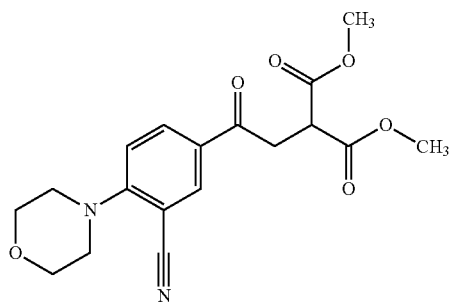 [SMILES: COC(=O)C(CC(=O)c1ccc(N2CCOCC2)c(C#N)c1)C(=O)OC]

5-(Bromoacetyl)-2-(morpholin-4-yl)benzonitrile (486 mg, 1.57 mmol, Intermediate 11) was dissolved in acetone (8.0 mL), potassium carbonate (326 mg, 2.36 mmol) and dimethyl propanedioate (270 µL, 2.4 mmol) were added. The mixture was stirred at RT for 18 h. Precipitates were filtered off, washed with acetone, and solvents were removed in vacuo to obtain the raw title product (600 mg, quant.).

LC-MS (Method 1): $R_t$=1.03 min; MS (ESIpos): m/z=361 [M+H]$^+$

Intermediate 13

4-[3-Cyano-4-(morpholin-4-yl)phenyl]-4-oxobutanoic acid

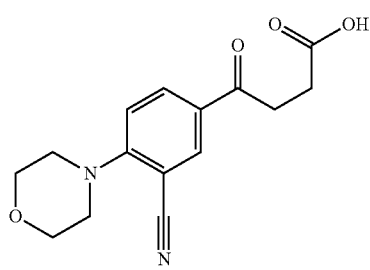 [SMILES: N#Cc1cc(C(=O)CCC(=O)O)ccc1N1CCOCC1]

Dimethyl {2-[3-cyano-4-(morpholin-4-yl)phenyl]-2-oxoethyl}propanedioate (600 mg, 1.66 mmol, Intermediate 12) was treated with conc. aqueous hydrochloric acid (3.4 mL, 37% purity, 42 mmol) and stirred at 100° C. for 3 d. More conc. aqueous hydrochloric acid (5 mL) was added and the mixture was stirred at 100° C. for another 3 d. Toluene was added three times and solvents were removed in vacuo to obtain the raw title product (500 mg, quant.)

LC-MS (Method 1): $R_t$=0.81 min; MS (ESIpos): m/z=289 [M+H]$^+$

Intermediate 14

Dimethyl [2-oxo-2-(3,4,5-trifluorophenyl)ethyl]propanedioate

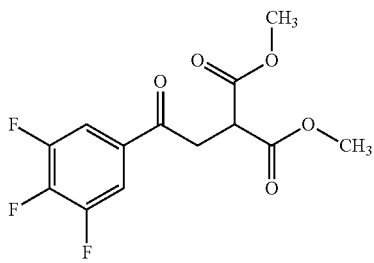 [SMILES: COC(=O)C(CC(=O)c1cc(F)c(F)c(F)c1)C(=O)OC]

2-Bromo-1-(3,4,5-trifluorophenyl)ethanone (500 mg, 1.98 mmol, CAS 443914-94-1) was dissolved in acetone (12 mL), potassium carbonate (410 mg, 2.96 mmol) and dimethyl propanedioate (1.8 mL, 16 mmol) were added. The mixture was stirred at RT for 18 h. Precipitates were filtered off, washed with acetone, and solvents were removed in vacuo to obtain the raw title product.

LC-MS (Method 1): $R_t$=1.18 min; MS (ESIpos): m/z=304 [M+H]$^+$

Intermediate 15

4-Oxo-4-(3,4,5-trifluorophenyl)butanoic acid

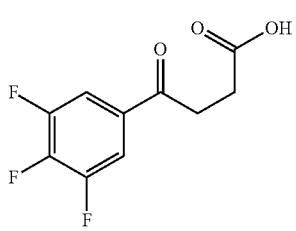 [SMILES: O=C(O)CCC(=O)c1cc(F)c(F)c(F)c1]

Dimethyl [2-oxo-2-(3,4,5-trifluorophenyl)ethyl]propanedioate (440 mg, 1.45 mmol, Intermediate 14) was treated with conc. aqueous hydrochloric acid (6.0 mL, 37% purity, 72 mmol) and stirred at 100° C. for 18 h. Toluene was added three times and solvets were removed in vacuo to obtain the raw title product (870 mg).

LC-MS (Method 1): $R_t$=0.95 min; MS (ESIneg): m/z=231 [M+H]$^+$

Intermediate 16

2-Bromo-1-[4-fluoro-3-(trifluoromethyl)phenyl]ethanone

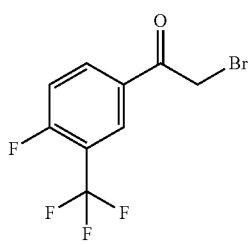 [SMILES: O=C(CBr)c1ccc(F)c(C(F)(F)F)c1]

1-[4-Fluoro-3-(trifluoromethyl)phenyl]ethanone (7.7 mL, 100% purity, 49 mmol, CAS 208173-24-4) was dissolved in acetic acid (70 mL), then a solution of bromine (2.5 mL, 100% purity, 49 mmol) in acetic acid (5 mL) was added slowly. The mixture was stirred at RT for 18 h. The mixture was dried in vacuo to obtain 3.50 g of the title compound.

Intermediate 17

Dimethyl {2-[4-fluoro-3-(trifluoromethyl)phenyl]-2-oxoethyl}propanedioate

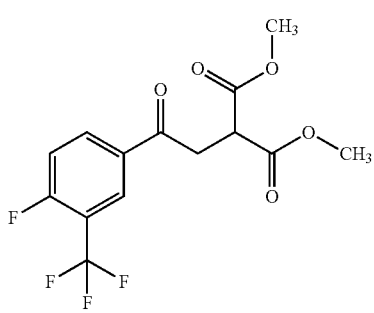 [SMILES: COC(=O)C(CC(=O)c1ccc(F)c(C(F)(F)F)c1)C(=O)OC]

2-Bromo-1-[4-fluoro-3-(trifluoromethyl)phenyl]ethanone (6.91 g, 24.3 mmol, Intermediate 16) was dissolved in acetone (120 mL), potassium carbonate (5.03 g, 36.4 mmol) and dimethyl propanedioate (5.5 mL, 49 mmol) were added. The mixture was added. The mixture was stirred at RT for 18 h. Precipitates were filtered off, washed with acetone, and solvents were removed in vacuo to obtain the raw title product.

LC-MS (Method 1): $R_t$=1.23 min; MS (ESIpos): m/z=337 [M+H]$^+$

Intermediate 18

4-[4-Fluoro-3-(trifluoromethyl)phenyl]-4-oxobutanoic acid

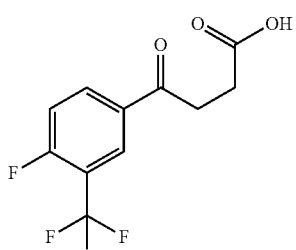

Dimethyl {2-[4-fluoro-3-(trifluoromethyl)phenyl]-2-oxoethyl}propanedioate (8.16 g, 24.3 mmol, Intermediate 17) was treated with conc. aqueous hydrochloric acid (60 mL, 37% purity, 730 mmol) and stirred at 100° C. for 18 h. Toluene was added three times and solvets were removed in vacuo to obtain the raw title product (6.2 g).

LC-MS (Method 1): $R_t$=1.03 min; MS (ESIneg): m/z=263 [M−H]$^+$

Intermediate 19

4-[4-(4,4-Difluoropiperidin-1-yl)-3,5-difluorophenyl]-4-oxobutanoic acid

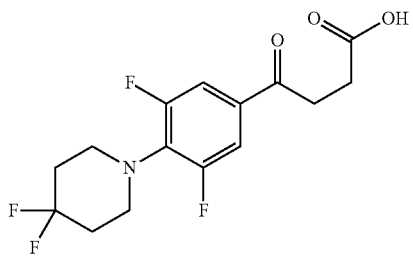 [SMILES: O=C(O)CCC(=O)c1cc(F)c(N2CCC(F)(F)CC2)c(F)c1]

4-Oxo-4-(3,4,5-trifluorophenyl)butanoic acid (200 mg, 861 µmol, Intermediate 15) was dissolved in N,N-diisopropylethylamine (1.5 mL, 8.6 mmol) and 4,4-difluoropiperidine hydrochloride (1:1) (407 mg, 2.58 mmol) was added. The mixture was stirred at 100° C. for 1-3 d. Solvents were removed to obtain the raw product that was used for the next step without purification.

LC-MS (Method 1): $R_t$=1.16 min; MS (ESIneg): m/z=332 [M−H]$^+$

Intermediate 20

4-[4-(3,3-difluoropyrrolidin-1-yl)-3,5-difluorophenyl]-4-oxobutanoic acid

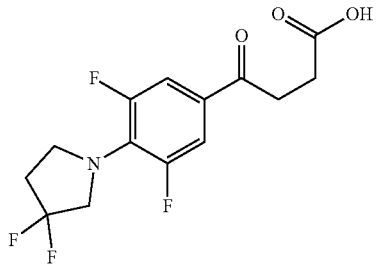 [SMILES: O=C(O)CCC(=O)c1cc(F)c(N2CCC(F)(F)C2)c(F)c1]

Prepared in analogy to Intermediate 19 from Intermediate 15.

LC-MS (Method 1): $R_t$=1.16 min; MS (ESIneg): m/z=332 [M−H]$^+$

Intermediate 21

4-[4-(3-azabicyclo[3.1.0]hex-3-yl)-3,5-difluorophenyl]-4-oxobutanoic acid

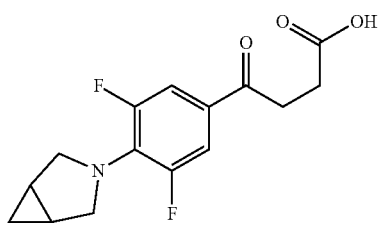 [SMILES: O=C(O)CCC(=O)c1cc(F)c(N2CC3CC3C2)c(F)c1]

Prepared in analogy to Intermediate 19 from Intermediate 15.

LC-MS (Method 1): $R_t$=1.22 min; MS (ESIneg): m/z=294 [M−H]$^+$

Intermediate 23

4-[3,5-difluoro-4-(piperidin-1-yl)phenyl]-4-oxobutanoic acid

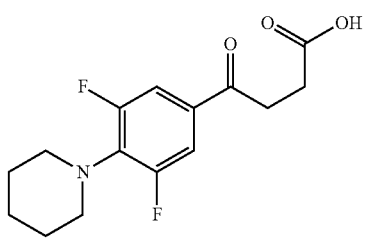 [SMILES: O=C(O)CCC(=O)c1cc(F)c(N2CCCCC2)c(F)c1]

Prepared in analogy to Intermediate 19 from Intermediate 15.

LC-MS (Method 1): Rt=1.27 min; MS (ESIneg): m/z=296 [M−H]$^+$

Intermediate 24

4-{3,5-difluoro-4-[2-methyl-3-azabicyclo[3.1.0]hex-3-yl]phenyl}-4-oxobutanoic acid

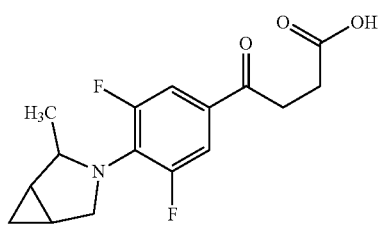 [SMILES: CC1C2CC2CN1c1c(F)cc(C(=O)CCC(=O)O)cc1F]

Prepared in analogy to Intermediate 19 from Intermediate 15.

LC-MS (Method 1): Rt=1.30 min; MS (ESIneg): m/z=308 [M−H]$^+$

Intermediate 25

4-[4-(3,3-difluoroazetidin-1-yl)-3-(trifluoromethyl)phenyl]-4-oxobutanoic acid

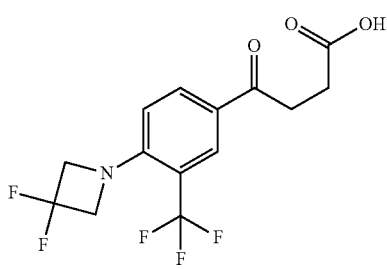 [SMILES: O=C(O)CCC(=O)c1ccc(N2CC(F)(F)C2)c(C(F)(F)F)c1]

Prepared in analogy to Intermediate 19 from Intermediate 18.
LC-MS (Method 1): $R_t$=1.12 min; MS (ESIneg): m/z=336 [M−H]⁺

Intermediate 26

4-{4-[2-methylpyrrolidin-1-yl]-3-(trifluoromethyl)phenyl}-4-oxobutanoic acid

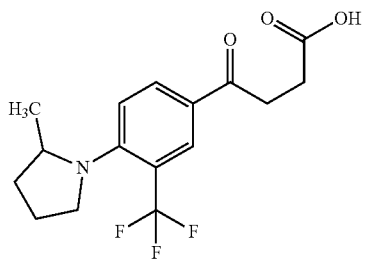 [SMILES: CC1CCCN1c1ccc(C(=O)CCC(=O)O)cc1C(F)(F)F]

Prepared in analogy to Intermediate 19 from Intermediate 18.
LC-MS (Method 1): $R_t$=1.27 min; MS (ESIneg): m/z=329 [M−H]⁺

Intermediate 27

4-[4-(6,6-difluoro-3-azabicyclo[3.1.1]hept-3-yl)-3-(trifluoromethyl)phenyl]-4-oxobutanoic acid

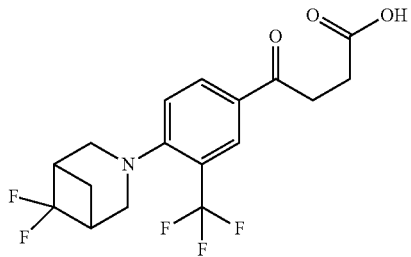 [SMILES: O=C(O)CCC(=O)c1ccc(N2CC3CC(C2)C3(F)F)c(C(F)(F)F)c1]

Prepared in analogy to Intermediate 19 from Intermediate 18.
LC-MS (Method 1): $R_t$=1.03 min; MS (ESIneg): m/z=376 [M−H]⁺

Intermediate 28

4-[4-(3,3-difluoropyrrolidin-1-yl)-3-(trifluoromethyl)phenyl]-4-oxobutanoic acid

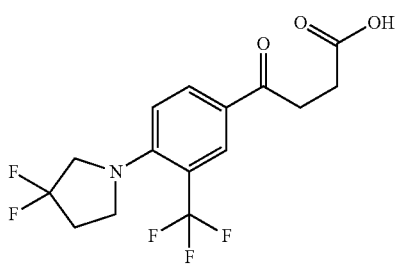 [SMILES: O=C(O)CCC(=O)c1ccc(N2CCC(F)(F)C2)c(C(F)(F)F)c1]

Prepared in analogy to Intermediate 19 from Intermediate 18.
LC-MS (Method 1): $R_t$=1.03 min; MS (ESIneg): m/z=350 [M−H]⁺

Intermediate 29

4-[4-(methylamino)-3-(trifluoromethyl)phenyl]-4-oxobutanoic acid

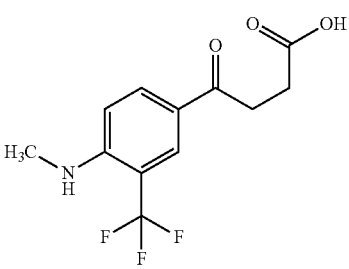 [SMILES: CNc1ccc(C(=O)CCC(=O)O)cc1C(F)(F)F]

Prepared in analogy to Intermediate 19 from Intermediate 18.
LC-MS (Method 1): $R_t$=0.91 min; MS (ESIneg): m/z=274 [M−H]⁺

Intermediate 30

4-[4-(3-hydroxyazetidin-1-yl)-3-(trifluoromethyl)phenyl]-4-oxobutanoic acid

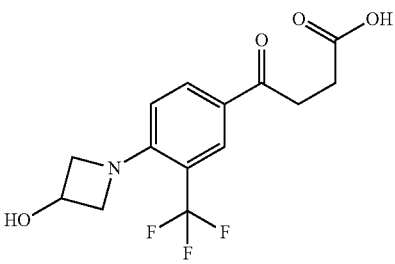 [SMILES: O=C(O)CCC(=O)c1ccc(N2CC(O)C2)c(C(F)(F)F)c1]

Prepared in analogy to Intermediate 19 from Intermediate 18.
LC-MS (Method 1): $R_t$=0.82 min; MS (ESIneg): m/z=316 [M−H]⁺

Intermediate 31

4-[4-(ethylamino)-3-(trifluoromethyl)phenyl]-4-oxobutanoic acid

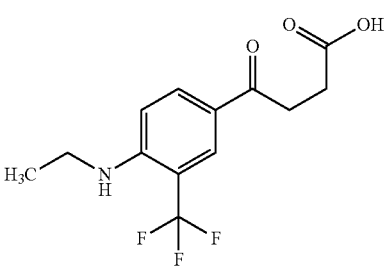 [SMILES: CCNc1ccc(C(=O)CCC(=O)O)cc1C(F)(F)F]

Prepared in analogy to Intermediate 19 from Intermediate 18.

LC-MS (Method 1): $R_t$=1.05 min; MS (ESIneg): m/z=288 [M−H]$^+$

Intermediate 32

1-[3-Fluoro-4-(morpholin-4-yl)phenyl]ethanone

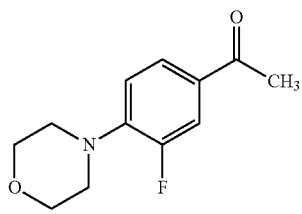 [SMILES: CC(=O)c1ccc(N2CCOCC2)c(F)c1]

1-(3,4-Difluorophenyl)ethanone (630 μL, 5.0 mmol, CAS 369-33-5) was dissolved in acetonitrile (5.0 mL), morpholine (650 μL, 7.5 mmol) and N,N-diisopropylethylamine (1.3 mL, 7.7 mmol) were added. The mixture was stirred at 80° C. for 18 h. The solvents removed in vacuo and the residue purified via chromatography (silica, gradient: hexane->hexane/ethyl acetate 7:3) to obtain the title product (210 mg, 95% purity, 18% yield).

LC-MS (Method 2): $R_t$=0.96 min; MS (ESIpos): m/z=224 [M+H]$^+$ $^1$H-NMR (400 MHz, DMSO-d$_6$) δ [ppm]: 2.327 (0.44), 2.523 (1.67), 2.667 (0.63), 3.140 (13.15), 3.152 (16.00), 3.164 (14.50), 3.735 (14.96), 3.747 (15.65), 3.758 (13.80), 7.077 (4.05), 7.098 (7.81), 7.120 (4.31), 7.636 (4.87), 7.641 (5.36), 7.672 (4.64), 7.678 (5.34), 7.728 (5.05), 7.733 (4.33), 7.749 (4.63), 7.754 (4.09).

Intermediate 33

Ethyl 4-[3-fluoro-4-(morpholin-4-yl)phenyl]-4-oxobutanoate

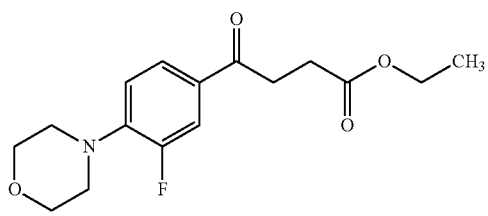 [SMILES: CCOC(=O)CCC(=O)c1ccc(N2CCOCC2)c(F)c1]

Lithium 1,1,1,3,3,3-hexamethyldisilazan-2-ide (2.1 mL, 1.0 M in THF, 2.1 mmol) was dissolved in THF (2 mL) under nitrogen atmosphere at 0° C. Then, a solution of 1-[3-fluoro-4-(morpholin-4-yl)phenyl]ethanone (450 mg, 2.02 mmol, Intermediate 32) in THF (2 mL) was slowly added. The mixture was stirred at RT for 1 h. Then, a solution of ethyl bromoacetate (230 μL, 2.1 mmol) in THF (2 mL) was added and the mixture was stirred at RT overnight. Water was added and the solvents removed in vacuo. The precipitate was purified via chromatography to obtain the title product (45.0 mg, 7% yield).

LC-MS (Method 1): Rt=1.14 min; MS (ESIpos): m/z=310 [M+H]$^+$

Intermediate 34

4-[4-(Morpholin-4-yl)-3-(trifluoromethyl)phenyl]-4-oxobutanoic acid

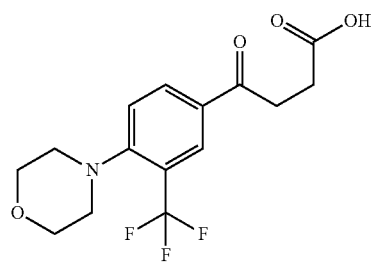 [SMILES: O=C(O)CCC(=O)c1ccc(N2CCOCC2)c(C(F)(F)F)c1]

4-[4-Fluoro-3-(trifluoromethyl)phenyl]-4-oxobutanoic acid (130 mg, 492 μmol, Intermediate 18) was dissolved in DMSO (1.0 mL) and morpholine (210 μL, 2.5 mmol) was added. The mixture was stirred at 100° C. for id. Solvents were removed to obtain the raw product that was used for the next step without purification.

LC-MS (Method 1): $R_t$=1.03 min; MS (ESIpos): m/z=332 [M+H]$^+$

Intermediate 35

2-bromo-1-[4-bromo-3-(trifluoromethyl)phenyl]ethan-1-one

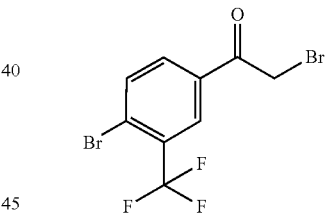

To a solution of 1-[4-bromo-3-(trifluoromethyl)phenyl]ethanone (1.00 g, 3.75 mmol, CAS 120077-70-5) in acetic acid (10.3 mL) was added bromine (193 μl, 3.75 mmol) dropwise. The resulting solution was allowed to stir for 16 h, after which time the reaction mixture was quenched by addition of sodium thiosulfite solution and extracted with ethyl acetate. The organic fraction was washed with saturated aqueous sodium hydrogen carbonate solution, saturated aqueous sodium chloride solution, dried (MgSO4), filtered and concentrated in vacuo. LCMS and NMR analysis indicated 2:1 mixture of desired product and dibrominated product. The residual material was purified by Biotage Isolera™ chromatography (silica gel, eluting with heptanes-EtOAc, 1:0 to 95:5) to afford 551 mg (39% yield) of the title compound as a golden oil. LCMS (Method 3, 2 min) 91% @ Rt 1.26 mins, MS (ESIpos): m/z no ionisation observed $^1$H NMR (250 MHz, Chloroform-d) δ=4.43 (s, 2H), 7.90 (d, J=8.4 Hz, 1H), 8.01 (dd, J=8.4, 2.1 Hz, 1H), 8.31 (d, J=2.1 Hz, 1H).

Intermediate 36 dimethyl {2-[4-bromo-3-(trifluoromethyl)phenyl]-2-oxoethyl}propanedioate

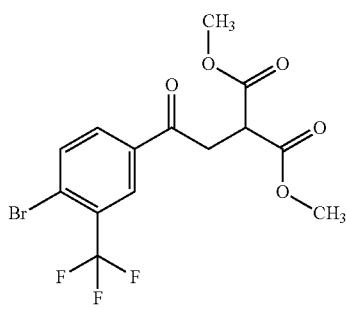 [SMILES: COC(=O)C(CC(=O)c1ccc(Br)c(C(F)(F)F)c1)C(=O)OC]

A suspension of 2-bromo-1-[4-bromo-3-(trifluoromethyl)phenyl]ethanone (Intermediate 35, 551 mg, 1.45 mmol, 91% purity), potassium carbonate (401 mg, 2.90 mmol) and dimethyl malonate (994 microL, 8.70 mmol) in acetone (5.6 mL) was heated at 50° C. for 1 hour then stirred at room temperature for 30 minutes. After this time the reaction mixture was then concentrated in vacuo, then partitioned between EtOAc and 1M hydrogen chloride solution, with the organic fraction isolated and washed with saturated aqueous sodium chloride solution, dried (MgSO4), filtered and concentrated in vacuo. The residue was purified via Biotage Isolera chromatography (using a gradient of eluents; 99:1 to 1:1 heptane:EtOAc) giving the desired product (722 mg, 74% yield; 59% purity—26% w/w dimethylmalonate indicated by $^1$H NMR analysis) as a pale yellow oil. LCMS (Method 3, 2 min) 85% @ Rt=1.22 mins, MS (ESIPos): m/z=396.75 (M+H)$^+$ $^1$H NMR (250 MHz, Chloroform-d) δ=3.42 (s, 4H), 3.63 (d, J=7.1, 2H), 3.82 (s, 6H), 4.07-4.18 (m, 1H), 7.88 (d, J=8.3, 1H), 8.00 (dd, J=8.3, 1.9, 1H), 8.29 (d, J=2.0, 1H).

Intermediate 37

4-[4-bromo-3-(trifluoromethyl)phenyl]-4-oxobutanoic acid

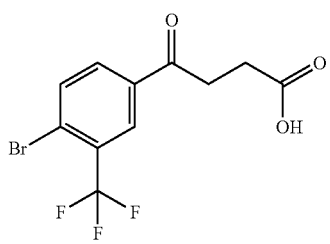 [SMILES: O=C(O)CCC(=O)c1ccc(Br)c(C(F)(F)F)c1]

A mixture of dimethyl {2-[4-bromo-3-(trifluoromethyl)phenyl]-2-oxoethyl}malonate (Intermediate 36, 720 mg, 1.07 mmol, 59% purity) and lithium hydroxide hydrate (180 mg, 4.28 mmol) in methanol/water (2:1 v:v; 6 mL) was heated to 80° C. for 16 h. After this time, the reaction mixture was concentrated in vacuo, with the resultant material partitioned between EtOAc and 1M aqueous hydrogen chloride solution. The organic layer was isolated, washed with saturated aqueous sodium chloride solution, dried (MgSO4), filtered and concentrated in vacuo. The residual material was purified by Biotage Isolera™ chromatography (25 g KP-Sil, eluting with DCM-DMAW90 (DCM:MeOH:AcOH:water 90:18:3:2 (v:v:v:v), 1:0 to 0:1) to obtain the title compound (415 mg, 75%, 63% purity) as a pale tan solid. LCMS (Method 3, 2 min) 82% @ Rt=1.02 mins MS (ESIPos): m/z=322.75 (M−H)$^+$ $^1$H NMR (250 MHz, Methanol-d4) δ=3.66 (d, J=6.8 Hz, 2H), 3.97 (t, J=6.8 Hz, 1H), 8.01 (d, J=8.4 Hz, 1H), 8.16 (dd, J=8.3, 1.9 Hz, 1H), 8.32 (d, J=1.8 Hz, 1H)-enol form predominates; OH and CO2H signals not observed

Intermediate 38

6-[4-bromo-3-(trifluoromethyl)phenyl]-4,5-dihydropyridazin-3(2H)-one

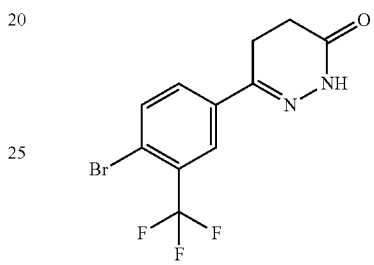

A mixture of 4-[4-bromo-3-(trifluoromethyl)phenyl]-4-oxobutanoic acid (Intermediate 37, 415 mg, 0.80 mmol) and hydrazine hydrate (80 microL, 1.61 mmol) in water (4.5 mL) was heated at 100° C. for 3 h in a sealed vessel. After this time, the reaction mixture was filtered, with the precipitate washed with further aliquots of water and isopropanol. The resulting pale yellow solid was dried in vacuo to afford the desired product (208 mg, 72%, 90% purity) as a tan solid. LCMS (Method 3, 2 min) 63% @ Rt=1.10 mins MS (ESIPos): m/z=320.80 (M−H)$^+$ $^1$H NMR (250 MHz, DMSO-d6) δ=2.43-2.49 (m, 2H), 3.01 (t, J=8.3 Hz, 2H), 7.85-8.01 (m, 2H), 8.12 (s, 1H), 11.09 (s, 1H).

Intermediate 39

6-[4-fluoro-3-(trifluoromethyl)phenyl]-4,5-dihydropyridazin-3(2H)-one

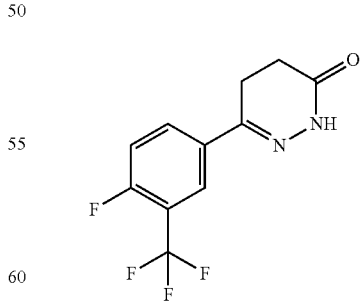

A mixture of 4-[4-fluoro-3-(trifluoromethyl)phenyl]-4-oxobutanoic acid (Intermediate 18, 513 mg, 1.75 mmol) and hydrazine hydrate (170 microL, 3.50 mmol) in water (9.8 mL) was heated at 100° C. for 3 h in a sealed vessel. After this time, the reaction mixture was filtered, with the precipitate washed with further aliquots of water and isopropanol. The resulting pale yellow solid was dried in vacuo to afford the desired product (333 mg, 73%) as a pale yellow solid. LCMS (Method 3, 2 min) 100% @ Rt=1.05 mins MS (ESIPos): no ionisation observed $^1$H NMR (250 MHz, Methanol-d4) δ=2.55-2.69 (m, 2H), 2.99-3.15 (m, 2H), 7.35-7.48 (m, 1H), 8.03-8.21 (m, 2H).

Intermediate 40

4-(3,4-difluorophenyl)-4-oxo-butanoic acid

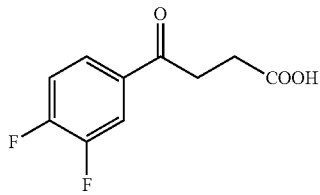 [SMILES: O=C(O)CCC(=O)c1ccc(F)c(F)c1]

To 100 mL of 1,2-dichloroethane was added 10.0 g of 1,2-difluorobenzene (87.6 mmol) and 8.76 g of succinic anhydride (87.6 mmol). To the suspension was added 23.3 g of AlCl$_3$ (175 mmol) in portions, leading to dissolution with time. After 4 h the red solution was poured onto ice with concentrated HCl, after warming the mixture was transferred to a separatory funnel and separated, the water layer was rinsed several times with CH$_2$Cl$_2$. The combined organic layers were rinsed with brine, dried (MgSO$_4$) and concentrated to a solid which was recrystallized from toluene to give 5.71 g of white crystals. The mother liquors were treated with NaOH solution, the aqueous solution was then made acidic with 1 N HCl, and rinsed with dichloromethane which was dried and concentrated. Recrystallization from toluene yielded another 710 mg of product (34%).

$^1$H NMR (400 MHz, CDCl$_3$) δ 11.15 (s, 1H), 7.91-7.71 (m, 2H), 7.36-7.22 (m, 1H), 3.27 (t, J=6.4 Hz, 2H), 2.83 (t, J=6.4 Hz, 2H). $^{19}$F NMR (376 MHz, CDCl$_3$) δ−129.32 (d, J=22.2 Hz), −135.86 (d, J=21.8 Hz). $^{13}$C NMR (101 MHz, CDCl$_3$) δ 195.28, 178.55, 153.77 (dd, J=257.3, 12.9 Hz), 150.45 (dd, J=251.1, 13.0 Hz), 133.48 (t, J=4.0 Hz), 125.06 (dd, J=7.5, 3.6 Hz), 117.59 (d, J=17.9 Hz), 117.38 (dd, J=18.0, 1.6 Hz), 33.03, 27.89. Mass 213 (M−1).

Intermediate 41

3-(3,4-difluorophenyl)-4,5-dihydro-1H-pyridazin-6-one

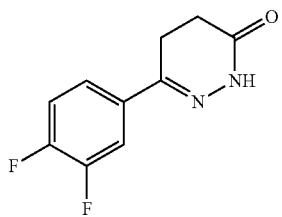 [SMILES: O=C1CCC(c2ccc(F)c(F)c2)=NN1]

To 50 mL of EtOH was added 5.7 g of 4-(3,4-difluorophenyl)-4-oxobutanoic acid (26.2 mmol, Intermediate 40) and 4.2 mL of hydrazine (133 mmol). The mixture was heated at reflux temperature 30 min before cooling, white crystals precipitated. Filtration and rinsing with cold EtOH yielded 3.40 g of product. Concentration of the mother liquors and recrystallization from EtOH yielded another 595 mg of product (71%).

$^1$H NMR (400 MHz, CDCl$_3$) δ 8.95 (br s, 1H), 7.68-7.56 (m, 1H), 7.44 (m, 1H), 7.21 (q, J=8.7 Hz, 1H), 2.97 (t, J=8.2 Hz, 2H), 2.65 (t, J=8.2 Hz, 2H). $^{19}$F NMR (376 MHz, CDCl$_3$) δ−135.27 (d, J=21.1 Hz), −136.57 (d, J=21.1 Hz). $^{13}$C NMR (101 MHz, CDCl$_3$) δ 166.96, 152.15 (dd, J=89.0, 12.9 Hz), 149.66 (dd, J=85.3, 12.9 Hz), 148.21, 132.66 (dd, J=5.8, 3.8 Hz), 122.15 (dd, J=6.6, 3.6 Hz), 117.40 (d, J=17.7 Hz), 114.98 (d, J=19.0 Hz), 26.15, 22.41. Mass 211 (M+1).

EXPERIMENTAL SECTION—EXAMPLES

Example 1

6-[4-(3,6-Dihydro-2H-pyran-4-yl)phenyl]-4,5-dihydropyridazin-3(2H)-one

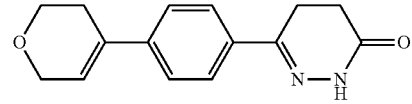 [SMILES: O=C1CCC(c2ccc(C3=CCOCC3)cc2)=NN1]

In a reaction vessel 4-(4,4,5,5-tetramethyl-1,3,2-dioxaborolan-2-yl)-3,6-dihydro-2H-pyran (157 mg, 748 µmol) and 6-(4-chlorophenyl)-4,5-dihydropyridazin-3(2H)-one (130 mg, 623 µmol, CAS 1079-73-8) were dissolved in DMF (1.5 mL, 19 mmol) and aqueous sodium carbonate solution (620 µL, 2.0 M, 1.2 mmol) was added. The mixture was degassed with argon for 5 min. Then, 1,1'-bis(diphenylphosphino)ferrocenedichloropalladium(II) (45.6 mg, 62.3 µmol) was added. The mixture was stirred at 120° C. for 1 h in a heating block. The reaction mixture was diluted with water and extracted with ethyl acetate three times. The combined organic layers were dried using a water-resistant filter and the filtrate was concentrated under reduced pressure. The residue was purified by preparative HPLC (method 5) to give 60.0 mg (95% purity, 30% yield) of the title compound.

LC-MS (Method 1): R$_t$=0.87 min; MS (ESIpos): m/z=257 [M+H]$^+$ $^1$H-NMR (400 MHz, DMSO-d$_6$) δ [ppm]: 2.074 (1.39), 2.421 (7.42), 2.440 (15.88), 2.456 (6.92), 2.462 (14.22), 2.518 (3.02), 2.522 (2.01), 2.922 (9.03), 2.944 (13.02), 2.964 (7.31), 3.810 (7.60), 3.824 (16.00), 3.837 (7.20), 4.225 (4.22), 4.231 (10.52), 4.238 (10.50), 4.245 (4.06), 6.350 (3.05), 6.354 (4.35), 6.357 (6.14), 6.361 (4.30), 6.364 (2.94), 7.497 (12.08), 7.519 (14.25), 7.719 (15.61), 7.741 (12.46), 10.925 (12.08).

Example 2

6-[3-Methyl-4-(pyridin-3-yl)phenyl]-4,5-dihydropyridazin-3(2H)-one

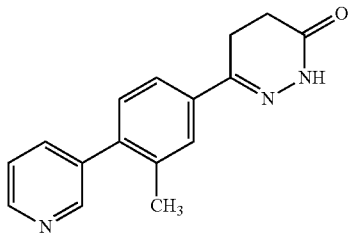 [SMILES: Cc1cc(C2=NNC(=O)CC2)ccc1-c1cccnc1]

In a reaction vessel 6-(4-chloro-3-methylphenyl)-4,5-dihydropyridazin-3(2H)-one (70.0 mg, 314 µmol, Intermediate 6), pyridin-3-ylboronic acid (77.3 mg, 629 µmol), potassium carbonate (86.9 mg, 629 µmol) and dicyclohexyl[2',4',6'-tri(propan-2-yl)biphenyl-2-yl]phosphane (8.99 mg, 18.9 µmol) were suspended in 1,4-dioxane (810 µL) and water (240 µL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.42 mg, 9.43 µmol) was added. Again, nitrogen was passed through the reaction mixture which was stirred at 80° C. overnight in a heating block. Again dicyclohexyl[2',4',6'-tri(propan-2-yl)biphenyl-2-yl]phosphane (8.99 mg, 18.9 µmol) and chloro(2-dicyclohexylphosphino-2',4',6'-triisopropyl-1,1'-biphenyl)[2-(2'-amino-1,1'-biphenyl)]palladium(II) (7.42 mg, 9.43 µmol) were added to the mixture and stirring was continued at 80° C. for 24 h. The mixture was dilute d with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 25.0 mg (95% purity, 28% yield) of the title compound title compound.

LC-MS (Method 1): Rt=0.63 min; MS (ESIpos): m/z=266 $[M+H]^+$ $^1$H-NMR (400 MHz, DMSO-$d_6$) δ [ppm]: 2.285 (16.00), 2.443 (2.83), 2.463 (5.01), 2.485 (4.65), 2.518 (1.49), 2.523 (0.97), 2.962 (3.26), 2.984 (4.91), 3.004 (2.66), 7.301 (3.21), 7.322 (3.52), 7.473 (1.50), 7.475 (1.42), 7.485 (1.53), 7.487 (1.48), 7.493 (1.65), 7.495 (1.52), 7.505 (1.65), 7.507 (1.58), 7.653 (1.65), 7.657 (1.78), 7.673 (1.41), 7.677 (1.64), 7.723 (3.14), 7.812 (1.38), 7.816 (1.97), 7.822 (1.48), 7.832 (1.28), 7.836 (1.66), 7.842 (1.26), 8.581 (3.17), 8.583 (3.85), 8.585 (4.20), 8.587 (4.27), 8.589 (4.99), 8.597 (2.52), 8.601 (2.27), 10.969 (4.66).

Example 3

6-(4'-Fluoro-2-methylbiphenyl-4-yl)-4,5-dihydropyridazin-3(2H)-one

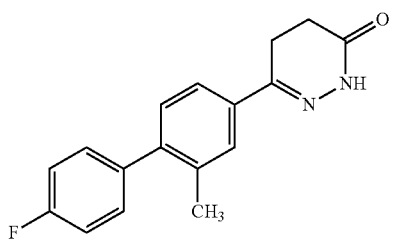 [SMILES: Cc1cc(C2=NNC(=O)CC2)ccc1-c1ccc(F)cc1]

In a reaction vessel 6-(4-chloro-3-methylphenyl)-4,5-dihydropyridazin-3(2H)-one (100 mg, 449 µmol, Intermediate 6), (4-fluorophenyl)boronic acid (126 mg, 898 µmol), potassium carbonate (124 mg, 898 µmol) and dicyclohexyl[2',4',6'-tri(propan-2-yl)biphenyl-2-yl]phosphane (12.8 mg, 26.9 µmol) were suspended in 1,4-dioxane (1.2 mL) and water (350 µL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.6 mg, 13.5 µmol) was added. Again, nitrogen was passed through the reaction mixture which was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 56.0 mg (95% purity, 42% yield) of the title compound title compound.

LC-MS (Method 1): $R_t$=1.20 min; MS (ESIpos): m/z=283 $[M+H]^+$ $^1$H-NMR (400 MHz, DMSO-$d_6$) δ [ppm]: 2.263 (16.00), 2.435 (2.71), 2.454 (5.01), 2.476 (3.59), 2.518 (2.16), 2.522 (1.39), 2.950 (3.29), 2.972 (4.97), 2.992 (2.70), 7.242 (3.22), 7.250 (0.41), 7.258 (3.12), 7.261 (4.21), 7.275 (1.23), 7.280 (5.59), 7.285 (1.18), 7.297 (1.05), 7.302 (3.54), 7.309 (0.41), 7.378 (0.42), 7.385 (3.41), 7.390 (1.34), 7.399 (3.80), 7.407 (2.87), 7.415 (1.06), 7.421 (2.43), 7.612 (1.68), 7.617 (1.81), 7.632 (1.46), 7.636 (1.67), 7.683 (3.22), 10.945 (4.82).

Example 4

6-(4'-Fluoro-2,2'-dimethylbiphenyl-4-yl)-4,5-dihydropyridazin-3(2H)-one

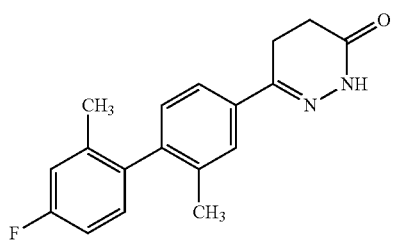 [SMILES: Cc1cc(F)ccc1-c1ccc(C2=NNC(=O)CC2)cc1C]

In a reaction vessel 6-(4-chloro-3-methylphenyl)-4,5-dihydropyridazin-3(2H)-one (110 mg, 494 µmol, Intermediate 6), (4-fluoro-2-methylphenyl)boronic acid (152 mg, 988 µmol), potassium carbonate (137 mg, 988 µmol) and dicyclohexyl[2',4',6'-tri(propan-2-yl)biphenyl-2-yl]phosphane (14.1 mg, 29.6 µmol) were suspended in 1,4-dioxane (1.3 mL) and water (380 µL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (11.7 mg, 14.8 µmol) was added. Again, nitrogen was passed through the reaction mixture which was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 72.0 mg (95% purity, 47% yield) of the title compound.

LC-MS (Method 1): $R_t$=1.27 min; MS (ESIpos): m/z=297 $[M+H]^+$

¹H-NMR (400 MHz, DMSO-d₆) δ [ppm]: 2.004 (16.00), 2.025 (14.66), 2.074 (0.67), 2.437 (2.49), 2.457 (4.48), 2.479 (3.28), 2.518 (2.29), 2.523 (1.55), 2.957 (3.01), 2.978 (4.39), 2.998 (2.49), 7.070 (1.32), 7.076 (1.62), 7.086 (2.50), 7.091 (1.49), 7.097 (1.90), 7.105 (4.04), 7.124 (3.42), 7.166 (1.34), 7.173 (1.28), 7.192 (1.29), 7.197 (1.24), 7.602 (1.51), 7.606 (1.59), 7.622 (1.34), 7.625 (1.48), 7.696 (2.81), 7.699 (2.64), 10.941 (4.42).

Example 5

6-[3-Methyl-4-(pyridin-4-yl)phenyl]-4,5-dihydro-pyridazin-3(2H)-one

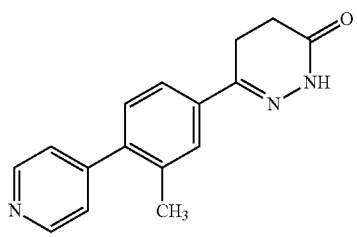 [SMILES: Cc1cc(C2=NNC(=O)CC2)ccc1-c1ccncc1]

In a reaction vessel 6-(4-chloro-3-methylphenyl)-4,5-dihydropyridazin-3(2H)-one (100 mg, 449 μmol, Intermediate 6), pyridin-4-ylboronic acid (110 mg, 898 μmol), potassium carbonate (124 mg, 898 μmol) and dicyclohexyl[2',4',6'-tri(propan-2-yl)biphenyl-2-yl]phosphane (12.8 mg, 26.9 μmol) were suspended in 1,4-dioxane (1.2 mL) and water (350 μL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.6 mg, 13.5 μmol) was added. Again, nitrogen was passed through the reaction mixture which was stirred at 80° C. for 72 h in a heating block. Again dicyclohexyl[2',4',6'-tri(propan-2-yl)biphenyl-2-yl]phosphane (12.8 mg, 26.9 μmol) and chloro(2-dicyclohexylphosphino-2',4',6'-triisopropyl-1,1'-biphenyl)[2-(2'-amino-1,1'-biphenyl)]-palladium(II) (10.6 mg, 13.5 μmol) were added to the mixture and stirring was continued at 100° C. for 72 h. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 20.0 mg (95% purity, 16% yield) of the title compound.

LC-MS (Method 1): $R_t$=0.55 min; MS (ESIpos): m/z=266 [M+H]⁺

¹H-NMR (400 MHz, DMSO-d₆) δ [ppm]: 2.300 (16.00), 2.327 (0.52), 2.332 (0.40), 2.443 (2.84), 2.463 (5.27), 2.485 (5.99), 2.518 (1.76), 2.523 (1.19), 2.669 (0.44), 2.961 (3.33), 2.982 (5.02), 3.002 (2.70), 7.302 (3.21), 7.322 (3.55), 7.408 (3.09), 7.422 (3.17), 7.661 (1.69), 7.665 (1.80), 7.681 (1.41), 7.684 (1.65), 7.721 (3.19), 8.648 (1.45), 10.979 (4.62).

Example 6

6-[3-Methyl-4-(1H-pyrazol-4-yl)phenyl]-4,5-dihydropyridazin-3(2H)-one

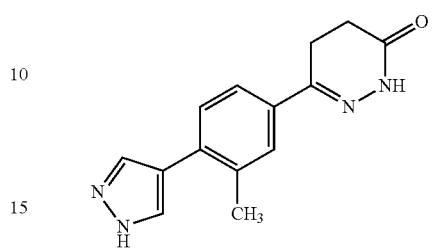

In a reaction vessel 6-(4-chloro-3-methylphenyl)-4,5-dihydropyridazin-3(2H)-one (100 mg, 449 μmol, Intermediate 6), 1H-pyrazol-4-ylboronic acid (101 mg, 898 μmol), potassium carbonate (124 mg, 898 μmol) and dicyclohexyl[2',4',6'-tri(propan-2-yl)biphenyl-2-yl]phosphane (12.8 mg, 26.9 μmol) were suspended in 1,4-dioxane (1.2 mL) and water (350 μL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.6 mg, 13.5 μmol) was added. Again, nitrogen was passed through the reaction mixture which was stirred at 80° C. for 72 h in a heating block. Again dicyclohexyl[2',4',6'-tri(propan-2-yl)biphenyl-2-yl]phosphane (12.8 mg, 26.9 μmol) and chloro(2-dicyclohexylphosphino-2',4',6'-triisopropyl-1,1'-biphenyl)[2-(2'-amino-1,1'-biphenyl)]-palladium(II) were added to the mixture and stirring was continued at 100° C. for 24 h. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 3.50 mg (95% purity, 3% yield) of the title compound.

LC-MS (Method 1): $R_t$=0.70 min; MS (ESIpos): m/z=255 [M+H]⁺

¹H-NMR (400 MHz, DMSO-d₆) δ [ppm]: 1.907 (0.61), 2.318 (0.40), 2.421 (16.00), 2.439 (4.83), 2.461 (3.65), 2.518 (4.55), 2.523 (3.12), 2.928 (3.08), 2.949 (4.43), 2.969 (2.47), 7.454 (2.70), 7.474 (3.75), 7.561 (1.71), 7.565 (1.81), 7.581 (1.14), 7.585 (1.33), 7.634 (2.82), 7.638 (2.55), 7.792 (0.53), 8.035 (0.53), 10.898 (4.76).

Example 7

6-[4-(3,6-Dihydro-2H-pyran-4-yl)-3-methylphenyl]-4,5-dihydropyridazin-3(2H)-one

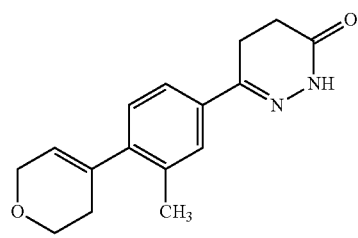 [SMILES: Cc1cc(C2=NNC(=O)CC2)ccc1C1=CCOCC1]

In a reaction vessel 6-(4-chloro-3-methylphenyl)-4,5-dihydropyridazin-3(2H)-one (100 mg, 449 μmol, Intermediate 6), 4-(4,4,5,5-tetramethyl-1,3,2-dioxaborolan-2-yl)-3,6-dihydro-2H-pyran (189 mg, 898 μmol), potassium carbonate (124 mg, 898 μmol) and dicyclohexyl[2',4',6'-tri(propan-2-yl)biphenyl-2-yl]phosphane (12.8 mg, 26.9 μmol) were suspended in 1,4-dioxane (1.2 mL) and water (350 μL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.6 mg, 13.5 μmol) was added. Again, nitrogen was passed through the reaction mixture which was stirred at Again, nitrogen was passed through the reaction mixture which was stirred at 80° C. for 72 h in a heating block. Again dicyclohexyl[2',4',6'-tri(propan-2-yl)biphenyl-2-yl]phosphane (12.8 mg, 26.9 μmol) and chloro(2-dicyclohexylphosphino-2',4',6'-triisopropyl-1,1'-biphenyl)[2-(2'-amino-1,1'-biphenyl)]palladium(II) were added to the mixture and stirring was continued at 100° C. for 24 h. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 70.0 mg (95% purity, 55% yield) of the title compound.

LC-MS (Method 1): Rt=0.95 min; MS (ESIpos): m/z=271 [M+H]$^+$ $^1$H-NMR (400 MHz, DMSO-d$_6$) δ [ppm]: 2.266 (1.62), 2.272 (2.23), 2.277 (2.25), 2.284 (1.75), 2.301 (16.00), 2.322 (0.41), 2.326 (0.51), 2.405 (2.72), 2.425 (4.80), 2.446 (3.31), 2.518 (2.00), 2.522 (1.24), 2.669 (0.48), 2.905 (3.35), 2.926 (4.87), 2.946 (2.71), 3.799 (2.84), 3.812 (6.18), 3.825 (2.73), 4.182 (1.62), 4.188 (4.40), 4.195 (4.38), 4.201 (1.64), 5.661 (1.64), 5.664 (2.41), 5.668 (1.64), 7.139 (3.10), 7.158 (3.42), 7.517 (1.57), 7.521 (1.73), 7.537 (1.34), 7.541 (1.62), 7.577 (3.04), 10.900 (4.43).

Example 8

6-(2,4'-Difluorobiphenyl-4-yl)-4,5-dihydropyridazin-3(2H)-one

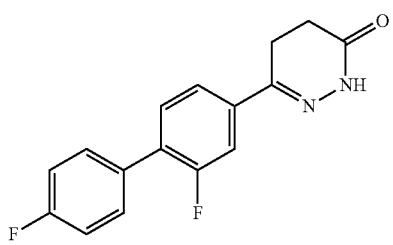 [SMILES: O=C1CCC(c2ccc(-c3ccc(F)cc3)c(F)c2)=NN1]

In a reaction vessel 6-(4-chloro-3-fluorophenyl)-4,5-dihydropyridazin-3(2H)-one (100 mg, 441 μmol, Intermediate 9), (4-fluorophenyl)boronic acid (123 mg, 882 μmol), potassium carbonate (122 mg, 882 μmol) and dicyclohexyl[2',4',6'-tri(propan-2-yl)biphenyl-2-yl]phosphane (12.6 mg, 26.5 μmol) were suspended in 1,4-dioxane (1.1 mL) and water (340 μL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.4 mg, 13.2 μmol) was added. Again, nitrogen was passed through the reaction mixture which was stirred at Again, nitrogen was passed through the reaction mixture which was stirred at 80° C. over night in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC (method 5) to give 22.0 mg (95% purity, 17% yield) of the title compound.

LC-MS (Method 1): R$_t$=1.16 min; MS (ESIpos): m/z=287 [M+H]$^+$ $^1$H-NMR (400 MHz, DMSO-d$_6$) δ [ppm]: 2.074 (0.43), 2.454 (6.99), 2.474 (14.16), 2.518 (4.32), 2.523 (3.11), 2.966 (8.26), 2.987 (12.03), 3.007 (6.56), 7.308 (0.83), 7.315 (7.71), 7.321 (2.30), 7.332 (2.94), 7.337 (16.00), 7.343 (2.71), 7.354 (2.56), 7.360 (8.06), 7.367 (0.81), 7.577 (3.45), 7.597 (7.22), 7.619 (7.80), 7.623 (5.81), 7.629 (6.56), 7.633 (9.50), 7.636 (6.59), 7.641 (5.58), 7.645 (4.14), 7.649 (2.19), 7.655 (4.89), 7.663 (15.71), 7.668 (5.06), 7.684 (4.81), 7.688 (3.63), 11.046 (11.45).

Example 9

6-(3'-Amino-4'-chloro-2-fluorobiphenyl-4-yl)-4,5-dihydropyridazin-3(2H)-one

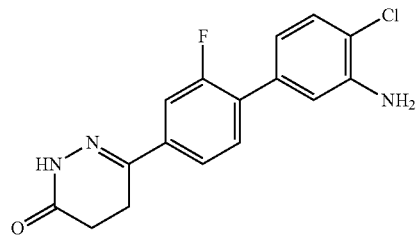 [SMILES: Nc1cc(-c2ccc(C3=NNC(=O)CC3)cc2F)ccc1Cl]

The reaction mixture was conducted in metal racks equipped with 48 glass vials. To (3-amino-4-chlorophenyl)boronic acid (51.4 mg, 300 μmol), a solution of 6-(4-chloro-3-fluorophenyl)-4,5-dihydropyridazin-3(2H)-one (34.0 mg, 150 μmol, Intermediate 9) in 1,4-dioxane (2.0 mL), dicyclohexyl[2',4',6'-tri(propan-2-yl)biphenyl-2-yl]phosphane (7.15 mg, 15.0 μmol), chloro(2-dicyclohexylphosphino-2',4',6'-triisopropyl-1,1'-biphenyl)[2-(2'-amino-1,1'-biphenyl)]palladium(II) (11.8 mg, 15.0 μmol) and potassium carbonate (330 μL, 0.90 M, 300 μmol) were added. The reaction mixture was heated for 16 h at 100° C. The samples were filtered about Alox N and purified by preparative HPLC to give 2.00 mg (100% purity, 4% yield) of the title compound.

LC-MS (Method 1): R$_t$=1.05 min; MS (ESIpo): m/z=318 [M+H]$^+$

Example 10

6-(3-Chloro-4-methoxyphenyl)-4,5-dihydropyridazin-3(2H)-one

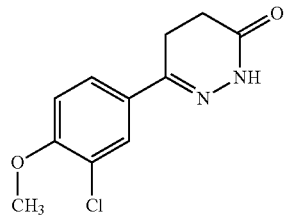 [SMILES: COc1ccc(C2=NNC(=O)CC2)cc1Cl]

4-(3-Chloro-4-methoxyphenyl)-4-oxobutanoic acid (750 mg, 3.09 mmol, CAS 39496-87-2) was diluted with hydrazine hydrate (1:1) (560 µL, 80% purity, 9.3 mmol) and this solution was heated at 95° C. overnight. Under stirring the reaction mixture was poured into water and a grey precipitate was filtered off. The filtrate was concentrated under reduced pressure and then suspended in dichloromethane and the precipitated solid was filtered off under vacuo. The filtrate was purified by flash chromatography using a silica column, gradient hexane/ethyl acetate 0-100% to give 48.0 mg (95% purity, 6% yield) of the title compound.

LC-MS (Method 1): Rt=0.90 min; MS (ESIpos): m/z=239 [M+H]$^+$ $^1$H-NMR (400 MHz, DMSO-d$_6$) € [ppm]: 1.171 (0.60), 1.986 (1.06), 2.402 (2.18), 2.422 (3.78), 2.444 (2.52), 2.518 (1.22), 2.523 (0.79), 2.894 (2.65), 2.915 (3.82), 2.935 (2.05), 3.890 (16.00), 7.183 (2.49), 7.205 (2.79), 7.672 (1.62), 7.678 (1.78), 7.693 (1.64), 7.699 (1.68), 7.781 (3.45), 7.786 (3.20), 10.896 (2.81).

Example 11

6-(4-Chloro-3-methylphenyl)-4,5-dihydropyridazin-3(2H)-one

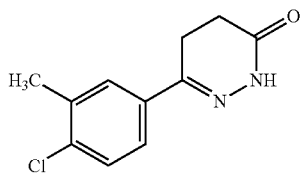

4-(4-Chloro-3-methylphenyl)-4-oxobutanoic acid (2.75 g, 12.1 mmol; Intermediate 5) was dissolved in 1-propanol (4 mL) and hydrazine hydrate (1:1) (3.0 mL, 100% purity, 61 mmol) was added. The mixture was heated at 100° C. for one h. After cooling to room temperature under stirring the reaction mixture was poured into water and precipitated product was filtered off under vacuo. It was purified by preparative HPLC (Preparation-Instrument: Waters Autopurificationsystem; column: Waters XBrigde C18 5µ 100×30 mm; Eluent A: water+0.2 Vol-% aqueous ammonia (32%), Eluent B: Acetonitrile; Gradient: 0.00-0.50 min 25% B (25->70 mL/min), 0.51-5.50 min 25-50% B (70 mL/min), DAD scan: 210-400 nm) to give 1.60 g (95% purity, 56% yield) of the title compound.

LC-MS (Method 1): Rt=1.04 min; MS (ESIpos): m/z=223 [M+H]$^+$ $^1$H-NMR (400 MHz, DMSO-d$_6$) δ [ppm]: 2.363 (16.00), 2.420 (2.73), 2.441 (5.00), 2.461 (3.32), 2.522 (0.67), 2.911 (3.25), 2.933 (5.03), 2.953 (2.65), 7.442 (2.81), 7.463 (3.84), 7.569 (1.77), 7.574 (1.88), 7.590 (1.25), 7.595 (1.35), 7.722 (2.85), 7.726 (2.67), 10.962 (3.29).

Example 12

6-[4-(4,4-Difluoropiperidin-1-yl)-3,5-difluorophenyl]-4,5-dihydropyridazin-3(2H)-one

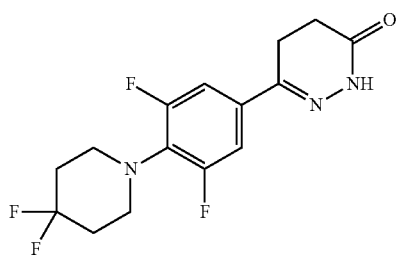 [SMILES: O=C1CCC(c2cc(F)c(N3CCC(F)(F)CC3)c(F)c2)=NN1]

4-[4-(4,4-Difluoropiperidin-1-yl)-3,5-difluorophenyl]-4-oxobutanoic acid (287 mg, 861 µmol; Intermediate 19) was diluted with hydrazine hydrate (1:1) (520 µL, 80% purity, 8.6 mmol) and this solution was heated at 100° C. overnight. After cooling to room temperature under stirring the reaction mixture was poured into water and extracted with ethyl acetate three times. The crude material was purified by preparative HPLC (Method 5) to give 10.0 mg (95% purity, 3% yield) of the title compound.

LC-MS (Method 1): R$_t$=1.17 min; MS (ESIpos): m/z=330 [M+H]$^+$ $^1$H-NMR (400 MHz, DMSO-d$_6$) δ [ppm]: 1.906 (1.26), 2.028 (3.02), 2.042 (4.63), 2.062 (6.54), 2.074 (15.75), 2.091 (6.49), 2.112 (4.78), 2.126 (3.12), 2.323 (2.01), 2.327 (2.72), 2.332 (2.01), 2.403 (7.95), 2.423 (15.25), 2.444 (9.81), 2.522 (9.16), 2.665 (2.01), 2.669 (2.72), 2.673 (2.01), 2.878 (9.41), 2.899 (14.99), 2.919 (7.80), 3.240 (10.47), 3.254 (16.00), 3.266 (10.57), 7.369 (1.01), 7.376 (1.76), 7.390 (12.03), 7.418 (12.43), 7.431 (1.81), 7.438 (1.21), 10.996 (14.19).

Example 13

6-[4-(3,3-Difluoropyrrolidin-1-yl)-3,5-difluorophenyl]-4,5-dihydropyridazin-3(2H)-one

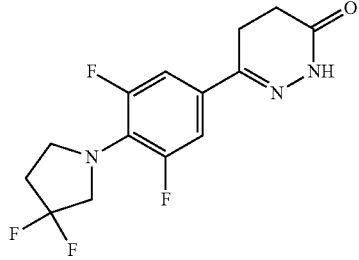 [SMILES: O=C1CCC(c2cc(F)c(N3CCC(F)(F)C3)c(F)c2)=NN1]

4-[4-(3,3-Difluoropyrrolidin-1-yl)-3,5-difluorophenyl]-4-oxobutanoic acid (275 mg, 861 µmol; Intermediate 20) was diluted with hydrazine hydrate (1:1) (520 µL, 80% purity, 8.6 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 23.0 mg (95% purity, 8% yield) of the title compound.

LC-MS (Method 1): $R_t$=1.12 min; MS (ESIpos): m/z=316 [M+H]$^+$ $^1$H-NMR (400 MHz, DMSO-d$_6$) δ [ppm]: 1.906 (0.43), 2.074 (11.81), 2.323 (1.03), 2.326 (1.37), 2.331 (1.01), 2.375 (1.78), 2.394 (10.08), 2.414 (16.00), 2.466 (3.80), 2.522 (3.71), 2.665 (1.03), 2.669 (1.37), 2.673 (1.01), 2.861 (8.47), 2.882 (12.94), 2.902 (6.88), 3.694 (4.35), 3.712 (8.11), 3.730 (4.16), 3.822 (3.99), 3.855 (7.94), 3.889 (3.97), 7.333 (0.79), 7.341 (1.23), 7.360 (9.41), 7.363 (6.57), 7.388 (6.81), 7.391 (9.17), 7.410 (1.23), 7.418 (0.84), 10.944 (12.10).

Example 14

6-[4-(3-Azabicyclo[3.1.0]hex-3-yl)-3,5-difluorophenyl]-4,5-dihydropyridazin-3(2H)-one

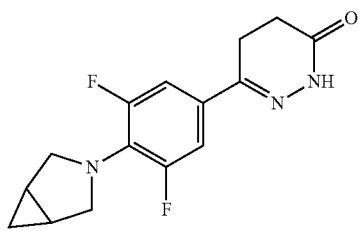 [SMILES: O=C1CCC(c2cc(F)c(N3CC4CC4C3)c(F)c2)=NN1]

4-[4-(3-Azabicyclo[3.1.0]hex-3-yl)-3,5-difluorophenyl]-4-oxobutanoic acid (203 mg, 689 µmol; Intermediate 21) was diluted with hydrazine hydrate (1:1) (420 µL, 80% purity, 6.9 mmol) and this solution was heated at 100° C. for 6 h. After cooling to room temperature under stirring the reaction mixture was poured into water and extracted with ethyl acetate three times. Solvents were removed in vacuo. The crude material was purified by preparative HPLC (Method 5) to give 20.0 mg (95% purity, 9% yield) of the title compound.

LC-MS (Method 1): $R_t$=1.24 min; MS (ESIpos): m/z=292 [M+H]$^+$ $^1$H-NMR (400 MHz, DMSO-d$_6$) δ [ppm]: 0.345 (1.86), 0.355 (5.31), 0.365 (5.62), 0.375 (2.16), 0.539 (1.83), 0.550 (2.30), 0.558 (4.26), 0.569 (4.19), 0.577 (2.60), 0.588 (2.03), 1.542 (5.85), 1.545 (4.94), 1.548 (4.77), 1.551 (6.46), 1.556 (5.04), 1.560 (5.82), 1.564 (4.43), 1.905 (1.01), 2.074 (9.23), 2.318 (0.58), 2.380 (8.42), 2.399 (15.53), 2.421 (10.55), 2.472 (0.61), 2.518 (8.93), 2.523 (5.95), 2.660 (0.58), 2.839 (10.38), 2.861 (16.00), 2.881 (8.46), 3.478 (4.90), 3.501 (8.59), 3.557 (14.92), 3.580 (8.25), 7.271 (0.88), 7.279 (1.49), 7.297 (12.21), 7.301 (7.34), 7.325 (7.48), 7.329 (11.53), 7.347 (1.49), 7.355 (1.01), 10.908 (13.36).

Example 15

2-(Morpholin-4-yl)-5-(6-oxo-1,4,5,6-tetrahydropyridazin-3-yl)benzonitrile

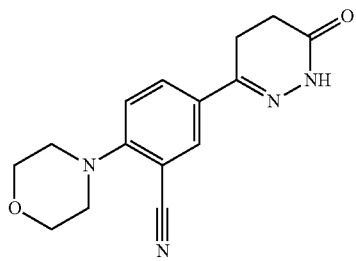 [SMILES: N#Cc1cc(C2=NNC(=O)CC2)ccc1N1CCOCC1]

4-[3-Cyano-4-(morpholin-4-yl)phenyl]-4-oxobutanoic acid (500 mg, 1.73 mmol, Intermediate 13) was diluted with hydrazine hydrate (1:1) (840 µL, 17 mmol) and this solution was heated at 100° C. overnight. After cooling to room temperature under stirring the reaction mixture was poured into water and extracted with ethyl acetate three times. The crude material was purified by flash chromatography. Received product again was purified by preparative HPLC to give 60.0 mg (95% purity, 12% yield) of the title compound. LC-MS (Method 1): $R_t$=0.80 min; MS (ESIpos): m/z=285 [M+H]$^+$ $^1$H-NMR (400 MHz, DMSO-d$_6$) δ [ppm]: 2.074 (2.34), 2.407 (7.43), 2.428 (14.20), 2.449 (8.98), 2.518 (4.46), 2.523 (2.80), 2.910 (9.16), 2.931 (13.70), 2.951 (7.45), 3.205 (12.61), 3.217 (16.00), 3.229 (13.74), 3.755 (14.37), 3.767 (15.64), 3.778 (13.01), 7.193 (8.80), 7.215 (9.24), 7.959 (5.61), 7.964 (7.02), 7.980 (4.30), 7.986 (7.00), 8.002 (13.01), 8.007 (9.36), 10.950 (13.38).

Example 16

6-[3,5-Difluoro-4-(piperidin-1-yl)phenyl]-4,5-dihydropyridazin-3(2H)-one

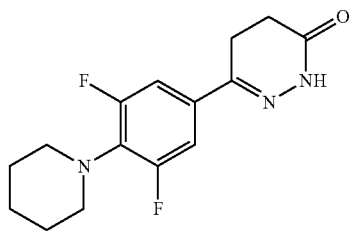 [SMILES: O=C1CCC(c2cc(F)c(N3CCCCC3)c(F)c2)=NN1]

4-[3,5-Difluoro-4-(piperidin-1-yl)phenyl]-4-oxobutanoic acid (192 mg, 646 µmol; Intermediate 23) was diluted with hydrazine hydrate (1:1) (390 µL, 80% purity, 6.5 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 6.00 mg (90% purity, 3% yield) of the title compound.

LC-MS (Method 1): Rt=1.28 min; MS (ESIpos): m/z=294 [M+H]$^+$ $^1$H-NMR (400 MHz, CDCl$_3$) δ [ppm]: 1.604 (5.66), 1.617 (5.73), 1.624 (4.17), 1.629 (4.00), 1.660 (5.01), 1.673 (9.11), 1.686 (11.35), 1.699 (6.60), 1.713 (2.89), 2.020 (2.96), 2.058 (0.55), 2.584 (7.08), 2.603 (16.00), 2.607 (8.02), 2.625 (10.27), 2.883 (10.46), 2.900 (7.64), 2.904 (15.76), 2.923 (7.13), 3.177 (9.18), 3.182 (8.27), 3.191 (12.14), 3.203 (8.22), 7.006 (1.16), 7.164 (0.92), 7.172 (1.47), 7.188 (11.66), 7.191 (6.75), 7.213 (6.75), 7.216 (12.12), 7.232 (1.47), 7.240 (1.04), 7.529 (1.20), 8.458 (4.27).

Example 17

6-{3,5-Difluoro-4-[2-methyl-3-azabicyclo[3.1.0]hex-3-yl]phenyl}-4,5-dihydropyridazin-3(2H)-one

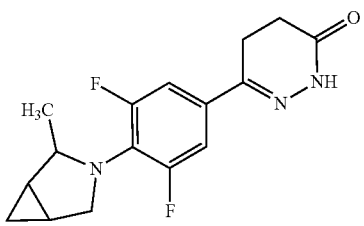 [SMILES: CC1C2CC2CN1c1c(F)cc(C2=NNC(=O)CC2)cc1F]

4-{3,5-Difluoro-4-[2-methyl-3-azabicyclo[3.1.0]hex-3-yl]phenyl}-4-oxobutanoic acid (213 mg, 689 μmol; Intermediate 24) was diluted with hydrazine hydrate (1:1) (420 μL, 80% purity, 6.9 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 7.00 mg (95% purity, 3% yield) of the title compound.

LC-MS (Method 1): $R_t$=1.32 min; MS (ESIpos): m/z=306 [M+H]$^+$ $^1$H-NMR (400 MHz, DMSO-d$_6$) δ [ppm]: 0.384 (1.23), 0.395 (1.90), 0.403 (2.84), 0.414 (3.34), 0.422 (1.90), 0.433 (1.56), 0.540 (1.56), 0.550 (3.74), 0.560 (3.57), 0.569 (1.28), 0.947 (16.00), 0.961 (15.89), 1.016 (0.45), 1.030 (0.39), 1.472 (0.72), 1.481 (1.28), 1.489 (2.12), 1.498 (2.90), 1.507 (2.45), 1.517 (1.84), 1.526 (1.00), 1.564 (1.06), 1.573 (1.95), 1.582 (2.62), 1.591 (3.01), 1.600 (2.29), 1.609 (1.51), 1.619 (0.78), 1.907 (2.06), 2.074 (2.06), 2.327 (3.12), 2.331 (2.29), 2.336 (1.06), 2.395 (5.46), 2.416 (13.10), 2.437 (7.41), 2.518 (12.21), 2.523 (8.14), 2.539 (1.45), 2.669 (3.23), 2.673 (2.34), 2.678 (1.06), 2.842 (0.39), 2.866 (4.52), 2.869 (4.35), 2.886 (6.52), 2.890 (7.64), 2.907 (3.07), 2.911 (3.34), 3.166 (2.62), 3.175 (2.90), 3.188 (3.51), 3.197 (2.90), 3.210 (0.45), 3.499 (5.46), 3.521 (4.79), 4.001 (1.90), 4.006 (1.95), 4.015 (1.51), 7.346 (8.98), 7.376 (8.81), 7.424 (0.45), 10.973 (9.42).

Example 18

6-[4-(Ethylamino)-3-(trifluoromethyl)phenyl]-4,5-dihydropyridazin-3(2H)-one

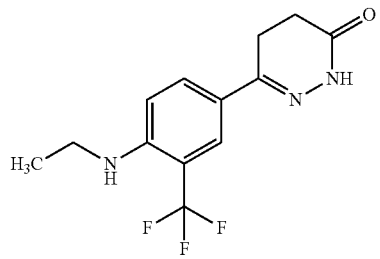 [SMILES: CCNc1ccc(C2=NNC(=O)CC2)cc1C(F)(F)F]

4-[4-(Ethylamino)-3-(trifluoromethyl)phenyl]-4-oxobutanoic acid (175 mg, 606 μmol; Intermediate 31) was diluted with hydrazine hydrate (1:1) (150 μL, 3.0 mmol) and this solution was heated at 100° C. overnight. After cooling to room temperature under stirring the reaction mixture was poured into water and precipitated product was filtered off. The filter cake was suspended in MTBE and the product was filtered off under vacuo to give 95.0 mg (95% purity, 52% yield) of the title compound.

LC-MS (Method 1): Rt=1.08 min; MS (ESIpos): m/z=286 [M+H]$^+$ $^1$H-NMR (400 MHz, DMSO-d6) δ[ppm]: 1.127 (6.91), 1.145 (16.00), 1.163 (6.93), 2.332 (0.45), 2.374 (3.52), 2.394 (6.33), 2.415 (4.20), 2.518 (2.71), 2.522 (1.97), 2.540 (0.56), 2.673 (0.51), 2.753 (0.44), 2.858 (4.38), 2.879 (6.32), 2.899 (3.47), 3.233 (0.88), 3.250 (2.84), 3.266 (3.39), 3.283 (2.74), 3.301 (0.87), 5.732 (1.00), 5.746 (1.95), 5.761 (0.98), 6.841 (2.39), 6.865 (2.47), 7.769 (2.66), 7.787 (8.16), 9.848 (0.63), 10.764 (5.77).

Example 19

6-[4-(3,3-Difluoroazetidin-1-yl)-3-(trifluoromethyl)phenyl]-4,5-dihydropyridazin-3(2H)-one

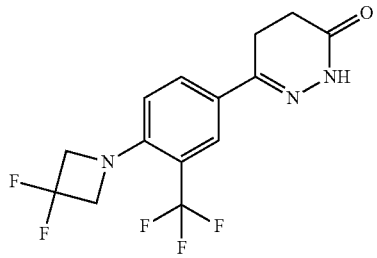 [SMILES: O=C1CCC(c2ccc(N3CC(F)(F)C3)c(C(F)(F)F)c2)=NN1]

4-[4-(3,3-Difluoroazetidin-1-yl)-3-(trifluoromethyl)phenyl]-4-oxobutanoic acid (204 mg, 606 μmol, Intermediate 25) was diluted with hydrazine hydrate (1:1) (150 μL, 3.0 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 12.0 mg (90% purity, 5% yield) of the title compound.

LC-MS (Method 1): $R_t$=1.13 min; MS (ESIpos): m/z=334 [M+H]$^+$ $^1$H-NMR (400 MHz, DMSO-d$_6$) δ [ppm]: 1.906 (0.80), 2.074 (7.85), 2.331 (2.25), 2.382 (0.51), 2.403 (7.20), 2.423 (12.87), 2.444 (8.80), 2.518 (12.58), 2.523 (8.51), 2.673 (2.25), 2.874 (0.51), 2.905 (8.15), 2.926 (12.00), 2.946 (6.62), 3.000 (0.51), 3.061 (0.44), 3.095 (0.58), 3.700 (0.44), 3.725 (0.80), 3.756 (1.24), 3.787 (0.65), 4.451 (7.93), 4.482 (16.00), 4.513 (7.85), 6.769 (5.89), 6.791 (6.11), 7.810 (0.73), 7.850 (3.93), 7.855 (4.22), 7.872 (3.49), 7.877 (4.07), 7.915 (8.65), 7.920 (7.13), 10.800 (0.73), 10.872 (11.20).

Example 20

6-{4-[2-Methylpyrrolidin-1-yl]-3-(trifluoromethyl)phenyl}-4,5-dihydropyridazin-3(2H)-one

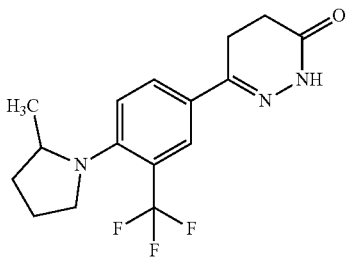 [SMILES: CC1CCCN1c1ccc(C2=NNC(=O)CC2)cc1C(F)(F)F]

4-{4-[2-Methylpyrrolidin-1-yl]-3-(trifluoromethyl)phenyl}-4-oxobutanoic acid (200 mg, 606 µmol; Intermediate 26) was diluted with hydrazine hydrate (1:1) (290 µL, 6.1 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 34.0 mg (90% purity, 16% yield) of the title compound.

LC-MS (Method 1): Rt=1.30 min; MS (ESIpos): m/z=326 [M+H]$^+$ $^1$H-NMR (400 MHz, DMSO-d$_6$) δ [ppm]: 0.995 (15.68), 1.010 (16.00), 1.041 (1.01), 1.047 (1.05), 1.057 (1.17), 1.062 (1.05), 1.092 (1.29), 1.107 (1.29), 1.176 (0.44), 1.192 (0.44), 1.472 (0.52), 1.494 (1.13), 1.520 (1.53), 1.548 (1.41), 1.570 (0.84), 1.727 (0.84), 1.746 (1.05), 1.756 (1.37), 1.776 (1.49), 1.802 (1.01), 1.821 (0.40), 1.859 (0.80), 1.867 (1.21), 1.878 (1.41), 1.887 (1.49), 1.897 (1.41), 1.906 (1.69), 1.916 (0.88), 1.925 (0.64), 2.122 (0.68), 2.129 (0.68), 2.146 (1.17), 2.158 (1.29), 2.170 (1.17), 2.187 (0.72), 2.407 (4.74), 2.428 (9.81), 2.449 (6.47), 2.518 (8.44), 2.523 (5.87), 2.910 (5.31), 2.932 (7.36), 2.952 (3.30), 2.996 (1.01), 3.010 (1.69), 3.018 (1.65), 3.031 (0.96), 3.039 (0.84), 3.494 (0.96), 3.515 (2.05), 3.534 (1.97), 3.554 (0.84), 3.794 (0.92), 3.809 (1.49), 3.830 (1.41), 3.846 (0.88), 7.157 (0.44), 7.179 (0.40), 7.274 (3.82), 7.296 (4.10), 7.838 (2.69), 7.844 (2.89), 7.861 (2.45), 7.866 (2.61), 7.943 (6.43), 7.949 (5.83), 8.078 (0.68), 8.083 (0.60), 10.889 (7.76).

Example 21

6-[4-(6,6-Difluoro-3-azabicyclo[3.1.1]hept-3-yl)-3-(trifluoromethyl)phenyl]-4,5-dihydropyridazin-3(2H)-one

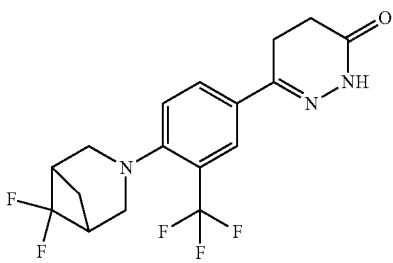 [SMILES: O=C1CCC(c2ccc(N3CC4CC(C3)C4(F)F)c(C(F)(F)F)c2)=NN1]

4-[4-(6,6-Difluoro-3-azabicyclo[3.1.1]hept-3-yl)-3-(trifluoromethyl)phenyl]-4-oxobutanoic acid (229 mg, 606 µmol; Intermediate 27) was diluted with hydrazine hydrate (1:1) (290 µL, 6.1 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 26.0 mg (95% purity, 11% yield) of the title compound.

LC-MS (Method 1): R$_t$=1.22 min; MS (ESIpos): m/z=374 [M+H]$^+$ $^1$H-NMR (400 MHz, DMSO-d$_6$) δ [ppm]: 2.074 (3.25), 2.327 (2.77), 2.331 (2.29), 2.355 (0.81), 2.373 (1.29), 2.388 (1.96), 2.405 (1.53), 2.431 (8.93), 2.451 (15.67), 2.472 (12.51), 2.669 (3.30), 2.673 (2.72), 2.691 (1.29), 2.704 (1.43), 2.714 (1.58), 2.727 (1.77), 2.739 (2.05), 2.749 (1.86), 2.761 (1.34), 2.773 (1.15), 2.785 (1.15), 2.796 (1.15), 2.831 (2.72), 2.848 (2.67), 2.945 (9.22), 2.966 (16.00), 2.986 (10.70), 2.995 (4.44), 3.005 (3.15), 3.029 (3.77), 3.049 (3.10), 3.186 (7.64), 3.209 (6.30), 3.471 (7.31), 3.497 (6.54), 7.520 (6.69), 7.542 (7.31), 7.927 (4.49), 7.932 (5.30), 7.949 (4.01), 7.954 (4.73), 8.016 (9.84), 8.021 (9.65), 10.970 (13.85).

Example 22

6-[4-(3,3-Difluoropyrrolidin-1-yl)-3-(trifluoromethyl)phenyl]-4,5-dihydropyridazin-3(2H)-one

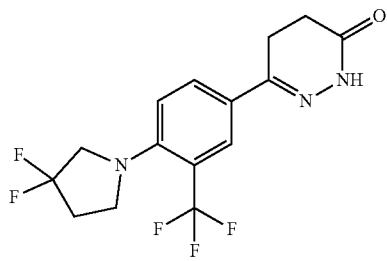 [SMILES: O=C1CCC(c2ccc(N3CCC(F)(F)C3)c(C(F)(F)F)c2)=NN1]

4-[4-(3,3-Difluoropyrrolidin-1-yl)-3-(trifluoromethyl)phenyl]-4-oxobutanoic acid (213 mg, 606 µmol, Intermediate 28) was diluted with hydrazine hydrate (1:1) (290 µL, 6.1 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 20.0 mg (95% purity, 9% yield) of the title compound.

LC-MS (Method 1): R$_t$=1.16 min; MS (ESIpos): m/z=348 [M+H]$^+$ $^1$H-NMR (400 MHz, DMSO-d$_6$) δ [ppm]: 1.193 (0.90), 1.209 (0.83), 1.906 (0.83), 2.073 (6.76), 2.417 (7.14), 2.437 (14.35), 2.458 (11.19), 2.473 (10.97), 2.518 (16.00), 2.522 (10.82), 2.544 (2.63), 2.924 (8.04), 2.945 (12.17), 2.965 (6.54), 3.481 (6.46), 3.499 (11.79), 3.516 (5.93), 3.600 (0.53), 3.636 (5.63), 3.669 (10.97), 3.702 (5.48), 3.801 (0.45), 7.291 (5.93), 7.312 (6.16), 7.881 (3.91), 7.886 (4.21), 7.902 (3.53), 7.908 (3.83), 7.987 (8.86), 7.992 (7.89), 8.173 (0.83), 10.925 (11.34).

Example 23

6-[4-(Methylamino)-3-(trifluoromethyl)phenyl]-4,5-dihydropyridazin-3(2H)-one

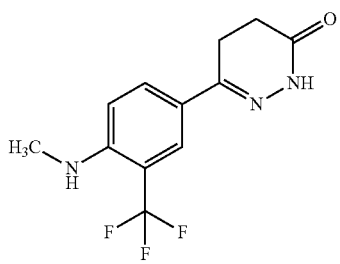 [SMILES: CNc1ccc(C2=NNC(=O)CC2)cc1C(F)(F)F]

4-[4-(Methylamino)-3-(trifluoromethyl)phenyl]-4-oxobutanoic acid (166 mg, 603 µmol; Intermediate 29) was diluted with hydrazine hydrate (1:1) (150 µL, 3.0 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 11.4 mg (95% purity, 7% yield) of the title compound.

LC-MS (Method 1): $R_t$=0.95 min; MS (ESIpos): m/z=272 [M+H]$^+$ $^1$H-NMR (400 MHz, DMSO-d$_6$) δ [ppm]: 2.331 (1.56), 2.376 (5.02), 2.395 (9.04), 2.417 (6.10), 2.518 (9.23), 2.522 (5.84), 2.801 (15.89), 2.813 (16.00), 2.831 (0.74), 2.863 (6.21), 2.884 (9.08), 2.904 (5.02), 6.020 (2.34), 6.032 (2.34), 6.761 (3.61), 6.782 (3.72), 7.790 (12.50), 7.810 (3.01), 7.925 (0.41), 10.764 (8.41).

Example 24

6-[4-(3-Hydroxyazetidin-1-yl)-3-(trifluoromethyl)phenyl]-4,5-dihydropyridazin-3(2H)-one

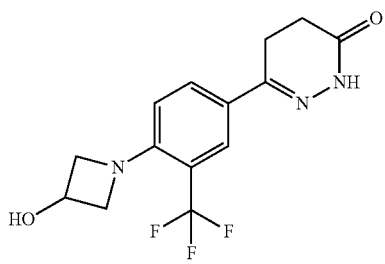 [SMILES: O=C1CCC(c2ccc(N3CC(O)C3)c(C(F)(F)F)c2)=NN1]

4-[4-(3-Hydroxyazetidin-1-yl)-3-(trifluoromethyl)phenyl]-4-oxobutanoic acid (214 mg, 605 µmol, Intermediate 30) was diluted with hydrazine hydrate (1:1) (150 µL, 3.0 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 25.0 mg (95% purity, 13% yield) of the title compound.

LC-MS (Method 1): Rt=0.82 min; MS (ESIpos): m/z=314 [M+H]$^+$ $^1$H-NMR (400 MHz, DMSO-d$_6$) δ [ppm]: 1.231 (0.44), 1.949 (0.70), 2.041 (0.65), 2.074 (16.00), 2.084 (3.14), 2.331 (1.79), 2.383 (7.02), 2.402 (12.56), 2.424 (8.68), 2.518 (9.29), 2.523 (6.15), 2.673 (1.79), 2.872 (8.46), 2.893 (12.34), 2.914 (6.71), 3.083 (0.44), 3.763 (3.88), 3.775 (4.40), 3.783 (4.53), 3.794 (4.05), 4.246 (4.01), 4.264 (6.58), 4.283 (3.92), 4.529 (2.40), 4.543 (2.22), 5.703 (3.05), 5.718 (3.01), 6.605 (6.41), 6.627 (6.54), 7.277 (0.44), 7.774 (4.14), 7.779 (4.58), 7.796 (3.75), 7.801 (4.49), 7.838 (9.11), 7.844 (7.63), 10.804 (12.82).

Example 25

6-[3-Fluoro-4-(morpholin-4-yl)phenyl]-4,5-dihydropyridazin-3(2H)-one

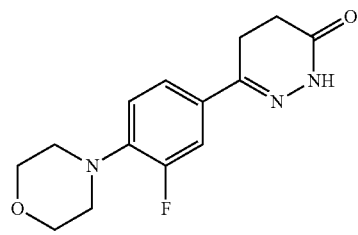 [SMILES: O=C1CCC(c2ccc(N3CCOCC3)c(F)c2)=NN1]

Ethyl 4-[3-fluoro-4-(morpholin-4-yl)phenyl]-4-oxobutanoate (45.0 mg, 145 µmol; Intermediate 33) was dissolved in ethanol (2.0 mL), diluted with hydrazine hydrate (1:1) (88 µL, 80% purity, 1.5 mmol) and this solution was heated at 100° C. overnight. The mixture was concentrated under reduced pressure. The crude material was purified by preparative HPLC (Method 5) to give 10.0 mg (95% purity, 24% yield) of the title compound.

LC-MS (Method 1): $R_t$=0.83 min; MS (ESIpos): m/z=278 [M+H]$^+$ $^1$H-NMR (400 MHz, DMSO-d$_6$) δ [ppm]: 2.331 (1.76), 2.395 (7.06), 2.414 (13.29), 2.436 (8.69), 2.518 (12.35), 2.523 (7.56), 2.673 (1.76), 2.877 (8.82), 2.898 (13.29), 2.918 (7.18), 3.042 (12.54), 3.053 (16.00), 3.065 (13.42), 3.731 (13.98), 3.743 (15.87), 3.754 (13.10), 7.030 (3.40), 7.051 (5.92), 7.074 (3.78), 7.476 (3.65), 7.481 (8.44), 7.507 (5.35), 7.513 (6.61), 7.518 (3.72), 10.885 (12.16).

Example 26

6-(4'-Fluoro-2'-methylbiphenyl-4-yl)-4,5-dihydropyridazin-3(2H)-one

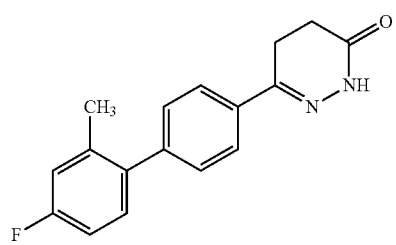 [SMILES: Cc1cc(F)ccc1-c1ccc(C2=NNC(=O)CC2)cc1]

In a reaction vessel 6-(4-chlorophenyl)-4,5-dihydropyridazin-3(2H)-one (135 mg, 647 µmol, CAS 1079-73-8), (4-fluoro-2-methylphenyl)boronic acid (149 mg, 971 µmol), potassium carbonate (179 mg, 1.29 mmol) and dicyclohexyl

[2',4',6'-tri(propan-2-yl)biphenyl-2-yl]phosphane (18.5 mg, 38.8 μmol) were suspended in 1,4-dioxane (930 μL) and water (310 μL). The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (15.3 mg, 19.4 μmol) was added. Again, nitrogen was passed through the reaction mixture which was stirred at 100° C. for 2 h in a heating block. The mixture was diluted with water and extracted with ethyl acetate three times. The combined organic layers were dried using a water-resistant filter and the filtrate was concentrated under reduced pressure. The residue was treated with 10 ml hexane (10 mL) and MTBE (1 mL) and stirred. The precipitate was filtered, washed with hexane and dried in vacuo to give 137 mg (95% purity, 71% yield) of the title compound.

LC-MS (Method 2): Rt=1.20 min; MS (ESIpos): m/z=283 [M+H]$^+$ $^1$H-NMR (400 MHz, DMSO-d$_6$) δ [ppm]: 2.247 (16.00), 2.447 (2.69), 2.467 (5.16), 2.523 (0.60), 2.969 (3.19), 2.990 (4.78), 3.010 (2.57), 5.758 (0.73), 6.543 (0.68), 7.074 (0.66), 7.080 (0.75), 7.095 (1.44), 7.101 (1.61), 7.117 (0.82), 7.124 (0.90), 7.165 (1.56), 7.172 (1.34), 7.191 (1.54), 7.198 (1.30), 7.234 (1.85), 7.249 (2.04), 7.255 (1.60), 7.270 (1.40), 7.377 (5.12), 7.398 (5.61), 7.802 (5.66), 7.823 (4.92), 10.966 (4.60).

Example 27

6-[3-Fluoro-4-(2-methylprop-1-en-1-yl)phenyl]-4,5-dihydropyridazin-3(2H)-one

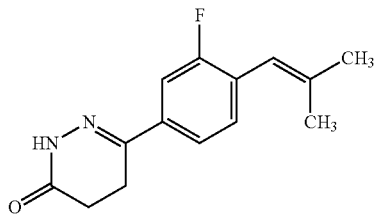 [SMILES: CC(C)=Cc1ccc(C2=NNC(=O)CC2)cc1F]

To 4,4,5,5-tetramethyl-2-(2-methylprop-1-en-1-yl)-1,3,2-dioxaborolane (54.6 mg, 300 μmol), a solution of 6-(4-chloro-3-fluorophenyl)-4,5-dihydropyridazin-3(2H)-one (34.3 mg, 150 μmol, Intermediate 9) in 1,4-dioxane (2.0 mL), dicyclohexyl[2',4',6'-tri(propan-2-yl)biphenyl-2-yl]phosphane (7.15 mg, 15.0 μmol), chloro(2-dicyclohexylphosphino-2',4',6'-triisopropyl-1,1'-biphenyl)[2-(2'-amino-1,1'-biphenyl)]palladium(II) (11.8 mg, 15.0 μmol) and an aqueous solution of potassium carbonate (330 μL, 0.90 M, 300 μmol) were added. The reaction mixture was heated for 16 h to 100° C. The samples were filtered over a pad of Alox N and purified by preparative HPLC to give 3.64 mg (10% yield) of the title compound.

LC-MS (MeTHOD AMC): Rt=1.11 min; MS (ESIpos): m/z=247 [M+H]$^+$

Example 28

6-[4-(2-aminopyridin-4-yl)-3-fluorophenyl]-4,5-dihydropyridazin-3(2H)-one

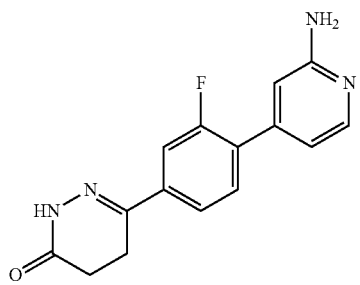 [SMILES: Nc1cc(-c2ccc(C3=NNC(=O)CC3)cc2F)ccn1]

Prepared in analogy to Example 27.

LC-MS (Method 1): Rt=0.47 min; MS (ESIpos): m/z=285 [M+H]$^+$

Example 29

6-{3-fluoro-4-[5-(trifluoromethyl)pyridin-3-yl]phenyl}-4,5-dihydropyridazin-3(2H)-one

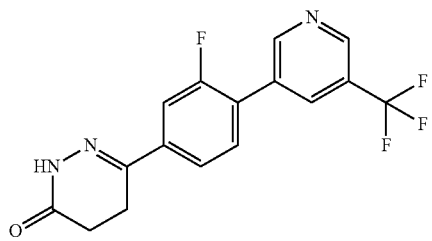 [SMILES: O=C1CCC(c2ccc(-c3cncc(C(F)(F)F)c3)c(F)c2)=NN1]

Prepared in analogy to Example 27.

LC-MS (Method 1): Rt=1.03 min; MS (ESIpos): m/z=338 [M+H]$^+$

Example 30

6-[3-fluoro-4-(pyridin-4-yl)phenyl]-4,5-dihydropyridazin-3(2H)-one

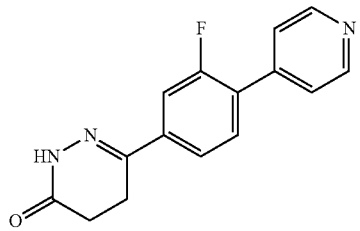 [SMILES: O=C1CCC(c2ccc(-c3ccncc3)c(F)c2)=NN1]

Prepared in analogy to Example 27.

LC-MS (Method 1): R$_t$=0.51 min; MS (ESIpos): m/z=270 [M+H]$^+$

Example 31

6-[3-fluoro-4-(2-methylpyrimidin-5-yl)phenyl]-4,5-dihydropyridazin-3(2H)-one

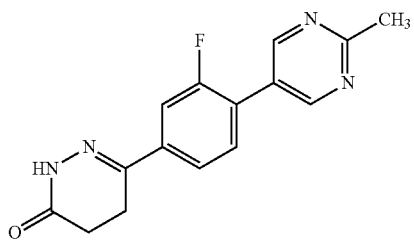 [SMILES: Cc1ncc(-c2ccc(C3=NNC(=O)CC3)cc2F)cn1]

Prepared in analogy to Example 27.
LC-MS (Method 1): $R_t$=0.73 min; MS (ESIpos): m/z=285 [M+H]$^+$

Example 32

6-[3-fluoro-4-(2-methoxypyridin-4-yl)phenyl]-4,5-dihydropyridazin-3(2H)-one

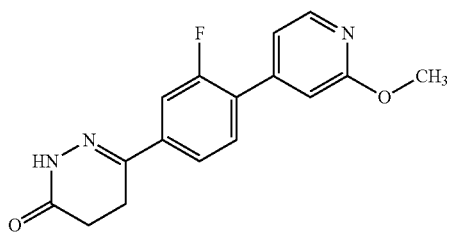 [SMILES: COc1cc(-c2ccc(C3=NNC(=O)CC3)cc2F)ccn1]

Prepared in analogy to Example 27.
LC-MS (Method 1): $R_t$=0.95 min; MS (ESIpos): m/z=300 [M+H]$^+$

Example 33

6-[3-fluoro-4-(2-methylpyridin-3-yl)phenyl]-4,5-dihydropyridazin-3(2H)-one

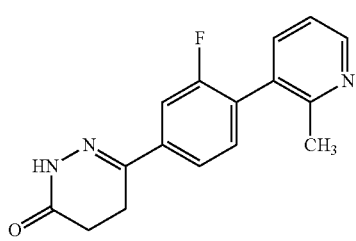 [SMILES: Cc1ncccc1-c1ccc(C2=NNC(=O)CC2)cc1F]

Prepared in analogy to Example 27.
LC-MS (Method 1): $R_t$=0.51 min; MS (ESIpos): m/z=284 [M+H]$^+$

Example 34

6-[3-fluoro-4-(6-methylpyridin-3-yl)phenyl]-4,5-dihydropyridazin-3(2H)-one

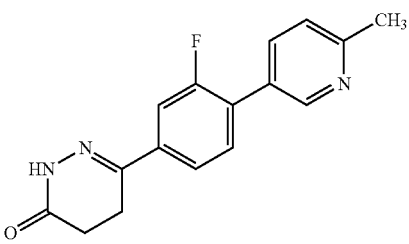 [SMILES: Cc1ccc(-c2ccc(C3=NNC(=O)CC3)cc2F)cn1]

Prepared in analogy to Example 27.
LC-MS (Method 1): $R_t$=0.56 min; MS (ESIpos): m/z=284 [M+H]$^+$

Example 35

6-(2-fluoro-3',4'-dimethyl[1,1'-biphenyl]-4-yl)-4,5-dihydropyridazin-3(2H)-one

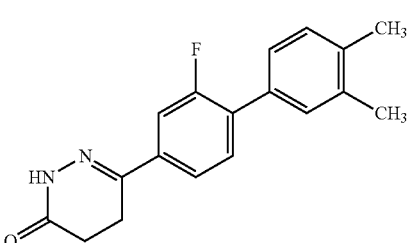

Prepared in analogy to Example 27.
LC-MS (Method 1): Rt=1.26 min; MS (ESIpos): m/z=297 [M+H]$^+$

Example 36

6-{4-[(2E)-but-2-en-2-yl]-3-fluorophenyl}-4,5-dihydropyridazin-3(2H)-one

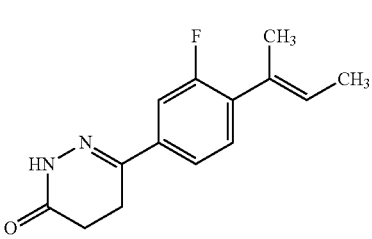 [SMILES: C/C=C(\C)c1ccc(C2=NNC(=O)CC2)cc1F]

Prepared in analogy to Example 27.
LC-MS (Method 1): $R_t$=1.12 min; MS (ESIpos): m/z=247 [M+H]$^+$

Example 37

6-(2,2'-difluoro-4'-methyl[1,1'-biphenyl]-4-yl)-4,5-dihydropyridazin-3(2H)-one

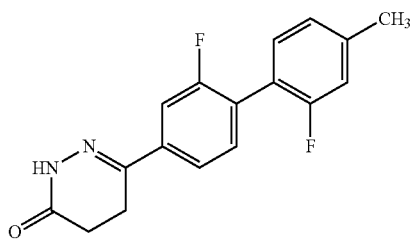 [SMILES: Cc1ccc(-c2ccc(C3=NNC(=O)CC3)cc2F)c(F)c1]

Prepared in analogy to Example 27.
LC-MS (Method 1): $R_t$=1.17 min; MS (ESIpos): m/z=301 [M+H]$^+$

Example 38

6-(2,2',4',5'-tetrafluoro[1,1'-biphenyl]-4-yl)-4,5-dihydropyridazin-3(2H)-one

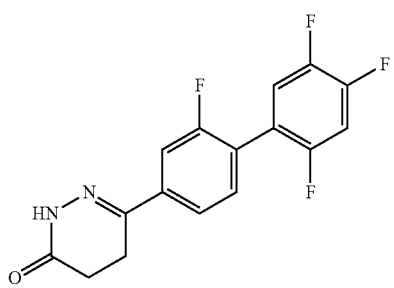 [SMILES: O=C1CCC(c2ccc(-c3cc(F)c(F)cc3F)c(F)c2)=NN1]

Prepared in analogy to Example 27.
LC-MS (Method 1): $R_t$=1.14 min; MS (ESIpos): m/z=323 [M+H]$^+$

Example 39

6-(2,2',3',4'-tetrafluoro[1,1'-biphenyl]-4-yl)-4,5-dihydropyridazin-3(2H)-one

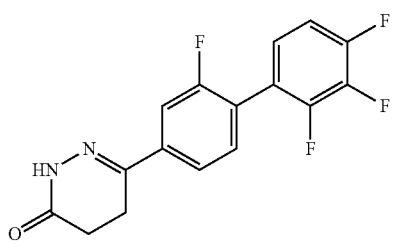 [SMILES: O=C1CCC(c2ccc(-c3ccc(F)c(F)c3F)c(F)c2)=NN1]

Prepared in analogy to Example 27.
LC-MS (Method 1): Rt=1.15 min; MS (ESIpos): m/z=323 [M+H]$^+$

Example 40

6-[3-fluoro-4-(pyrimidin-5-yl)phenyl]-4,5-dihydropyridazin-3(2H)-one

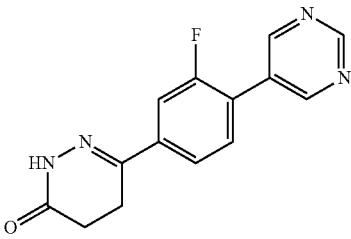 [SMILES: O=C1CCC(c2ccc(-c3cncnc3)c(F)c2)=NN1]

Prepared in analogy to Example 27.
LC-MS (Method 1): $R_t$=0.68 min; MS (ESIpos): m/z=271 [M+H]$^+$

Example 41

6-(2-fluoro-2',5'-dimethoxy[1,1'-biphenyl]-4-yl)-4,5-dihydropyridazin-3(2H)-one

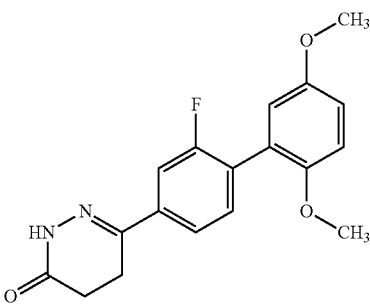 [SMILES: COc1ccc(OC)c(-c2ccc(C3=NNC(=O)CC3)cc2F)c1]

Prepared in analogy to Example 27.
LC-MS (Method 1): $R_t$=1.05 min; MS (ESIpos): m/z=329 [M+H]$^+$

Example 42

6-(2,2',5'-trifluoro[1,1'-biphenyl]-4-yl)-4,5-dihydropyridazin-3(2H)-one

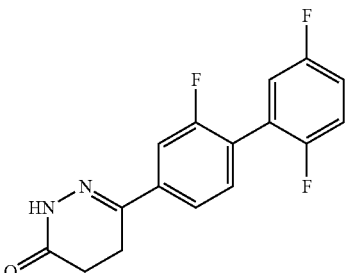

Prepared in analogy to Example 27.
LC-MS (Method 1): Rt=1.09 min; MS (ESIpos): m/z=305 [M+H]$^+$

Example 43

6-(2'-amino-2,5'-difluoro[1,1'-biphenyl]-4-yl)-4,5-dihydropyridazin-3(2H)-one

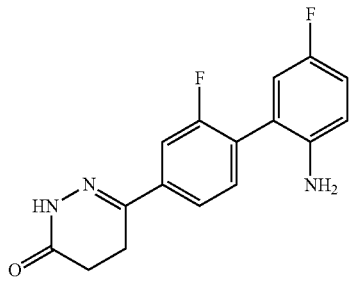 [SMILES: Nc1ccc(F)cc1-c1ccc(C2=NNC(=O)CC2)cc1F]

Prepared in analogy to Example 27.
LC-MS (Method 1): $R_t$=0.91 min; MS (ESIpos): m/z=302 [M+H]$^+$

Example 44

6-[2-fluoro-2'-(trifluoromethoxy)[1,1'-biphenyl]-4-yl]-4,5-dihydropyridazin-3(2H)-one

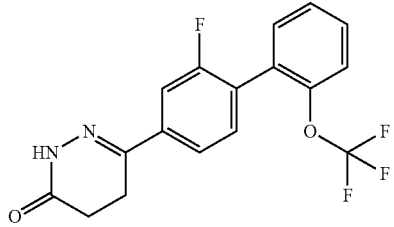 [SMILES: O=C1CCC(c2ccc(-c3ccccc3OC(F)(F)F)c(F)c2)=NN1]

Prepared in analogy to Example 27.
LC-MS (Method 1): $R_t$=1.19 min; MS (ESIpos): m/z=353 [M+H]$^+$

Example 45

6-[3-fluoro-4-(furan-3-yl)phenyl]-4,5-dihydropyridazin-3(2H)-one

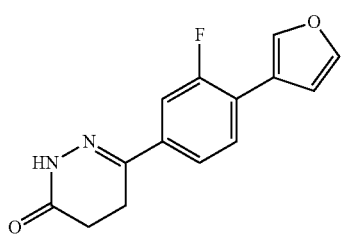 [SMILES: O=C1CCC(c2ccc(-c3ccoc3)c(F)c2)=NN1]

Prepared in analogy to Example 27.
LC-MS (Method 1): $R_t$=0.99 min; MS (ESIpos): m/z=259 [M+H]$^+$

Example 46

2'-fluoro-4'-(6-oxo-1,4,5,6-tetrahydropyridazin-3-yl)[1,1'-biphenyl]-4-carbonitrile

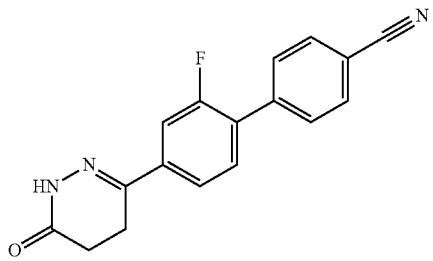 [SMILES: N#Cc1ccc(-c2ccc(C3=NNC(=O)CC3)cc2F)cc1]

Prepared in analogy to Example 27.
LC-MS (Method 1): $R_t$=0.99 min; MS (ESIpos): m/z=294 [M+H]$^+$

Example 47

2'-fluoro-4'-(6-oxo-1,4,5,6-tetrahydropyridazin-3-yl)[1,1'-biphenyl]-3-carbonitrile

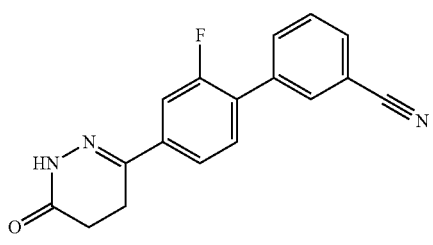 [SMILES: N#Cc1cccc(-c2ccc(C3=NNC(=O)CC3)cc2F)c1]

Prepared in analogy to Example 27.
LC-MS (Method 1): $R_t$=1.00 min; MS (ESIpos): m/z=294 [M+H]$^+$

Example 48

6-(3'-amino-2-fluoro-4'-methyl[1,1'-biphenyl]-4-yl)-4,5-dihydropyridazin-3(2H)-one

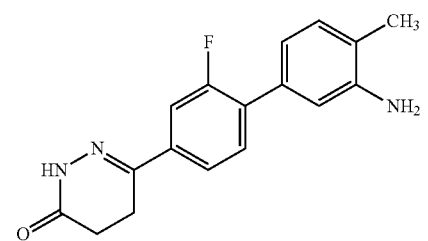 [SMILES: Cc1ccc(-c2ccc(C3=NNC(=O)CC3)cc2F)cc1N]

Prepared in analogy to Example 27.
LC-MS (Method 1): $R_t$=0.87 min; MS (ESIpos): m/z=298 [M+H]$^+$

Example 49

6-(2-fluoro-3'-hydroxy[1,1'-biphenyl]-4-yl)-4,5-di-hydropyridazin-3(2H)-one

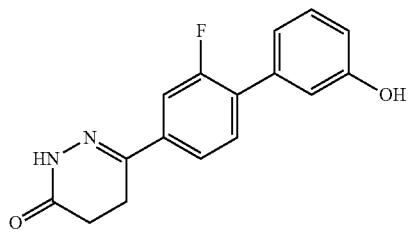 [SMILES: O=C1CCC(c2ccc(-c3cccc(O)c3)c(F)c2)=NN1]

Prepared in analogy to Example 27.
LC-MS (Method 1): $R_t$=0.87 min; MS (ESIpos): m/z=285 [M+H]$^+$

Example 50

6-(2-fluoro-2'-hydroxy[1,1'-biphenyl]-4-yl)-4,5-di-hydropyridazin-3(2H)-one

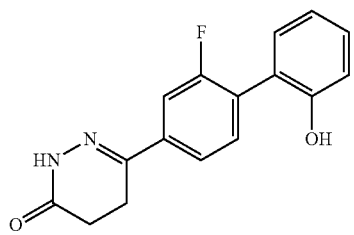 [SMILES: O=C1CCC(c2ccc(-c3ccccc3O)c(F)c2)=NN1]

Prepared in analogy to Example 27.
LC-MS (Method 1): $R_t$=0.90 min; MS (ESIpos): m/z=285 [M+H]$^+$

Example 51

6-(2,3',4'-trifluoro[1,1'-biphenyl]-4-yl)-4,5-dihydro-pyridazin-3(2H)-one

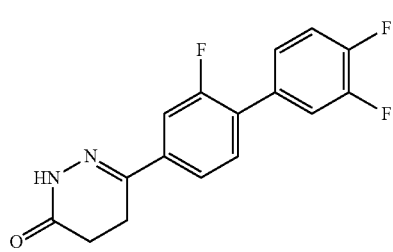 [SMILES: O=C1CCC(c2ccc(-c3ccc(F)c(F)c3)c(F)c2)=NN1]

Prepared in analogy to Example 27.
LC-MS (Method 1): $R_t$=1.15 min; MS (ESIpos): m/z=305 [M+H]$^+$

Example 52

6-(2'-ethoxy-2-fluoro[1,1'-biphenyl]-4-yl)-4,5-dihy-dropyridazin-3(2H)-one

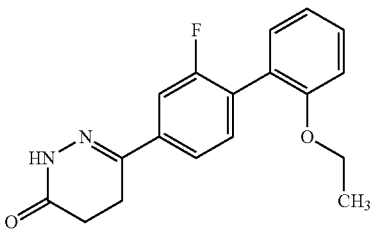 [SMILES: CCOc1ccccc1-c1ccc(C2=NNC(=O)CC2)cc1F]

Prepared in analogy to Example 27.
LC-MS (Method 1): $R_t$=1.15 min; MS (ESIpos): m/z=313 [M+H]$^+$

Example 53

6-(2,2',3'-trifluoro[1,1'-biphenyl]-4-yl)-4,5-dihydro-pyridazin-3(2H)-one

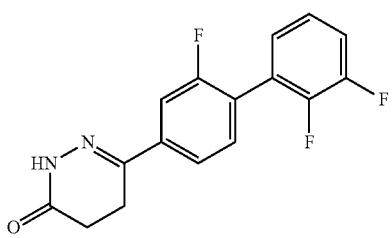 [SMILES: O=C1CCC(c2ccc(-c3cccc(F)c3F)c(F)c2)=NN1]

Prepared in analogy to Example 27.
LC-MS (Method 1): $R_t$=1.11 min; MS (ESIpos): m/z=305 [M+H]$^+$

Example 54

6-(2,3',5'-trifluoro[1,1'-biphenyl]-4-yl)-4,5-dihydro-pyridazin-3(2H)-one

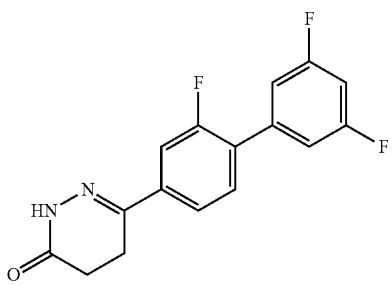 [SMILES: O=C1CCC(c2ccc(-c3cc(F)cc(F)c3)c(F)c2)=NN1]

Prepared in analogy to Example 27.
LC-MS (Method 1): $R_t$=1.16 min; MS (ESIpos): m/z=305 [M+H]$^+$ Example 55

6-(2,2',4'-trifluoro[1,1'-biphenyl]-4-yl)-4,5-dihydro-pyridazin-3(2H)-one

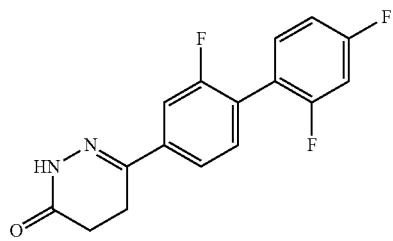 [SMILES: O=C1CCC(c2ccc(-c3ccc(F)cc3F)c(F)c2)=NN1]

Prepared in analogy to Example 27.
LC-MS (Method 1): $R_t$=1.12 min; MS (ESIpos): m/z=305 [M+H]$^+$ Example 56

6-(2-fluoro-2',4'-dimethyl[1,1'-biphenyl]-4-yl)-4,5-dihydropyridazin-3(2H)-one

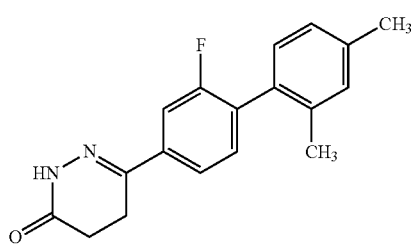

Prepared in analogy to Example 27.
LC-MS (Method 1): $R_t$=1.24 min; MS (ESIpos): m/z=297 [M+H]$^+$ Example 57

6-(2,5'-difluoro-2'-methyl[1,1'-biphenyl]-4-yl)-4,5-dihydropyridazin-3(2H)-one

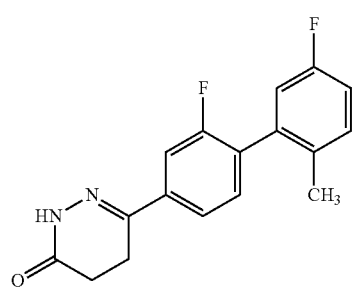 [SMILES: Cc1ccc(F)cc1-c1ccc(C2=NNC(=O)CC2)cc1F]

Prepared in analogy to Example 27.
LC-MS (Method 1): $R_t$=1.17 min; MS (ESIpos): m/z=301 [M+H]$^+$ Example 58

6-(2,3'-difluoro-4'-methyl[1,1'-biphenyl]-4-yl)-4,5-dihydropyridazin-3(2H)-one

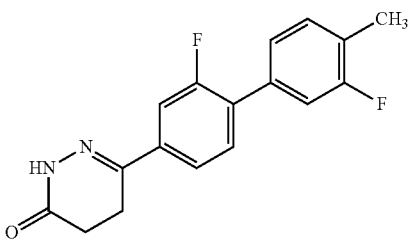 [SMILES: Cc1ccc(-c2ccc(C3=NNC(=O)CC3)cc2F)cc1F]

Prepared in analogy to Example 27.
LC-MS (Method 1): $R_t$=1.22 min; MS (ESIpos): m/z=301 [M+H]$^+$ Example 60

6-(2,2'-difluoro[1,1'-biphenyl]-4-yl)-4,5-dihydro-pyridazin-3(2H)-one

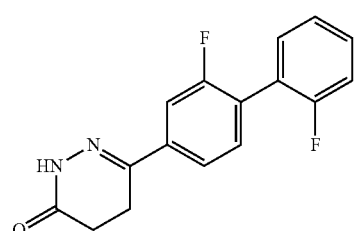

Prepared in analogy to Example 27.
LC-MS (Method 1): $R_t$=1.08 min; MS (ESIpos): m/z=287 [M+H]$^+$ Example 61

6-[2-fluoro-2'-(trifluoromethyl)[1,1'-biphenyl]-4-yl]-4,5-dihydropyridazin-3(2H)-one

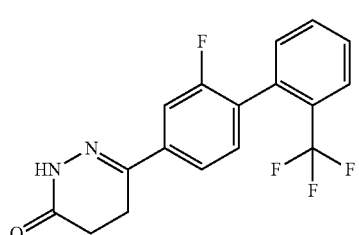

Prepared in analogy to Example 27.
LC-MS (Method 1): $R_t$=1.16 min; MS (ESIpos): m/z=336 [M+H]$^+$

Example 62

6-(2-fluoro-2'-methoxy[1,1'-biphenyl]-4-yl)-4,5-dihydropyridazin-3(2H)-one

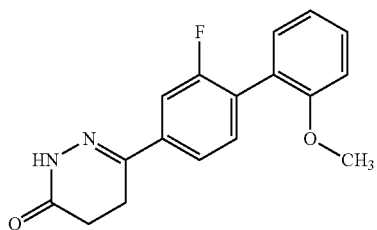 [SMILES: COc1ccccc1-c1ccc(C2=NNC(=O)CC2)cc1F]

Prepared in analogy to Example 27.
LC-MS (Method 1): $R_t$=1.07 min; MS (ESIpos): m/z=299 [M+H]$^+$

Example 63

6-(2,3'-difluoro[1,1'-biphenyl]-4-yl)-4,5-dihydropyridazin-3(2H)-one

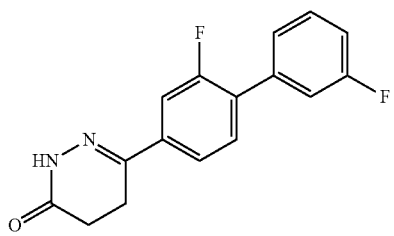 [SMILES: O=C1CCC(c2ccc(-c3cccc(F)c3)c(F)c2)=NN1]

Prepared in analogy to Example 27.
LC-MS (Method 1): $R_t$=1.12 min; MS (ESIpos): m/z=287 [M+H]$^+$

Example 64

6-(2-fluoro-3'-methoxy[1,1'-biphenyl]-4-yl)-4,5-dihydropyridazin-3(2H)-one

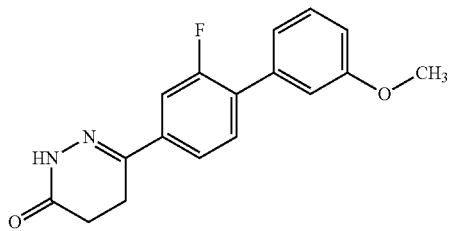 [SMILES: COc1cccc(-c2ccc(C3=NNC(=O)CC3)cc2F)c1]

Prepared in analogy to Example 27.
LC-MS (Method 1): $R_t$=1.09 min; MS (ESIpos): m/z=299 [M+H]$^+$

Example 65

6-(3'-amino-2-fluoro[1,1'-biphenyl]-4-yl)-4,5-dihydropyridazin-3(2H)-one

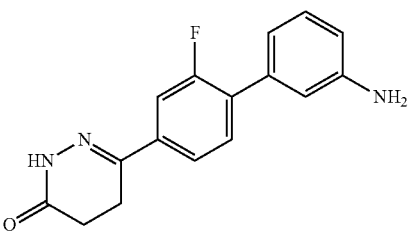 [SMILES: Nc1cccc(-c2ccc(C3=NNC(=O)CC3)cc2F)c1]

Prepared in analogy to Example 27.
LC-MS (Method 1): $R_t$=0.73 min; MS (ESIpos): m/z=284 [M+H]$^+$

Example 66

6-(2'-amino-2-fluoro[1,1'-biphenyl]-4-yl)-4,5-dihydropyridazin-3(2H)-one

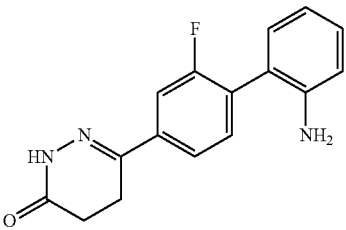

Prepared in analogy to Example 27.
LC-MS (Method 1): $R_t$=0.90 min; MS (ESIpos): m/z=284 [M+H]$^+$

Example 67

6-[3-fluoro-4-(4-methylpyridin-3-yl)phenyl]-4,5-dihydropyridazin-3(2H)-one

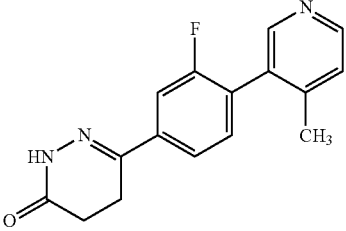 [SMILES: Cc1ccncc1-c1ccc(C2=NNC(=O)CC2)cc1F]

Prepared in analogy to Example 27.
LC-MS (Method 1): Rt=0.56 min; MS (ESIpos): m/z=284 [M+H]$^+$

Example 68

6-(2,2'-difluoro-5'-methyl[1,1'-biphenyl]-4-yl)-4,5-dihydropyridazin-3(2H)-one

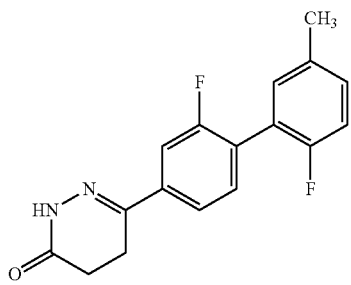 [SMILES: Cc1ccc(F)c(-c2ccc(C3=NNC(=O)CC3)cc2F)c1]

Prepared in analogy to Example 27.
LC-MS (Method 1): R$_t$=1.17 min; MS (ESIpos): m/z=301 [M+H]$^+$

Example 69

6-[4-(3-chloropyridin-4-yl)-3-fluorophenyl]-4,5-dihydropyridazin-3(2H)-one

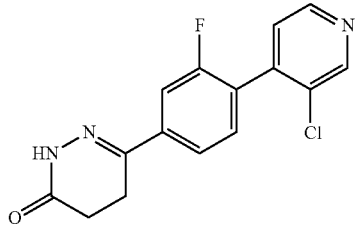 [SMILES: O=C1CCC(c2ccc(-c3ccncc3Cl)c(F)c2)=NN1]

Prepared in analogy to Example 27.
LC-MS (Method 1): Rt=0.89 min; MS (ESIpos): m/z=304 [M+H]$^+$

Example 70

6-[3-fluoro-4-(2-methoxypyridin-3-yl)phenyl]-4,5-dihydropyridazin-3(2H)-one

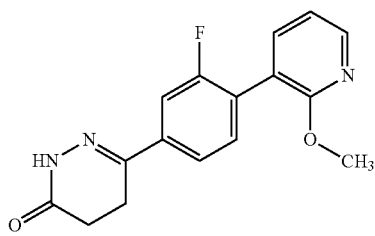 [SMILES: COc1ncccc1-c1ccc(C2=NNC(=O)CC2)cc1F]

Prepared in analogy to Example 27.
LC-MS (Method 1): R$_t$=0.96 min; MS (ESIpos): m/z=300 [M+H]$^+$

Example 71

6-[3-fluoro-4-(6-fluoropyridin-3-yl)phenyl]-4,5-dihydropyridazin-3(2H)-one

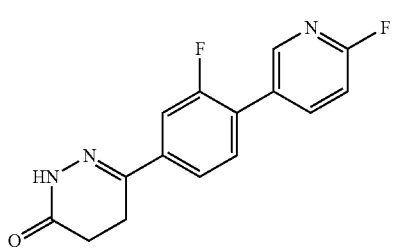 [SMILES: O=C1CCC(c2ccc(-c3ccc(F)nc3)c(F)c2)=NN1]

Prepared in analogy to Example 27.
LC-MS (Method 1): Rt=0.92 min; MS (ESIpos): m/z=288 [M+H]$^+$

Example 72

6-[3-fluoro-4-(2-fluoropyridin-3-yl)phenyl]-4,5-dihydropyridazin-3(2H)-one

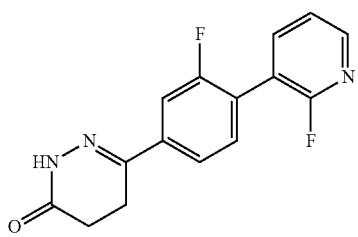 [SMILES: O=C1CCC(c2ccc(-c3cccnc3F)c(F)c2)=NN1]

Prepared in analogy to Example 27.
LC-MS (Method 1): R$_t$=0.88 min; MS (ESIpos): m/z=288 [M+H]$^+$

Example 73

6-[3-fluoro-4-(3-methylpyridin-4-yl)phenyl]-4,5-dihydropyridazin-3(2H)-one

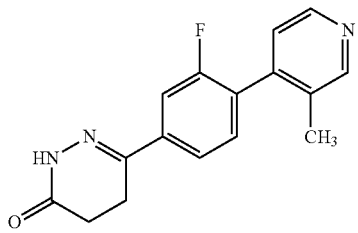 [SMILES: Cc1cnccc1-c1ccc(C2=NNC(=O)CC2)cc1F]

Prepared in analogy to Example 27.
LC-MS (Method 1): R$_t$=0.54 min; MS (ESIpos): m/z=284 [M+H]$^+$

Example 74

6-[3-fluoro-4-(1H-indol-6-yl)phenyl]-4,5-dihydropyridazin-3(2H)-one

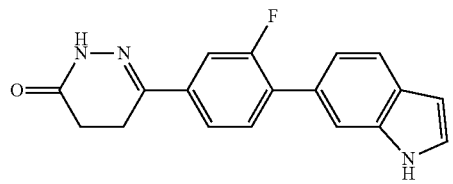 [SMILES: O=C1CCC(c2ccc(-c3ccc4cc[nH]c4c3)c(F)c2)=NN1]

Prepared in analogy to Example 27.

LC-MS (Method 1): $R_t$=1.04 min; MS (ESIpos): m/z=308 [M+H]$^+$

Example 75

6-[3-fluoro-4-(1H-indol-4-yl)phenyl]-4,5-dihydropyridazin-3(2H)-one

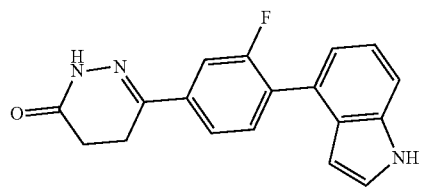 [SMILES: O=C1CCC(c2ccc(-c3cccc4[nH]ccc34)c(F)c2)=NN1]

Prepared in analogy to Example 27.

LC-MS (Method 1): $R_t$=0.95 min; MS (ESIpos): m/z=308 [M+H]$^+$

Example 76

6-(4'-amino-2-fluoro[1,1'-biphenyl]-4-yl)-4,5-dihydropyridazin-3(2H)-one

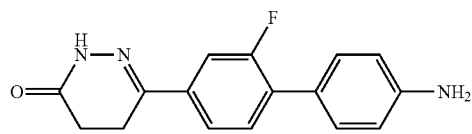

Prepared in analogy to Example 27.

LC-MS (Method 1): $R_t$=0.72 min; MS (ESIpos): m/z=284 [M+H]$^+$

Example 77

6-(2-fluoro-2'-methyl[1,1'-biphenyl]-4-yl)-4,5-dihydropyridazin-3(2H)-one

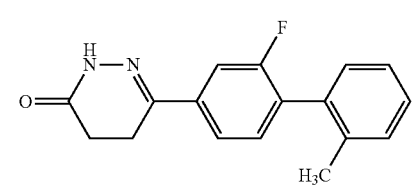 [SMILES: Cc1ccccc1-c1ccc(C2=NNC(=O)CC2)cc1F]

Prepared in analogy to Example 27.

LC-MS (Method 1): $R_t$=1.16 min; MS (ESIpos): m/z=283 [M+H]$^+$

Example 78

6-(2-fluoro-2',3'-dimethoxy[1,1'-biphenyl]-4-yl)-4,5-dihydropyridazin-3(2H)-one

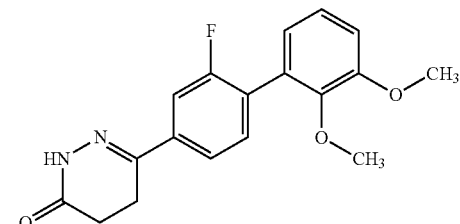

Prepared in analogy to Example 27.

LC-MS (Method 1): $R_t$=1.04 min; MS (ESIpos): m/z=329 [M+H]$^+$

Example 79

6-(2-fluoro-2',3',4',5'-tetrahydro[1,1'-biphenyl]-4-yl)-4,5-dihydropyridazin-3(2H)-one

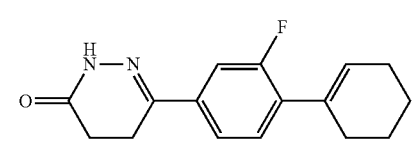 [SMILES: O=C1CCC(c2ccc(C3=CCCCC3)c(F)c2)=NN1]

Prepared in analogy to Example 27.

LC-MS (Method 1): $R_t$=1.25 min; MS (ESIpos): m/z=273 [M+H]$^+$

Example 80

6-[4-(cyclopent-1-en-1-yl)-3-fluorophenyl]-4,5-dihydropyridazin-3(2H)-one

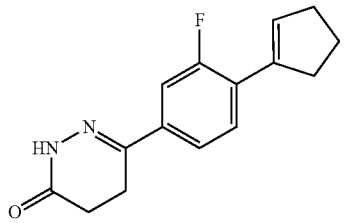 [SMILES: O=C1CCC(c2ccc(C3=CCCC3)c(F)c2)=NN1]

Prepared in analogy to Example 27.
LC-MS (Method 1): $R_t$=1.20 min; MS (ESIpos): m/z=259 [M+H]$^+$

Example 81

6-(2'-ethyl-2-fluoro[1,1'-biphenyl]-4-yl)-4,5-dihydropyridazin-3(2H)-one

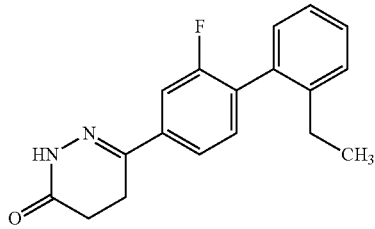 [SMILES: CCc1ccccc1-c1ccc(C2=NNC(=O)CC2)cc1F]

Prepared in analogy to Example 27.
LC-MS (Method 1): $R_t$=1.22 min; MS (ESIpos): m/z=297 [M+H]$^+$

Example 82

6-[3-fluoro-4-(6-methoxypyridin-3-yl)phenyl]-4,5-dihydropyridazin-3(2H)-one

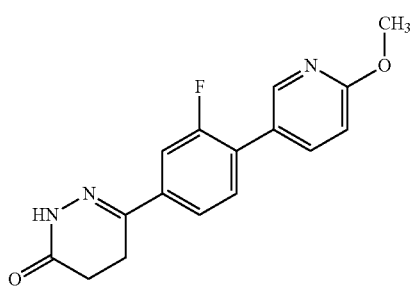 [SMILES: COc1ccc(-c2ccc(C3=NNC(=O)CC3)cc2F)cn1]

Prepared in analogy to Example 27.
LC-MS (Method 1): Rt=0.98 min; MS (ESIpos): m/z=300 [M+H]$^+$

Example 83

6-(3'-chloro-2,4'-difluoro[1,1'-biphenyl]-4-yl)-4,5-dihydropyridazin-3(2H)-one

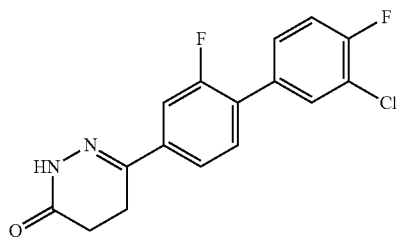 [SMILES: O=C1CCC(c2ccc(-c3ccc(F)c(Cl)c3)c(F)c2)=NN1]

LC-MS (Method 1): $R_t$=1.22 min; MS (ESIpos): m/z=321 [M+H]$^+$

Example 84

6-(2,4'-difluoro-3'-methyl[1,1'-biphenyl]-4-yl)-4,5-dihydropyridazin-3(2H)-one

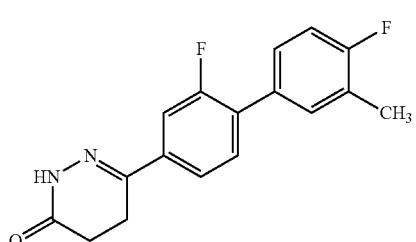

Prepared in analogy to Example 27.
LC-MS (Method 1): $R_t$=1.21 min; MS (ESIpos): m/z=301 [M+H]$^+$

Example 85

6-(2-fluoro-2',3'-dimethyl[1,1'-biphenyl]-4-yl)-4,5-dihydropyridazin-3(2H)-one

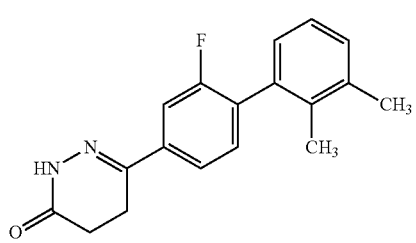 [SMILES: Cc1cccc(-c2ccc(C3=NNC(=O)CC3)cc2F)c1C]

Prepared in analogy to Example 27.
LC-MS (Method 1): $R_t$=1.22 min; MS (ESIpos): m/z=297 [M+H]$^+$

Example 86

6-(2-fluoro-4'-methoxy[1,1'-biphenyl]-4-yl)-4,5-dihydropyridazin-3(2H)-one

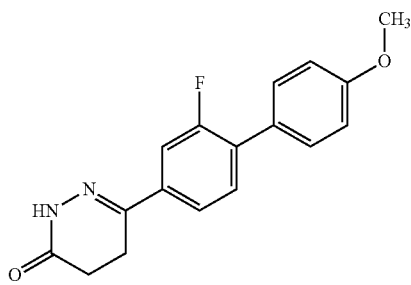 [SMILES: COc1ccc(-c2ccc(C3=NNC(=O)CC3)cc2F)cc1]

Prepared in analogy to Example 27.
LC-MS (Method 1): $R_t$=1.08 min; MS (ESIpos): m/z=299 [M+H]$^+$

Example 87

6-(2-fluoro-4'-methyl[1,1'-biphenyl]-4-yl)-4,5-dihydropyridazin-3(2H)-one

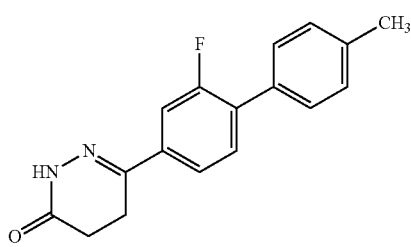 [SMILES: Cc1ccc(-c2ccc(C3=NNC(=O)CC3)cc2F)cc1]

Prepared in analogy to Example 27.
LC-MS (Method 1): $R_t$=1.19 min; MS (ESIpos): m/z=283 [M+H]$^+$

Example 88

6-(2-fluoro-2',5'-dimethyl[1,1'-biphenyl]-4-yl)-4,5-dihydropyridazin-3(2H)-one

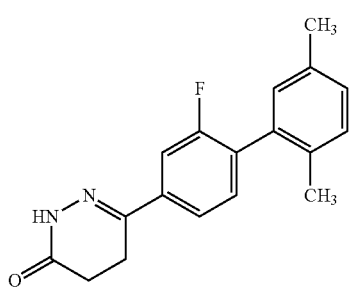 [SMILES: Cc1ccc(C)c(-c2ccc(C3=NNC(=O)CC3)cc2F)c1]

Prepared in analogy to Example 27.
LC-MS (Method 1): $R_t$=1.24 min; MS (ESIpos): m/z=297 [M+H]$^+$

Example 89

2',6-difluoro-4'-(6-oxo-1,4,5,6-tetrahydropyridazin-3-yl)[1,1'-biphenyl]-3-carbonitrile

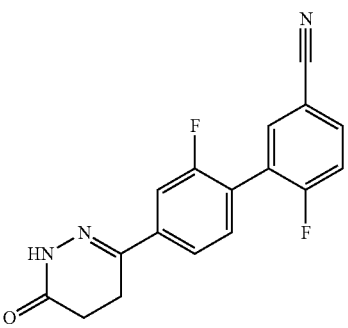 [SMILES: N#Cc1ccc(F)c(-c2ccc(C3=NNC(=O)CC3)cc2F)c1]

Prepared in analogy to Example 27.
LC-MS (Method 1): $R_t$=0.99 min; MS (ESIpos): m/z=312 [M+H]$^+$

Example 90

6-[4-(2-aminopyridin-4-yl)-3-methylphenyl]-4,5-dihydropyridazin-3(2H)-one

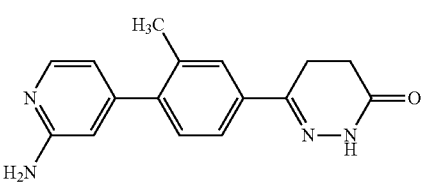 [SMILES: Cc1cc(C2=NNC(=O)CC2)ccc1-c1ccnc(N)c1]

Prepared in analogy to Example 27.
LC-MS (Method 1): $R_t$=0.51 min; MS (ESIpos): m/z=281 [M+H]$^+$

Example 91

6-[4-(2-aminopyrimidin-5-yl)-3-methylphenyl]-4,5-dihydropyridazin-3(2H)-one

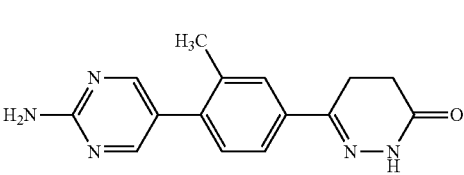 [SMILES: Cc1ncc(-c2ccc(C3=NNC(=O)CC3)cc2C)cn1]

Prepared in analogy to Example 27.
LC-MS (Method 1): $R_t$=0.63 min; MS (ESIpos): m/z=282 [M+H]$^+$

Example 92

6-[3-methyl-4-(2-methylpyrimidin-5-yl)phenyl]-4,5-dihydropyridazin-3(2H)-one

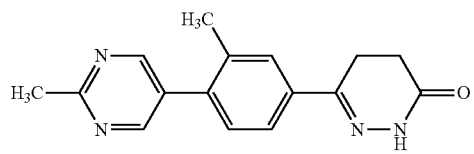

Prepared in analogy to Example 27.
LC-MS (Method 1): $R_t$=0.77 min; MS (ESIpos): m/z=281 [M+H]$^+$

Example 93

6-[3-methyl-4-(6-methylpyridin-3-yl)phenyl]-4,5-dihydropyridazin-3(2H)-one

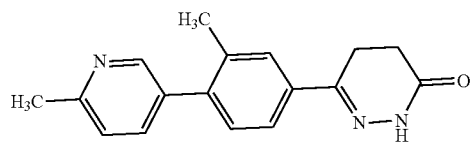 [SMILES: Cc1ccc(-c2ccc(C3=NNC(=O)CC3)cc2C)cn1]

Prepared in analogy to Example 27.
LC-MS (Method 1): $R_t$=0.57 min; MS (ESIpos): m/z=280 [M+H]$^+$

Example 94

6-(2'-fluoro-2,4'-dimethyl[1,1'-biphenyl]-4-yl)-4,5-dihydropyridazin-3(2H)-one

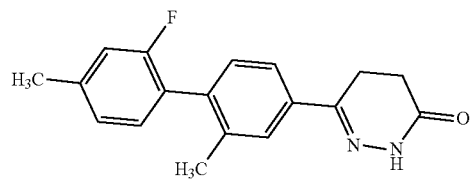 [SMILES: Cc1ccc(-c2ccc(C3=NNC(=O)CC3)cc2C)c(F)c1]

Prepared in analogy to Example 27.
LC-MS (Method 1): Rt=1.24 min; MS (ESIpos): m/z=297 [M+H]$^+$

Example 95

6-(2',4',5'-trifluoro-2-methyl[1,1'-biphenyl]-4-yl)-4,5-dihydropyridazin-3(2H)-one

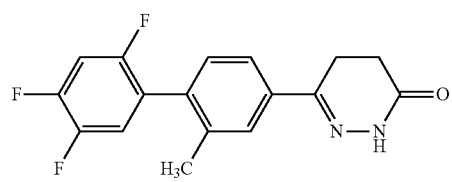 [SMILES: Cc1cc(C2=NNC(=O)CC2)ccc1-c1cc(F)c(F)cc1F]

Prepared in analogy to Example 27.
LC-MS (Method 1): Rt=1.20 min; MS (ESIpos): m/z=319 [M+H]$^+$

Example 96

6-(3',4',5'-trifluoro-2-methyl[1,1'-biphenyl]-4-yl)-4,5-dihydropyridazin-3(2H)-one

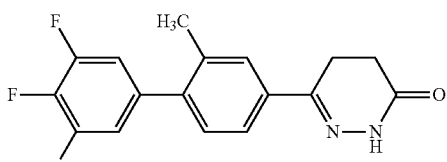

Prepared in analogy to Example 27.
LC-MS (Method 1): $R_t$=1.25 min; MS (ESIpos): m/z=319 [M+H]$^+$

Example 97

6-(2',3',4'-trifluoro-2-methyl[1,1'-biphenyl]-4-yl)-4,5-dihydropyridazin-3(2H)-one

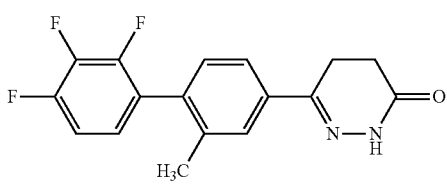 [SMILES: Cc1cc(C2=NNC(=O)CC2)ccc1-c1ccc(F)c(F)c1F]

Prepared in analogy to Example 27.
LC-MS (Method 1): $R_t$=1.21 min; MS (ESIpos): m/z=319 [M+H]$^+$

Example 98

6-(2',5'-difluoro-2-methyl[1,1'-biphenyl]-4-yl)-4,5-dihydropyridazin-3(2H)-one

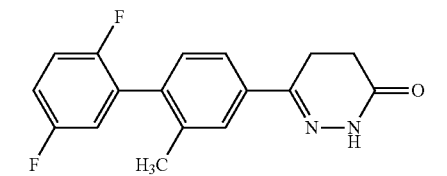

Prepared in analogy to Example 27.
LC-MS (Method 1): Rt=1.16 min; MS (ESIpos): m/z=301 [M+H]$^+$

Example 99

2'-methyl-4'-(6-oxo-1,4,5,6-tetrahydropyridazin-3-yl)[1,1'-biphenyl]-2-carbonitrile

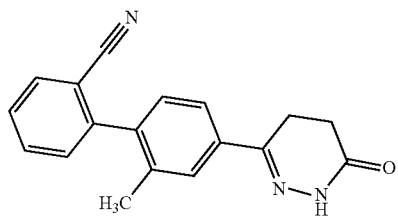 [SMILES: Cc1cc(C2=NNC(=O)CC2)ccc1-c1ccccc1C#N]

Prepared in analogy to Example 27.

LC-MS (Method 1): $R_t=1.02$ min; MS (ESIpos): m/z=290 [M+H]$^+$

Example 100

2'-methyl-4'-(6-oxo-1,4,5,6-tetrahydropyridazin-3-yl)[1,1'-biphenyl]-4-carbonitrile

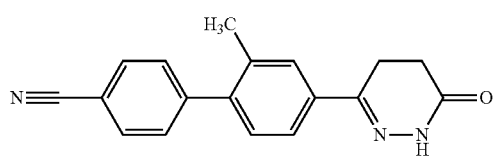 [SMILES: Cc1cc(C2=NNC(=O)CC2)ccc1-c1ccc(C#N)cc1]

Prepared in analogy to Example 27.

LC-MS (Method 1): $R_t=1.04$ min; MS (ESIpos): m/z=290 [M+H]$^+$

Example 101

6-(3'-hydroxy-2-methyl[1,1'-biphenyl]-4-yl)-4,5-dihydropyridazin-3(2H)-one

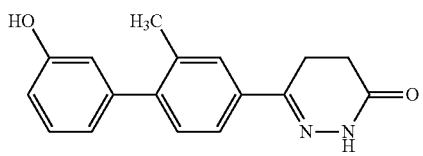

Prepared in analogy to Example 27.

LC-MS (Method 1): $R_t=0.92$ min; MS (ESIpos): m/z=281 [M+H]$^+$

Example 102

6-(2'-hydroxy-2-methyl[1,1'-biphenyl]-4-yl)-4,5-dihydropyridazin-3(2H)-one

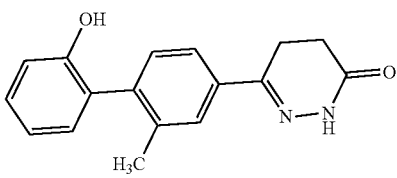 [SMILES: Cc1cc(C2=NNC(=O)CC2)ccc1-c1ccccc1O]

Prepared in analogy to Example 27.

LC-MS (Method 1): $R_t=0.97$ min; MS (ESIpos): m/z=281 [M+H]$^+$

Example 103

6-(3'-amino-2-methyl[1,1'-biphenyl]-4-yl)-4,5-dihydropyridazin-3(2H)-one

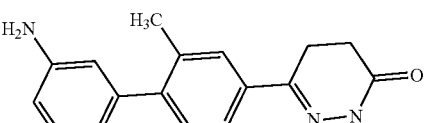

Prepared in analogy to Example 27.

LC-MS (Method 1): $R_t=0.76$ min; MS (ESIpos): m/z=280 [M+H]$^+$

Example 104

6-(2',3'-difluoro-2-methyl[1,1'-biphenyl]-4-yl)-4,5-dihydropyridazin-3(2H)-one

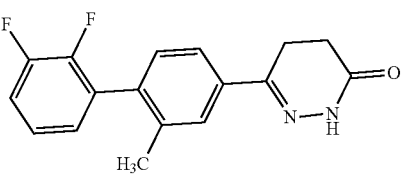

Prepared in analogy to Example 27.

LC-MS (Method 1): $R_t=1.17$ min; MS (ESIpos): m/z=301 [M+H]$^+$

Example 105

6-(3',5'-difluoro-2-methyl[1,1'-biphenyl]-4-yl)-4,5-dihydropyridazin-3(2H)-one

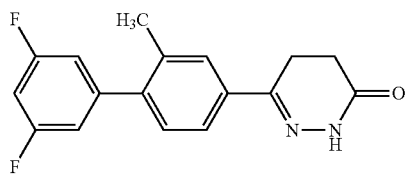

Prepared in analogy to Example 27.
LC-MS (Method 1): $R_t$=1.21 min; MS (ESIpos): m/z=301 [M+H]$^+$

Example 106

6-(2',4'-difluoro-2-methyl[1,1'-biphenyl]-4-yl)-4,5-dihydropyridazin-3(2H)-one

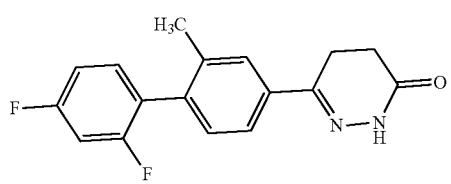 [SMILES: Cc1cc(C2=NNC(=O)CC2)ccc1-c1ccc(F)cc1F]

Prepared in analogy to Example 27.
LC-MS (Method 1): $R_t$=1.18 min; MS (ESIpos): m/z=301 [M+H]$^+$

Example 107

6-(3'-fluoro-2,4'-dimethyl[1,1'-biphenyl]-4-yl)-4,5-dihydropyridazin-3(2H)-one

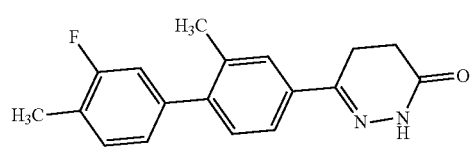 [SMILES: Cc1ccc(-c2ccc(C3=NNC(=O)CC3)cc2C)cc1F]

Prepared in analogy to Example 27.
LC-MS (Method 1): $R_t$=1.27 min; MS (ESIpos): m/z=297 [M+H]$^+$

Example 108

6-(3'-amino-4'-chloro-2-methyl[1,1'-biphenyl]-4-yl)-4,5-dihydropyridazin-3(2H)-one

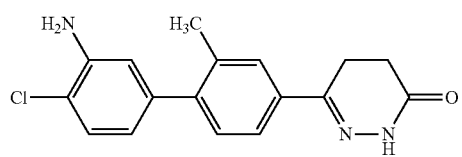 [SMILES: Cc1cc(C2=NNC(=O)CC2)ccc1-c1ccc(Cl)c(N)c1]

Prepared in analogy to Example 27.
LC-MS (Method 1): $R_t$=1.10 min; MS (ESIpos): m/z=314 [M+H]$^+$

Example 109

6-(2'-fluoro-2-methyl[1,1'-biphenyl]-4-yl)-4,5-dihydropyridazin-3(2H)-one

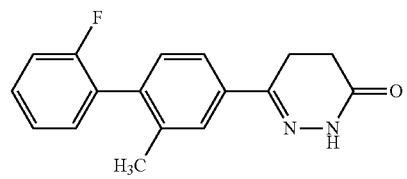 [SMILES: Cc1cc(C2=NNC(=O)CC2)ccc1-c1ccccc1F]

Prepared in analogy to Example 27.
LC-MS (Method 1): $R_t$=1.15 min; MS (ESIpos): m/z=283 [M+H]$^+$

Example 110

6-(2',6'-difluoro-2-methyl[1,1'-biphenyl]-4-yl)-4,5-dihydropyridazin-3(2H)-one

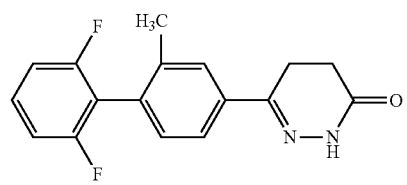 [SMILES: Cc1cc(C2=NNC(=O)CC2)ccc1-c1c(F)cccc1F]

Prepared in analogy to Example 27.
LC-MS (Method 1): $R_t$=1.13 min; MS (ESIpos): m/z=301 [M+H]$^+$

Example 111

6-(2'-methoxy-2-methyl[1,1'-biphenyl]-4-yl)-4,5-dihydropyridazin-3(2H)-one

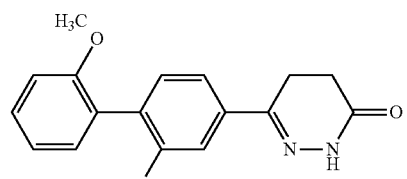

Prepared in analogy to Example 27.
LC-MS (Method 1): $R_t$=1.14 min; MS (ESIpos): m/z=295 [M+H]$^+$

Example 112

6-(3'-fluoro-2-methyl[1,1'-biphenyl]-4-yl)-4,5-dihydropyridazin-3(2H)-one

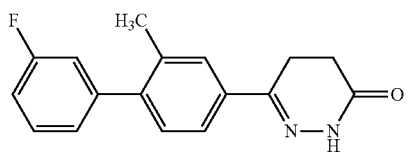

Prepared in analogy to Example 27.
LC-MS (Method 1): R$_t$=1.18 min; MS (ESIpos): m/z=283 [M+H]$^+$

Example 113

6-(3'-methoxy-2-methyl[1,1'-biphenyl]-4-yl)-4,5-dihydropyridazin-3(2H)-one

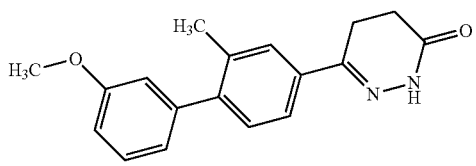 [SMILES: COc1cccc(-c2ccc(C3=NNC(=O)CC3)cc2C)c1]

Prepared in analogy to Example 27.
LC-MS (Method 1): R$_t$=1.15 min; MS (ESIpos): m/z=295 [M+H]$^+$

Example 114

2'-methyl-4'-(6-oxo-1,4,5,6-tetrahydropyridazin-3-yl)[1,1'-biphenyl]-3-carboxamide

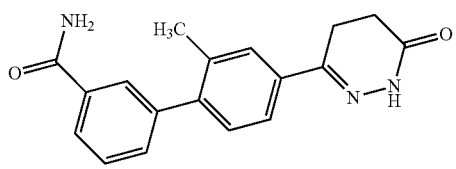 [SMILES: Cc1cc(C2=NNC(=O)CC2)ccc1-c1cccc(C(N)=O)c1]

Prepared in analogy to Example 27.
LC-MS (Method 1): R$_t$=0.80 min; MS (ESIpos): m/z=308 [M+H]$^+$

Example 115

6-(4'-amino-2-methyl[1,1'-biphenyl]-4-yl)-4,5-dihydropyridazin-3(2H)-one

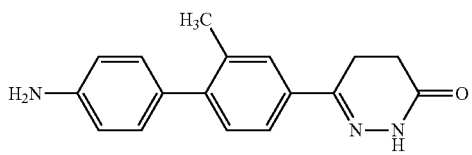 [SMILES: Cc1cc(C2=NNC(=O)CC2)ccc1-c1ccc(N)cc1]

Prepared in analogy to Example 27.
LC-MS (Method 1): R$_t$=0.71 min; MS (ESIpos): m/z=280 [M+H]$^+$

Example 116

6-(2,2'-dimethyl[1,1'-biphenyl]-4-yl)-4,5-dihydropyridazin-3(2H)-one

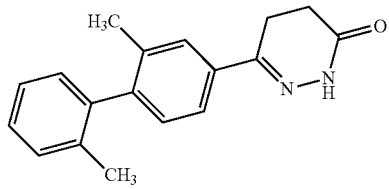 [SMILES: Cc1ccccc1-c1ccc(C2=NNC(=O)CC2)cc1C]

Prepared in analogy to Example 27.
LC-MS (Method 1): R$_t$=1.23 min; MS (ESIpos): m/z=279 [M+H]$^+$

Example 117

6-(2'-ethyl-2-methyl[1,1'-biphenyl]-4-yl)-4,5-dihydropyridazin-3(2H)-one

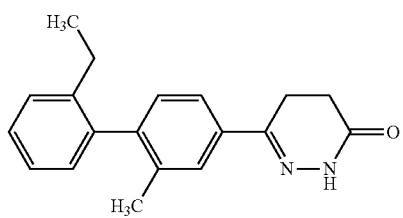 [SMILES: CCc1ccccc1-c1ccc(C2=NNC(=O)CC2)cc1C]

Prepared in analogy to Example 27.
LC-MS (Method 1): R$_t$=1.30 min; MS (ESIpos): m/z=293 [M+H]$^+$

Example 118

6-[4-(6-methoxypyridin-3-yl)-3-methylphenyl]-4,5-dihydropyridazin-3(2H)-one

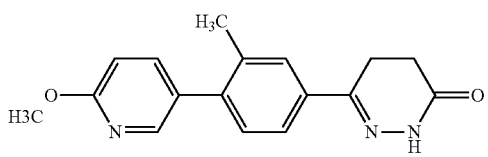

Prepared in analogy to Example 27.
LC-MS (Method 1): R$_t$=1.02 min; MS (ESIpos): m/z=296 [M+H]$^+$

Example 119

6-(4'-fluoro-2,3'-dimethyl[1,1'-biphenyl]-4-yl)-4,5-dihydropyridazin-3(2H)-one

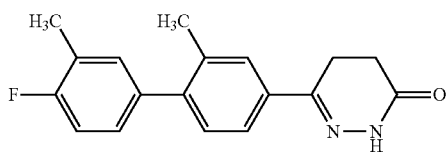 [SMILES: Cc1cc(-c2ccc(C3=NNC(=O)CC3)cc2C)ccc1F]

Prepared in analogy to Example 27.
LC-MS (Method 1): R$_t$=1.26 min; MS (ESIpos): m/z=297 [M+H]$^+$

Example 120

6-(2,3'-dimethyl[1,1'-biphenyl]-4-yl)-4,5-dihydropyridazin-3(2H)-one

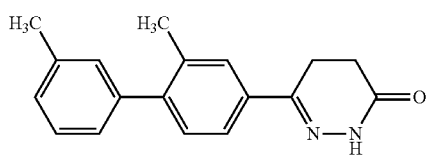 [SMILES: Cc1cccc(-c2ccc(C3=NNC(=O)CC3)cc2C)c1]

Prepared in analogy to Example 27.
LC-MS (Method 1): R$_t$=1.25 min; MS (ESIpos): m/z=279 [M+H]$^+$

Example 121

6-(2,4'-dimethyl[1,1'-biphenyl]-4-yl)-4,5-dihydropyridazin-3(2H)-one

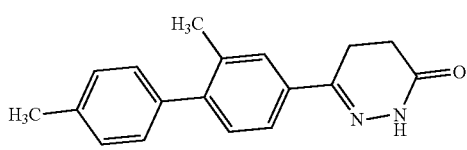 [SMILES: Cc1ccc(-c2ccc(C3=NNC(=O)CC3)cc2C)cc1]

Prepared in analogy to Example 27.
LC-MS (Method 1): Rt=1.25 min; MS (ESIpos): m/z=279 [M+H]$^+$

Example 122

6-(4'-chloro-2-methyl[1,1'-biphenyl]-4-yl)-4,5-dihydropyridazin-3(2H)-one

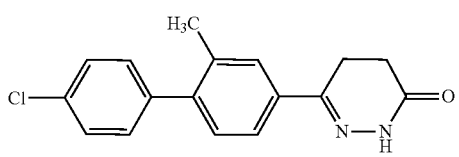 [SMILES: Cc1cc(C2=NNC(=O)CC2)ccc1-c1ccc(Cl)cc1]

Prepared in analogy to Example 27.
LC-MS (Method 1): R$_t$=1.28 min; MS (ESIpos): m/z=299 [M+H]$^+$

Example 123

6-[4-(morpholin-4-yl)phenyl]-4,5-dihydropyridazin-3(2H)-one

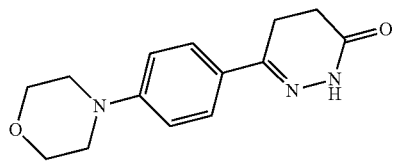 [SMILES: O=C1CCC(c2ccc(N3CCOCC3)cc2)=NN1]

To 558 mg of methyl 4-(4-morpholinophenyl)-4-oxobutanoate (2.01 mmol, Intermediate 2) in 6 mL of EtOH was added 645 mg (20.1 mmol) of hydrazine and the reaction mixture was heated at 100° C. for 3 h. The reaction mixture was cooled on an ice bath producing white crystals which were filtered and rinsed with cold EtOH yielding 414 mg of product (79%).

$^1$H NMR (400 MHz, DMSO-d$_6$) δ 10.75 (s, 1H), 7.63 (d, J=9.0 Hz, 2H), 6.96 (d, J=9.0 Hz, 2H), 3.82-3.67 (m, 4H), 3.24-3.09 (m, 4H), 2.88 (t, J=8.2 Hz, 2H), 2.40 (t, J=8.2 Hz, 2H).
$^{13}$C NMR (101 MHz, DMSO) δ 167.41, 152.03, 149.86, 127.11, 126.66, 114.62, 66.42, 48.13, 26.60, 22.15. Mass 260 (M+1)+.

Example 124

6-[3,5-dichloro-4-(morpholin-4-yl)phenyl]-4,5-dihydropyridazin-3(2H)-one

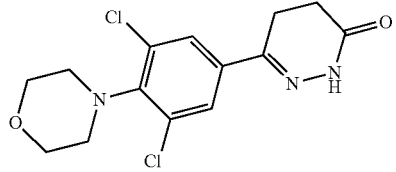 [SMILES: O=C1CCC(c2cc(Cl)c(N3CCOCC3)c(Cl)c2)=NN1]

A solution of 145 mg of 6-(4-morpholinophenyl)-4,5-dihydropyridazin-3(2H)-one (0.56 mmol, Example 123) in 3 mL HOAc was cooled to 10-15° C. before addition of 0.75 mL of 10-15% NaOCl solution. After 30 min another 0.75 mL of 10-15% NaOCl solution was added. After 1 h, the reaction mixture was transferred to a separatory funnel, CH$_2$Cl$_2$ and water were added, the water was rinsed with CH$_2$Cl$_2$ three times, the combined CH$_2$Cl$_2$ was rinsed with NaHSO$_3$ (aq), 1 N HCl and NaHCO$_3$ (aq) before drying and concentrating. Chromatography with 30-60% EtOAc in hexane isolated 35 mg of product which was then recrystallized from MeOH (19%).

$^1$H NMR (300 MHz, CDCl$_3$) δ 8.65 (s, 1H), 7.64 (s, 2H), 3.89-3.79 (m, 4H), 3.30-3.20 (m, 4H), 2.93 (t, J=8.3 Hz, 2H), 2.61 (t, J=8.2 Hz, 2H). Mass 328 (M+1)+.

Also isolated was the mono-chlorinated compound which was recrystallized from MeOH. $^1$H NMR (300 MHz, CDCl$_3$) δ 8.53 (s, 1H), 7.77 (d, J=2.1 Hz, 1H), 7.58 (dd, J=8.5, 2.2 Hz, 1H), 7.04 (d, J=8.5 Hz, 1H), 3.96-3.84 (m, 4H), 3.17-3.07 (m, 4H), 2.95 (t, J=8.2 Hz, 2H), 2.61 (t, J=8.2 Hz, 2H). Mass 294 (M+1)+.

Example 125

6-(3,4-Dichlorophenyl)-4,5-dihydropyridazin-3(2H)-one

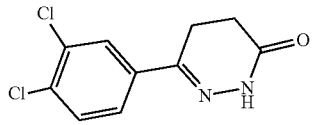 [SMILES: O=C1CCC(c2ccc(Cl)c(Cl)c2)=NN1]

To 218 mg of ethyl 4-(3,4-dichlorophenyl)-4-oxobutanoate (0.792 mmol; Intermediate 3) dissolved in 10 mL EtOH was added 254 mg of hydrazine (7.92 mmol) and the reaction mixture was heated at reflux temperature for 6 h. After cooling, water and $CH_2Cl_2$ were added, the organic layer was separated, the water rinsed again with $CH_2Cl_2$. The combined $CH_2Cl_2$ was dried and chromatographed with 10-50% EtOAc in hexane yielding 95 mg of product (49%) which was recrystallized from MeOH.

$^1$H NMR (400 MHz, CD$_3$OD) δ 7.96 (s, 1H), 7.71 (d, J=8.4 Hz, 1H), 7.57 (d, J=8.5 Hz, 1H), 3.01 (t, J=8.3 Hz, 2H), 2.59 (t, J=8.3 Hz, 2H). $^{13}$C NMR (101 MHz, CD$_3$OD) δ 168.41, 148.59, 136.25, 132.93, 132.25, 130.23, 127.46, 125.30, 25.46, 21.62. Mass 243 (M+1)+.

Example 126

6-[4-(Morpholin-4-yl)-3-(trifluoromethyl)phenyl]-4,5-dihydropyridazin-3(2H)-one

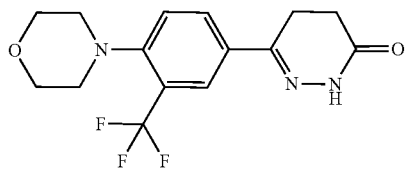 [SMILES: O=C1CCC(c2ccc(N3CCOCC3)c(C(F)(F)F)c2)=NN1]

4-[4-(Morpholin-4-yl)-3-(trifluoromethyl)phenyl]-4-oxobutanoic acid (163 mg, 492 μmol; Intermediate 34) was diluted with hydrazine hydrate (1:1) (240 μL, 4.9 mmol) and this solution was heated at 100° C. overnight. After cooling to room temperature under stirring the reaction mixture was poured into water and extracted with ethyl acetate three times. Solvents were removed in vacuo. The crude material was purified by preparative HPLC (Method 5) to give 26.0 mg (95% purity, 15% yield) of the title compound.

LC-MS (Method 1): Rt=1.03 min; MS (ESIpos): m/z=328 [M+H]$^+$ $^1$H-NMR (400 MHz, DMSO-d$_6$) δ [ppm]: 2.318 (0.72), 2.432 (8.34), 2.452 (15.75), 2.473 (10.99), 2.518 (10.27), 2.523 (7.12), 2.539 (0.63), 2.660 (0.72), 2.881 (13.09), 2.893 (16.00), 2.904 (14.06), 2.950 (10.44), 2.971 (15.75), 2.991 (8.51), 3.699 (14.06), 3.711 (15.45), 3.722 (14.15), 7.578 (6.65), 7.599 (7.37), 7.963 (4.13), 7.969 (5.05), 7.984 (3.41), 7.989 (4.88), 8.009 (10.57), 8.015 (8.17), 8.957 (0.59), 10.991 (13.52).

Example 127

6-{4-[1-(difluoromethyl)-1H-pyrazol-4-yl]-3-(trifluoromethyl)phenyl}-4,5-dihydropyridazin-3(2H)-one

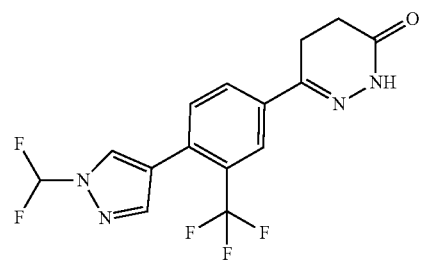 [SMILES: O=C1CCC(c2ccc(-c3cnn(C(F)F)c3)c(C(F)(F)F)c2)=NN1]

A sealable pressure tube containing 6-[4-bromo-3-(trifluoromethyl)phenyl]-4,5-dihydropyridazin-3(2H)-one (Intermediate 38, 75 mg, 0.21 mmol), 1-(difluoromethyl)-4-(4,4,5,5-tetramethyl-1,3,2-dioxaborolan-2-yl)-1H-pyrazole (66.7 mg, 0.27 mmol), K2CO3 (1.2M aqueous, 0.53 mL, 0.63 mmol) and [1,1'-bis(di-tert-butylphosphino)ferrocene]dichloropalladium(II) [Pd-118] (13.7 mg, 0.02 mmol) in 1,4-dioxane (2.8 mL) was degassed via nitrogen-filled balloon for 5 minutes. After this time, the vessel was sealed and was heated at 80° C. for 2 h. After this time, the reaction mixture was partitioned between EtOAc and saturated aqueous sodium hydrogen carbonate solution, with the organic layer isolated, washed with saturated aqueous sodium chloride solution, dried (MgSO4), filtered and concentrated in vacuo. The residual material was purified by Biotage Isolera™ chromatography (10 g KP-Sil, eluting with heptanes-EtOAc, 0:1 to 1:0) with the desired fractions combined, concentrated in vacuo and subsequently lyopholised to afford the title compound (70 mg 93%) of the title compound as an off-white solid LCMS (Method 3, 2 min) 99% @ Rt=1.07 min, MS (ESIpos): m/z=358.85 (M+H)+. LCMS (Method 3, 7 min) 100% @ Rt=3.70 min, MS (ESIpos): m/z=358.90 (M+H)+. 1H NMR (250 MHz, DMSO-d6) δ=2.47 (s, 2H), 3.04 (t, J=8.3 Hz, 2H), 7.67 (d, J=8.1 Hz, 1H), 7.89 (t, J=58.9 Hz, 1H), 7.94-8.10 (m, 2H), 8.17 (d, J=1.6 Hz, 1H), 8.47 (s, 1H), 11.08 (s, 1H).

LC-MS (Method 3): Rt=3.70 min; MS (ESIpos): m/z=359 [M+H]$^+$

Example 128

6-[4'-fluoro-2-(trifluoromethyl)[1,1'-biphenyl]-4-yl]-4,5-dihydropyridazin-3(2H)-one

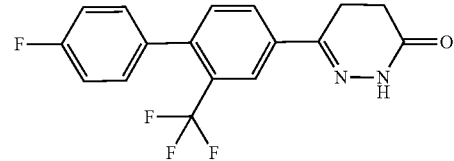 [SMILES: O=C1CCC(c2ccc(-c3ccc(F)cc3)c(C(F)(F)F)c2)=NN1]

Synthesized analogously to Example from Intermediate 38 and (4-fluorophenyl)boronic acid LCMS (Method 3, 2 min) 100% @ Rt=1.19 min, MS (ESIpos): m/z=336.85 (M+H)+.

LCMS (Method 3, 2 min) 100% @ Rt=4.17 min, MS (ESIpos): m/z=336.85 (M+H)+. 1H NMR (250 MHz, DMSO-d6) δ=2.47-2.55 (m, 2H), 3.05 (t, J=8.3 Hz, 2H), 7.22-7.46 (m, 4H), 7.49 (d, J=8.1 Hz, 1H), 8.04 (dd, J=8.1, 1.4 Hz, 1H), 8.16 (d, J=1.6 Hz, 1H), 11.08 (s, 1H).

LC-MS (Method 3): $R_f$=4.17 min; MS (ESIpos): m/z=337 $[M+H]^+$

Example 129

6-{4-[(2-methoxyethyl)amino]-3-(trifluoromethyl) phenyl}-4,5-dihydropyridazin-3(2H)-one

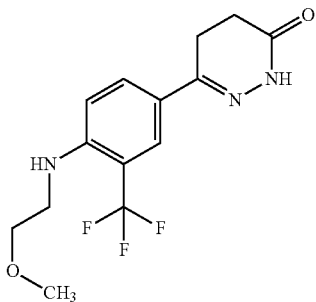 [SMILES: COCCNc1ccc(C2=NNC(=O)CC2)cc1C(F)(F)F]

6-[4-fluoro-3-(trifluoromethyl)phenyl]-4,5-dihydropyridazin-3(2H)-one (Intermediate 39, 50 mg, 0.19 mmol), 2-methoxyethanamine (16 mg, 0.21 mmol) and N,N-diisopropylethylamine (0.1 mL, 0.57 mmol) were dissolved in DMSO (1 mL) and the resulting mixture was heated at 120° C. overnight. Crude NMR showed 20% conversion to the desired product. More 2-methoxyethanamine (57 mg, 0.77 mmol) was added and the mixture was heated at 120° C. for a further 24 hours. Complete reaction was observed by crude NMR. The mixture was diluted with EtOAc (50 mL) and washed with 1M aq. HCl (25 mL), brine (2×25 mL), dried (Na2SO4), filtered and concentrated at reduced pressure. The residue was purified via Biotage Isolera chromatography (using a gradient of eluents, 9:1 heptane:EtOAc to 100% EtOAc). The residue obtained was recrystallised (heptane/EtOAc) giving the desired product (24 mg, 39% yield) as a white solid. 1H NMR (500 MHz, DMSO-d6) δ 10.76 (s, 1H), 7.85-7.73 (m, 2H), 6.92 (d, J=8.6 Hz, 1H), 5.58 (t, J=5.3 Hz, 1H), 3.55-3.49 (m, 2H), 3.43-3.36 (m, 2H), 3.28 (s, 3H), 2.92-2.85 (m, 2H), 2.43-2.37 (m, 2H). LCMS (Method 4, 7 min) Rt=2.59 mins, MS (ESIPos): m/z=316.1 (M+H)+

LC-MS (Method 3): Rt=2.59 min; MS (ESIpos): m/z=316 $[M+H]^+$

Example 130

6-[4-{[3,3,3-trifluoro-2-hydroxypropyl]amino}-3-(trifluoromethyl)phenyl]-4,5-dihydropyridazin-3(2H)-one (racemic)

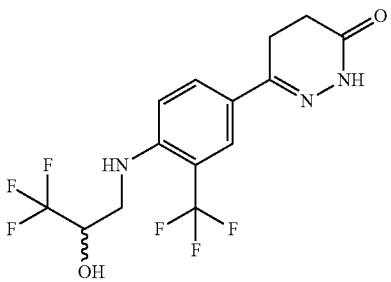 [SMILES: O=C1CCC(c2ccc(NCC(O)C(F)(F)F)c(C(F)(F)F)c2)=NN1]

Synthesized analogously to Example 129 from Intermediate 39 and 3-amino-1,1,1-trifluoropropan-2-ol.

1H NMR (500 MHz, DMSO-d6) δ 10.78 (s, 1H), 7.87-7.76 (m, 2H), 6.96 (d, J=8.7 Hz, 1H), 6.61 (d, J=6.4 Hz, 1H), 5.76-5.63 (m, 1H), 4.33-4.17 (m, 1H), 3.64-3.51 (m, 1H), 3.46-3.33 (m, 1H), 2.89 (t, J=8.2 Hz, 2H), 2.41 (t, J=8.2 Hz, 2H). LCMS (Method 4, 7 min) Rt=2.61 mins, MS (ESIPos): m/z=370.1 (M+H)+LC-MS (Method 3): $R_t$=2.61 min; MS (ESIpos): m/z=370 $[M+H]^+$

Example 131

6-{3-fluoro-4-[3-(trifluoromethyl)-1H-pyrazol-1-yl] phenyl}-4,5-dihydropyridazin-3(2H)-one

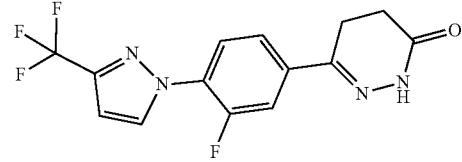 [SMILES: O=C1CCC(c2ccc(-n3ccc(C(F)(F)F)n3)c(F)c2)=NN1]

A solution of 300 mg of 6-(3,4-difluorophenyl)-4,5-dihydropyridazin-3(2H)-one (1.42 mmol, Intermediate 41) and 966 mg of 3-trifluoromethyl pyrazole (7.10 mmol) in 3 mL of DMF was heated at 80° C. for 1 h, 100° C. for 3 h, and then 80° C. for 3 h. After cooling, water was added and rinsed several times with $CH_2Cl_2$, the combined $CH_2Cl_2$ layers were dried ($MgSO_4$) and concentrated. Little of the material was very soluble in $CH_2Cl_2$, solids were filtered off and chromatography could not separate the product from starting material. All the materials were combined, slurried in methanol, heated briefly and let sit for several days. Filtration produced cleaner material. Recrystallization from $CH_2Cl_2$ produced impure product, the filtrate was concentrated and recrystallized from methanol to give 9.1 mg of white needles (2%). $^1$H NMR (400 MHz, DMSO-$d_6$) δ 11.10 (s, 1H), 8.50 (s, 1H), 7.89 (d, J=8.2 Hz, 1H), 7.84 (d, J=13.6 Hz, 1H), 7.78 (d, J=8.5 Hz, 1H), 7.09 (s, 1H), 3.01 (t, J=8.2 Hz, 2H), 2.49 (t, J=8.4 Hz, 2H). $^{19}$F NMR (376 MHz, DMSO-$d_6$) δ−60.66, −124.13. Mass 327 (M+1).

Experimental Section—Biological Assays

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Example I

Cell Proliferation Measurement

The antiproliferative activity of the compounds of the general formula (I) was examined in vitro in human cancer cells. For this purpose, 1000 cells (or 500 HeLa cells) were plated in 384-well plates with appropriate growth medium and incubated at 37° C. overnight. After 24 h, the cells on the test plate were treated with the compounds of the general formula (I) as and incubated at 37° C. for 72 h. The compounds were added to the cells by means of an HP D300 digital dispenser in a 10 (or more)-step dilution series. As control, the cells were treated with vehicle (DMSO at 0.3% final concentration). After 72 h, the cells were treated with 20 µl/well of 50% CTG solution in PBS (Promega Cell Titer Glo (catalogue #G755B and G756B)) and incubated at room temperature for 10 min, and luminescence was measured by means of a VICTOR V (Perkin Elmer), in order to determine cell viability at the end of treatment. The percentage effect on cell growth and the $IC_{50}$ derived therefrom were determined for each test substance using the values from untreated wells (=percent viability). The $IC_{50}$ values were calculated using a 4-parameter fit.

Table 4

Anti-proliferation $IC_{50}$ values of several examples in vitro in different cell lines

| Example Compound | IC50 (M) | | | | |
|---|---|---|---|---|---|
| | HeLa (Cervical cancer) | SK-MEL-3 (melanoma) | IGR-37 (melanoma) | NCI-H1734 | H4 |
| 1 | 3.09E−8 | >1.00E−7 | | | |
| 2 | 5.72E−9 | 1.45E−8 | | | |
| 3 | 4.59E−9 | 8.42E−9 | | 2.77E−8 | 3.66E−8 |
| 4 | 1.25E−8 | 2.28E−8 | | | |
| 5 | 2.13E−8 | 6.57E−8 | | | |
| 6 | 5.33E−8 | 8.93E−8 | | | |
| 7 | 5.56E−8 | >1.00E−7 | | | |
| 8 | 1.27E−9 | 5.01E−9 | | | |
| 9 | 1.55E−9 | 2.12E−9 | | | |
| 10 | 3.18E−8 | 4.02E−8 | | | |
| 11 | 4.14E−8 | 7.03E−8 | | | |
| 12 | 5.48E−9 | 1.14E−8 | | | |
| 13 | 5.59E−9 | 1.38E−8 | | 3.20E−8 | 4.11E−8 |
| 14 | 2.16E−9 | 5.84E−9 | | 1.88E−8 | 3.09E−8 |
| 15 | 4.48E−8 | 6.95E−8 | | | |
| 16 | 4.86E−9 | 9.80E−9 | | | |
| 17 | 1.29E−9 | 2.99E−9 | | | |
| 18 | 5.39E−9 | 1.05E−8 | | | |
| 19 | 5.76E−9 | 1.04E−8 | | | |
| 20 | 3.35E−8 | 4.77E−8 | | | |
| 21 | 2.87E−9 | 5.82E−9 | | | |
| 22 | 5.20E−9 | 7.18E−7 | 8.82E−9 | | |
| 23 | 5.80E−8 | 6.76E−8 | | | |
| 24 | 9.97E−9 | 1.50E−8 | | | |
| 25 | 6.19E−9 | 1.99E−8 | | | |
| 26 | 2.02E−9 | 3.60E−9 | | | |
| 27 | 3.36E−9 | 6.10E−9 | | | |
| 28 | 6.02E−8 | >1.00E−7 | | | |
| 29 | 8.64E−8 | >1.00E−7 | | | |
| 30 | 9.66E−9 | 1.42E−8 | | | |
| 31 | 3.44E−8 | 4.73E−8 | | | |
| 32 | 5.99E−8 | 6.47E−8 | | | |
| 33 | 1.44E−8 | 2.48E−8 | | | |
| 34 | 7.23E−9 | 9.88E−9 | | | |
| 35 | 6.36E−8 | >1.00E−7 | | | |
| 36 | 8.33E−9 | 1.43E−8 | | | |
| 37 | 4.00E−9 | 7.31E−9 | | | |
| 38 | 5.59E−9 | 1.11E−8 | | | |
| 39 | 5.25E−9 | 8.40E−9 | | | |
| 40 | 3.75E−8 | 4.76E−8 | | | |
| 41 | 5.16E−8 | 6.88E−8 | | | |
| 42 | 5.23E−9 | 8.40E−9 | | | |
| 43 | 1.53E−8 | 2.63E−8 | | | |
| 44 | 1.79E−8 | 3.45E−8 | | | |
| 45 | 1.04E−8 | 1.37E−8 | | | |
| 46 | 9.65E−9 | 1.27E−8 | | | |
| 47 | 1.37E−8 | 1.93E−8 | | | |
| 48 | 1.31E−8 | 2.09E−8 | | | |
| 49 | 4.06E−8 | 8.88E−9 | | | |
| 50 | 2.83E−9 | 4.03E−9 | | | |
| 51 | 5.26E−9 | 9.51E−9 | | | |
| 52 | 6.68E−8 | >1.00E−7 | | | |
| 53 | 3.82E−9 | 6.78E−9 | | | |
| 54 | 1.85E−8 | 3.78E−8 | | | |
| 55 | 1.96E−9 | 3.39E−9 | | | |
| 56 | 4.34E−9 | 7.24E−9 | | | |
| 57 | 5.34E−9 | 1.18E−8 | | | |
| 58 | 4.69E−9 | 7.70E−9 | | | |
| 60 | 2.08E−9 | 4.20E−9 | | | |
| 61 | 1.95E−8 | 3.76E−8 | | | |
| 62 | 1.40E−8 | 2.28E−8 | | | |
| 63 | 4.75E−9 | 6.40E−9 | | | |
| 64 | 1.20E−8 | 2.31E−8 | | | |
| 65 | 1.28E−8 | 1.69E−8 | | | |
| 66 | >1.00E−7 | >1.00E−7 | | | |
| 67 | 2.11E−9 | 3.66E−9 | | | |
| 68 | 3.63E−8 | 7.12E−8 | | | |
| 69 | 1.83E−8 | 3.86E−8 | | | |
| 70 | 2.29E−8 | 3.98E−8 | | | |
| 71 | 7.82E−9 | 1.16E−8 | | | |
| 72 | 4.27E−9 | 6.25E−9 | | | |
| 73 | 9.52E−9 | 1.54E−8 | | | |
| 74 | 1.33E−8 | 2.10E−8 | | | |
| 75 | 2.76E−8 | 4.35E−8 | | | |
| 76 | 5.52E−9 | 8.73E−9 | | | |
| 77 | 2.04E−9 | 4.53E−9 | | | |
| 78 | 5.33E−8 | 6.90E−8 | | | |
| 79 | 4.47E−9 | 6.15E−9 | | | |
| 80 | 2.67E−9 | 4.13E−9 | | | |
| 81 | 1.39E−8 | 2.63E−8 | | | |
| 82 | 1.40E−8 | 2.36E−8 | | | |
| 83 | 3.97E−8 | 6.18E−8 | | | |
| 84 | 1.61E−8 | 4.10E−8 | | | |
| 85 | 1.89E−8 | 4.04E−8 | | | |
| 86 | 1.06E−8 | 5.98E−8 | | | |
| 87 | 3.72E−9 | 8.15E−9 | | | |
| 88 | 9.16E−8 | >1.00E−7 | | | |
| 89 | 7.43E−8 | >1.00E−7 | | | |
| 90 | 1.60E−8 | >1.00E−7 | | | |
| 91 | 5.19E−8 | >1.00E−7 | | | |
| 92 | 4.23E−8 | >1.00E−7 | | | |
| 93 | 5.39E−9 | 2.47E−8 | | | |
| 94 | 7.01E−9 | 3.69E−8 | | | |
| 95 | 9.32E−9 | 6.07E−8 | | | |
| 96 | 1.85E−8 | >1.00E−7 | | | |
| 97 | 1.21E−8 | 8.20E−8 | | | |
| 98 | 1.27E−8 | 6.43E−8 | | | |
| 99 | 3.99E−8 | >1.00E−7 | | | |
| 100 | 2.25E−8 | >1.00E−7 | | | |
| 101 | 1.46E−8 | 3.63E−8 | | | |
| 102 | 2.34E−8 | >1.00E−7 | | | |
| 103 | 3.68E−8 | >1.00E−7 | | | |
| 104 | 1.34E−8 | 7.08E−8 | | | |
| 105 | 2.76E−8 | >1.00E−7 | | | |
| 106 | 4.79E−9 | 2.14E−8 | | | |
| 107 | 9.26E−9 | 5.24E−8 | | | |
| 108 | 6.54E−9 | 1.78E−8 | | | |
| 109 | 5.63E−9 | 1.41E−8 | | | |
| 110 | 8.57E−9 | 3.92E−8 | | | |
| 111 | 3.96E−8 | >1.00E−7 | | | |
| 112 | 1.39E−8 | 5.82E−8 | | | |
| 113 | 3.30E−8 | >1.00E−7 | | | |

Table 4-continued

Anti-proliferation IC$_{50}$ values of several examples in vitro in different cell lines

| Example Compound | HeLa (Cervical cancer) | SK-MEL-3 (melanoma) | IGR-37 (melanoma) | NCI-H1734 | H4 |
|---|---|---|---|---|---|
| 114 | 4.63E−8 | >1.00E−7 | | | |
| 115 | 7.87E−9 | 3.73E−8 | | | |
| 116 | 8.39E−9 | 4.29E−8 | | | |
| 117 | 5.14E−8 | >1.00E−7 | | | |
| 118 | 5.54E−8 | >1.00E−7 | | | |
| 119 | 6.58E−8 | >1.00E−7 | | | |
| 120 | 4.59E−8 | >1.00E−7 | | | |
| 121 | 7.15E−9 | 3.36E−8 | | | |
| 122 | 2.67E−9 | 9.92E−9 | | | |
| 123 | 7.98E−8 | >1.00E−7 | 2.76E−7 | | |
| 124 | 6.90E−9 | 1.68E−8 | 3.29E−8 | | |
| 125 | 1.60E−8 | 3.61E−8 | 5.51E−8 | | |
| 126 | 5.29E−9 | 7.06E−9 | | | |
| 127 | 1.78E−9 | 3.64E−9 | 5.37E−9 | | |
| 128 | 7.79E−9 | 1.52E−8 | 3.48E−8 | | |
| 129 | 2.14E−9 | 4.58E−9 | 4.77E−9 | | |
| 130 | 4.32E−9 | 8.73E−9 | 9.03E−9 | | |
| 131 | 1.77E−8 | 3.62E−8 | 4.38E−8 | | |

Thus one aspect of the invention is the use of the compounds of formula (I) for the treatment of cervical cancer.

Thus one aspect of the invention is the use of the compounds of formula (I) for the treatment of skin cancer, especially melanoma.

Another aspect are compounds of formula (I) which effectively inhibit tumor cell proliferation (e.g. in HeLa cells) with IC$_{50}$ values of <100 nM.

Yet another aspect of the invention is the use of compounds of formula (I), for the treatment of skin cancer, especially melanoma, and cervical cancer.

Another aspect of the invention is the use of compounds of formula (I), for the treatment melanoma and cervical cancer.

Example II

Method for PDE3A Enzyme Inhibition

The commercially available 3H-cAMP Scintillation Proximity Assay (SPA, Perkin Elmer) system was used for enzyme inhibition studies. For the determination of the in vitro effect of test substances on the PDE3A reactions 2 µl of the respective test compound solution in DMSO (serial dilutions) were is placed in wells of microtiter plates (Isoplate-96/200W; Perkin Elmer). 50 µl of a dilution of PDE3A cell extract from Sf9 cells overexpressing human full length PDE3A (SB Drug Discovery, UK) in buffer A (50 mM Tris/HCl pH 7.5, 8.3 mM MgCl2, 1.7 mM EDTA, 0.2% BSA) was added. The dilution of the PDE3A cell extract was chosen such that the reaction kinetics was linear and less than 70% of the substrate was consumed (typical dilution 1:5000). The reaction was started by addition of 50 µl (0.025 µCi) of 1:2000 in buffer A w/o BSA diluted substrate [8-3H] adenosine 3',5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC50 values were determined from sigmoidal curves by plotting percentage PDE3A activity vs log compound concentration.

PDE3B Enzyme Inhibition

The commercially available 3H-cAMP Scintillation Proximity Assay (SPA, Perkin Elmer) system was used for enzyme inhibition studies. For the determination of the in vitro effect of test substances on the PDE3B reactions 2 µl of the respective test compound solution in DMSO (serial dilutions) were placed in wells of microtiter plates (Isoplate-96/200W; Perkin Elmer). 50 µl of a dilution of PDE3B cell extract from Sf9 cells overexpressing human full length PDE3B (SB Drug Discovery, UK) in buffer A (50 mM Tris/HCl pH 7.5, 8.3 mM MgCl2, 1.7 mM EDTA, 0.2% BSA) was added. The dilution of the PDE3B cell extract was chosen such that the reaction kinetics was linear and less than 70% of the substrate was consumed (typical dilution 1:6000). The reaction was started by addition of 50 µl (0.025 µCi) of 1:2000 in buffer A w/o BSA diluted substrate [8-3H] adenosine 3',5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC50 values were determined from sigmoidal curves by plotting percentage PDE3B activity vs log compound concentration.

One aspect of the invention are compounds of formula (I) which effectively inhibit tumor cell proliferation with IC$_{50}$ values of <100 nM in e.g. HeLa cells while IC$_{50}$ values for enzymatic PDE3A inhibition are often >2.5 times higher and/or enzymatic IC$_{50}$ values on PDE3A/B above 10 nM.

One aspect of the invention are compounds of formula (I) which effectively inhibit tumor cell proliferation with IC$_{50}$ values of <100 nM in e.g. HeLa cells while IC$_{50}$ values for enzymatic PDE3A or PDE3B inhibition are often >2.5 times higher than IC$_{50}$ values for tumor cell proliferation.

Another aspect of the invention are compounds of formula (I) which effectively inhibit tumor cell proliferation with IC$_{50}$ values of <100 nM in e.g. HeLa cells while IC$_{50}$ values for enzymatic PDE3A or PDE3B inhibition are often >10 times higher than IC$_{50}$ values for tumor cell proliferation.

One aspect of the invention are compounds of formula (I) which effectively inhibit tumor cell proliferation with IC$_{50}$ values of <100 nM in e.g. HeLa cells while IC$_{50}$ values for enzymatic PDE3A or PDE3B inhibition are often >30 times higher than IC$_{50}$ values for tumor cell proliferation.

TABLE 5

Inhibition of PDE3A and PDE3B

| Compound | Target IC$_{50}$ PDE3A IC$_{50}$ (nM) | Target IC$_{50}$ PDE3B IC$_{50}$ (nM) |
|---|---|---|
| 1 | 470 | 290 |
| 2 | 65 | 67 |
| 3 | 190 | 150 |
| 4 | 420 | 160 |
| 5 | 120 | 39 |
| 6 | 72 | 87 |
| 7 | 200 | 35 |
| 8 | 90 | 49 |
| 9 | 90 | 35 |
| 10 | 110 | 110 |
| 11 | 660 | 710 |
| 12 | 110 | 62 |
| 13 | 310 | 250 |

TABLE 5-continued

Inhibition of PDE3A and PDE3B

| Compound | Target IC$_{50}$ PDE3A IC$_{50}$ (nM) | Target IC$_{50}$ PDE3B IC$_{50}$ (nM) |
|---|---|---|
| 14 | 180 | 77 |
| 15 | 110 | 77 |
| 16 | 405 | 128 |
| 17 | 200 | 89 |
| 18 | 66 | 73 |
| 19 | 210 | 210 |
| 20 | 220 | 160 |
| 21 | 82 | 50 |
| 22 | 159 | 148 |
| 23 | 450 | 470 |
| 24 | 350 | 300 |
| 25 | 210 | 160 |
| 26 | 93 | 90 |
| 27 | 130 | 140 |
| 28 | 100 | 89 |
| 29 | 160 | 110 |
| 30 | 33 | 31 |
| 31 | 160 | 93 |
| 32 | 64 | 36 |
| 33 | 66 | 67 |
| 34 | 57 | 50 |
| 35 | 820 | 690 |
| 36 | 420 | 390 |
| 37 | 130 | 100 |
| 38 | 100 | 100 |
| 39 | 82 | 80 |
| 40 | 140 | 140 |
| 41 | 150 | 100 |
| 42 | 80 | 68 |
| 43 | 110 | 110 |
| 44 | 180 | 95 |
| 45 | 370 | 310 |
| 46 | 61 | 37 |
| 47 | 95 | 96 |
| 48 | 230 | 260 |
| 49 | 63 | 41 |
| 50 | 130 | 130 |
| 51 | 120 | 92 |
| 52 | 95 | 65 |
| 53 | 68 | 34 |
| 54 | 190 | 380 |
| 55 | 50 | 62 |
| 56 | 110 | 62 |
| 57 | 180 | 60 |
| 58 | 250 | 83 |
| 60 | 96 | 47 |
| 61 | 440 | 110 |
| 62 | 120 | 47 |
| 63 | 250 | 88 |
| 64 | 100 | 91 |
| 65 | 120 | 76 |
| 66 | 330 | 290 |
| 67 | 56 | 28 |
| 68 | 160 | 100 |
| 69 | 140 | 95 |
| 70 | 57 | 50 |
| 71 | 120 | 120 |
| 72 | 39 | 35 |
| 73 | 52 | 39 |
| 74 | 110 | 180 |
| 75 | 100 | 120 |
| 76 | 90 | 89 |
| 77 | 100 | 80 |
| 78 | 320 | 600 |
| 79 | 170 | 170 |
| 80 | 220 | 310 |
| 81 | 370 | 230 |
| 82 | 83 | 85 |
| 83 | 560 | 280 |
| 84 | 270 | 220 |
| 85 | 240 | 150 |
| 86 | 280 | 310 |
| 87 | 385 | 215 |
| 88 | 230 | 230 |
| 89 | 140 | 150 |
| 90 | 47 | 65 |
| 91 | 57 | 73 |
| 92 | 61 | 88 |
| 93 | 38 | 49 |
| 94 | 190 | 175 |
| 95 | 180 | 200 |
| 96 | 310 | 260 |
| 97 | 170 | 120 |
| 98 | 180 | 120 |
| 99 | 280 | 530 |
| 100 | 58 | 59 |
| 101 | 67 | 67 |
| 102 | 460 | 555 |
| 103 | 170 | 200 |
| 104 | 120 | 120 |
| 105 | 200 | 200 |
| 106 | 110 | 100 |
| 107 | 270 | 190 |
| 108 | 160 | 210 |
| 109 | 150 | 150 |
| 110 | 240 | 260 |
| 111 | 42 | 32 |
| 112 | 140 | 110 |
| 113 | 88 | 91 |
| 114 | 36 | 53 |
| 115 | 47 | 80 |
| 116 | 220 | 170 |
| 117 | 540 | 440 |
| 118 | 76 | 90 |
| 119 | 290 | 290 |
| 120 | 200 | 180 |
| 121 | 230 | 230 |
| 122 | 280 | 200 |
| 123 | >1000 | >1000 |
| 124 | 59 | 73 |
| 125 | 625 | 335 |
| 126 | 59 | 95 |
| 127 | 73 | 77 |
| 128 | 240 | 210 |
| 129 | 120 | 210 |
| 130 | 89 | 86 |
| 131 | 620 | 385 |

Example III

Method for Human Cryo Hepatocytes:

Investigation of in vitro metabolic stability in cryopreserved human hepatocytes (including calculation of hepatic in vivo blood clearance (CL) and maximal oral bioavailability (Fmax))

Cryopreserved Hepatocytes (e.g. purchased from Celsis InVitroTechnologies) were briefly thawed, washed with 45 mL pre-warmed in in vitro GRO HT medium and centrifuged for 5 min at 50×g. The cell pellet was resuspended in 5 ml of Krebs-Henseleit Butter (KHB). Cell viability was determined by trypan blue exclusion.

For the metabolic stability assay liver cells were distributed in WME containing 5% FCS to glass vials at a density of 1.0×106 vital cells/ml. The test compound was added to a final concentration of 1 μM. During incubation, the hepatocyte suspensions were continuously shaken at 580 rpm and aliquots were taken at 2, 8, 16, 30, 45 and 90 min, to which equal volumes of cold methanol were immediately added.

Samples were frozen at −20° C. over night, after subsequently centrifuged for 15 minutes at 3000 rpm and the supernatant was analyzed with an Agilent 1290 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability (Fmax) was calculated. The hepatic in vivo blood clearance (CLblood) and the maximal oral bioavailability (Fmax) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L/(h*kg)]*fu, blood*CL'intrinsic [L/(h*kg)])/(QH [L/(h*kg)]+fu, blood*CL'intrinsic [L/(h*kg)]); Fmax=1−CLblood/QH and using the following parameter values: Liver blood flow—1.32 L/h/kg human; specific liver weight—21 g/kg body weight; liver cells in vivo—$1.1 \times 10^8$ cells/g liver, liver cells in vitro—$1.0 \times 10^6$/ml.; fu,inc and fu,blood is taken as 1.

Example IV

In Vivo Pharmacokinetics in Non-Rodents (e.g. Dogs)
For in vivo pharmacokinetic experiments test compounds were administered to non-rodents (e.g. female Beagle dogs) intravenously at doses of 0.1 to 1 mg/kg and intragastral at doses of 0.3 to 3 mg/kg formulated as solutions using solubilizers such as PEG400 in well-tolerated amounts and are usually given as short term infusion (15 min).

Blood samples were taken e.g. at 2 min, 8 min, 15 min, 30 min, 45 min, 1 h, 2 h, 4 h, 6 h, 8 h and 24 h after dosing from the vena saphena. Depending on the expected half-life additional samples were taken at later time points (e.g. 48 h, 72 h).

For pharmacokinetics after intragastral administration test compounds were given intragastral to fasted non-rodents (e.g. dogs). Blood samples were taken e.g. at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparin tubes (Monovetten®, Sarstedt) and centrifuged for 15 min at 3000 rpm. A small aliquot (e.g. 100 μL) from the supernatant (plasma) was taken and precipitated by addition of an aliquot ice cold acetonitril (e.g. of 400 μL) and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (abbreviation: CLp;) in L/kg/h) with Cp/Cb being the ratio of concentrations in plasma and blood.

PK parameters calculated from concentration time profiles after i.q.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0−tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

Validation of PDE3A Modulator-Induced PDE3A Protein Interactions Using Immunoprecipitation and Immunoblotting HeLa cells is transfected with ORF overexpression constructs expressing V5-tagged SIRT7, V5-tagged SLFN12, or V5-tagged GFP. ORF expression constructs are obtained from the TRC (clone IDs: TRCN0000468231, TRCN0000476272, ccsbBroad304_99997). At 72 hours post transfection, cells are treated with 10 μM DNMDP or trequinsin for 4 hours followed by lysis using the ModRipa lysis buffer and immunoprecipitation of PDE3A. For each condition, 2 mg total protein lysate is incubated with 1 μg of anti-PDE3A antibody at 4° C. overnight, after which 7.5 μl each of Protein A- and Protein G-Dynabeads (Life Technologies 10001D and 10003D) is added and incubated for another 1 hour. Beads are washed and bound proteins are eluted with 30 μl of LDS PAGE gel loading buffer. Input (~60 μg total protein lysate) and IP products are resolved on 4-12% Tris-Glycine PAGE gels and immunoblotted with an anti-V5 antibody (Life Technologies R96205, 1:5000), the Bethyl anti-PDE3A antibody (1:1000), and secondary antibodies from LiCOR Biosciences (Cat. #926-32210 and 926068021, each at 1:10,000). Blots are washed and imaged using a LiCOR Odyssey infrared imager.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

The invention claimed is:
1. A method of preparing a compound of general formula (I) having the structure:

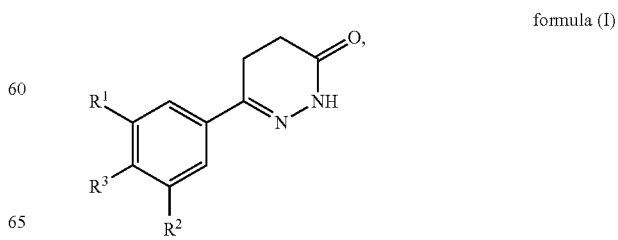

formula (I)

said method comprising the step of allowing an intermediate compound of general formula (II) to react:

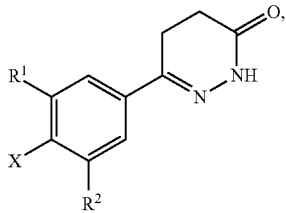

(II)

in which
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a halogen atom; and
X=F, Cl, Br, or I
to form the compound of general formula (I); wherein
a) if X=Cl, Br, or I, with the prerequisite that R$^1$/R$^2$ is not Cl, Br, or I, the method comprises allowing the compound of Formula (II) to react under transmetal catalyzed coupling conditions with a boronic acid of formula (IIIa)

(R$^x$)B(OH)$_2$  (IIIa)

whereby R$^x$ is
a C$_1$-C$_6$-alkoxy group,
a C$_2$-C$_6$-alkenyl group,
a C$_3$-C$_6$-cycloalkyl group,
a C$_5$-C$_6$-cycloalkenyl group,
a 3- to 7-membered heterocycloalkyl group, which is optionally substituted with one, two, or three substituents and each substituent is independently selected from a halogen atom, a C$_1$-C$_3$-alkyl group, a hydroxy group, NR$^4$R$^5$ group, a C$_1$-C$_3$-haloalkyl group and a C$_1$-C$_3$-haloalkoxy group,
a 5- to 7-membered heterocycloalkyl group which is partially unsaturated and optionally substituted with one, two or three substituents and each substituent is independently selected from an oxo group (=O), a C$_1$-C$_3$-alkyl group and a halogen atom,
an aryl group which is optionally substituted with one, two, three or four substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, a —C(O)NR$^4$R$^5$ group and a NR$^4$R$^5$ group;
a mono- or bicyclic heteroaryl group which is optionally substituted with one, two or three substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, and a NR$^4$R$^5$ group; or
a NR$^6$R$^7$ group,
R$^4$/R$^5$ is independently selected from a hydrogen atom, a C$_1$-C$_6$-alkyl group, a —C$_1$-C$_5$-alkylen-O—C$_1$-C$_5$-alkyl group, a —C$_1$-C$_5$-alkylen-S—C$_1$-C$_5$-alkyl group, a C$_3$-C$_6$-cycloalkyl group, and a 3- to 5-membered heterocycloalkyl group;
R$^6$/R$^7$ is independently selected from a hydrogen atom, a C$_1$-C$_6$-alkyl group, a —C$_1$-C$_5$-alkylen-O—C$_1$-C$_5$-alkyl group, a —C$_1$-C$_5$-alkylen-S—C$_1$-C$_5$-alkyl group, a —C$_1$-C$_5$-alkylen-NR$^8$—C$_1$-C$_5$-alkyl group, a —C$_1$-C$_5$-hydroxyalkylen-(C$_1$-C$_3$-haloalkyl) group, a C$_3$-C$_6$-cycloalkyl group, and a 3- to 5-membered heterocycloalkyl group,
or R$^6$ and R$^7$ together form a 3-, 4-, 5-, 6- or 7-membered ring optionally containing one or two additional heteroatoms selected from the group consisting of —O—, —S— and —NR$^8$—,
and which is optionally substituted one, two, or three times with a substituent selected from a halogen atom, a hydroxy group, and a C$_1$-C$_3$-alkyl group
and if R$^6$ and R$^7$ together form a 5-, 6- or 7-membered ring, said ring can optionally contain a bridging group selected from a bond, —O—, —NR$^8$—, —CH$_2$—, —CH$_2$—CH$_2$—, —O—CH$_2$—, —NR$^8$—CH$_2$—;
R$^8$ is a hydrogen atom or a C$_1$-C$_3$-alkyl group; or
a boronic ester of formula (IIIb)

(R$^x$)B(OR$^y$)$_2$  (IIIb)

wherein R$^x$ is as defined for the boronic acid above and R$^y$ is C$_1$-C$_6$-alkyl, or the two residues R$^y$ together form a pinacol ester, /potassium carbonate/a palladium catalyst selected from the following list:
dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium (II) chloride, 1,3-bis(2,6-diisopropylphenyl)imidazol-2-ylidene(1,4-naphthoquinone)palladium dimer, allyl (chloro)(1,3-dimesityl-1,3-dihydro-2H-imidazol-2-ylidene)palladium, palladium(II) acetate/dicyclohexyl (2',4',6'-triisopropyl-biphenyl-2-yl)phosphine, [1,1-bis (diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl) [2-(2'-amino-1,1'-biphenyl)]palladium(II), or (2-Dicyclohexylphosphino-2',4',6'-triisopropyl-1,1'-biphenyl)[2-(2'-amino-1,1'-biphenyl)]palladium(II),
preference being given to chloro(2-dicyclohexylphosphino-2', 4', 6'-triisopropyl-1, 1'-biphenyl)[2-(2'-amino-1, 1'-biphenyl)]palladium(II) in order to obtain a compound of formula (I) wherein R$^3$ is R$^x$
or
b) if X=F, with the prerequisite that R$^1$ is selected from a hydrogen atom, a halogen atom, a cyano group, and a C$_1$-C$_3$-haloalkyl group, and R$^2$ is selected from a hydrogen atom and a halogen atom,
the method comprises allowing the compound of Formula (II) to react with HNR$^7$R$^8$;
optionally in the presence of a base, and optionally in the presence of an inert solvent, and optionally heat, up to the boiling point of the present solvent;
in order to obtain a compound of formula (I) wherein R$^3$ is NR$^7$R$^8$.

2. The method according to claim 1 wherein the transmetal catalyzed coupling conditions are suitable for Negishi couplings, Kumada couplings, and Stille couplings.

3. The method according to claim 1 wherein the transmetal catalyzed coupling conditions are suitable for Suzuki couplings.

* * * * *